(12) United States Patent
Xia et al.

(10) Patent No.: US 8,227,801 B2
(45) Date of Patent: Jul. 24, 2012

(54) BICARBZOLE CONTAINING COMPOUNDS FOR OLEDS

(75) Inventors: Chuanjun Xia, Lawrenceville, NJ (US);
Yonggang Wu, Lawrenceville, NJ (US);
Suman Layek, Lawrenceville, NJ (US);
James Fiordeliso, Yardley, PA (US)

(73) Assignee: Universal Display Corporation, Ewing, NJ (US)

( * ) Notice: Subject to any disclaimer, the term of this patent is extended or adjusted under 35 U.S.C. 154(b) by 147 days.

(21) Appl. No.: 12/767,433

(22) Filed: Apr. 26, 2010

(65) Prior Publication Data
US 2011/0260138 A1 Oct. 27, 2011

(51) Int. Cl.
*H01L 35/24* (2006.01)
(52) U.S. Cl. .................................. 257/40; 257/E51.001
(58) Field of Classification Search ............... 257/40, 257/E51.001
See application file for complete search history.

(56) References Cited

U.S. PATENT DOCUMENTS

| | | | |
|---|---|---|---|
| 4,769,292 A | 9/1988 | Tang et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 7,279,704 B2 | 10/2007 | Walters et al. |
| 2003/0230980 A1 | 12/2003 | Forrest et al. |
| 2004/0174116 A1 | 9/2004 | Lu et al. |
| 2006/0046172 A1 | 3/2006 | Vaitkeviciene |
| 2009/0153034 A1 | 6/2009 | Lin |
| 2011/0006670 A1 * | 1/2011 | Katakura et al. ............. 313/504 |

FOREIGN PATENT DOCUMENTS

| | | |
|---|---|---|
| EP | 1838671 | 10/2007 |
| WO | WO 2006/061759 | 6/2006 |
| WO | WO 2009060742 A1 * | 5/2009 |

OTHER PUBLICATIONS

Vaitkeviciene et al, "Well-defined [3,3']bicarbazolyl-based electroactive compounds for optoelectronics," Synthetic Metals, 158, 2008, pp. 383-390.*
The International Search Report corresponding to the PCT/2011/033782 application.
Baldo et al., "Highly Efficient Phosphorescent Emission from Organic Electroluminescent Devices," Nature, vol. 395, 151-154, 1998.
Baldo et al., "Very high-efficiency green organic light-emitting devices based on electrophosphorescence," Appl. Phys. Lett., vol. 75, No. 3, 4-6 (1999).
U.S. Appl. No. 10/233,470, filed Sep. 4, 2002.

* cited by examiner

*Primary Examiner* — Anthony Ho
(74) *Attorney, Agent, or Firm* — Kilpatrick Townsend & Stockton LLP

(57) ABSTRACT

Novel organic compounds comprising a bicarbazole core are provided. In particular, the compound has a 3;3'-bicarbazole core substituted at the $9^{th}$ position with at least one of dibenzofuran, dibenzothiophene, dibenzoselenophene, azadibenzofuran, azadibenzothiophene and azadibenzoselenophene. The compounds may be used in organic light emitting devices to provide devices having improved efficiency and improved lifetime.

23 Claims, 3 Drawing Sheets

At least one of $R_1$ and $R_2$ has the structure:

At least one of R₁ and R₂ has the structure:

BICARBZOLE CONTAINING COMPOUNDS FOR OLEDS

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the present invention pertains to phosphorescent organic materials comprising a bicarbazole with a dibenzo or azadibenzo substitution.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303.238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

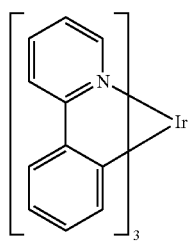

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Compounds comprising a bicarbazole are provided. The compounds have the formula:

Formula I

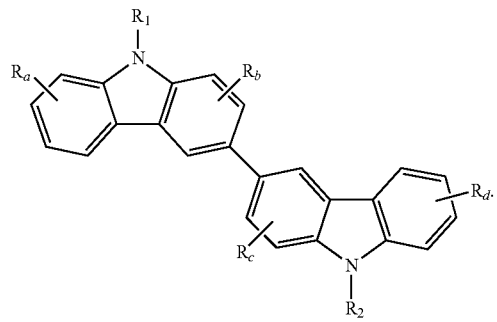

$R_a$, $R_b$, $R_c$, and $R_d$ may represent mono, di, tri, or tetra substitutions. $R_a$, $R_b$, $R_c$, $R_d$, $R_1$, and $R_2$ are independently selected from the group consisting of hydrogen, alkyl, alkoxy, amino, alkenyl, alkynyl, aryl and heteroaryl. Preferably, $R_1$ and $R_2$ are independently selected from aryl and heteroaryl. At least one of $R_1$ and $R_2$ has the formula:

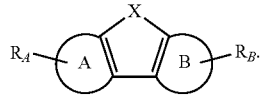

A and B are independently 5 or 6 membered carbocyclic or heterocyclic rings. Preferably, A and B are independently selected from phenyl and pyridine. $R_A$ and $R_B$ are independently selected from the group consisting of hydrogen, alkyl, alkoxy, amino, alkenyl, alkynyl, aryl and heteroaryl. X is S, O or Se.

In one aspect, only one of $R_1$ and $R_2$ has the formula:

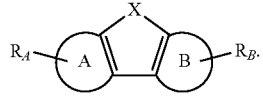

In another aspect, both $R_1$ and $R_2$ have the formula:

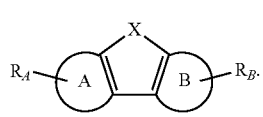

In one aspect, at least one of $R_1$ and $R_2$ has the formula:

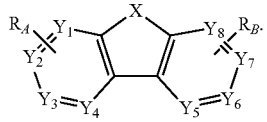

$R_A$ and $R_B$ may represent mono, di, tri, or tetra substitutions. $R_A$ and $R_B$ are independently selected from the group consisting of hydrogen, alkyl, alkoxy, amino, alkenyl, alkynyl, aryl and heteroaryl. $Y_1$, $Y_2$, $Y_3$, $Y_4$, $Y_5$, $Y_6$, $Y_7$, and $Y_8$ are independently selected from nitrogen and carbon.

In one aspect, $R_1$ and $R_2$ are independently selected from the group consisting of:

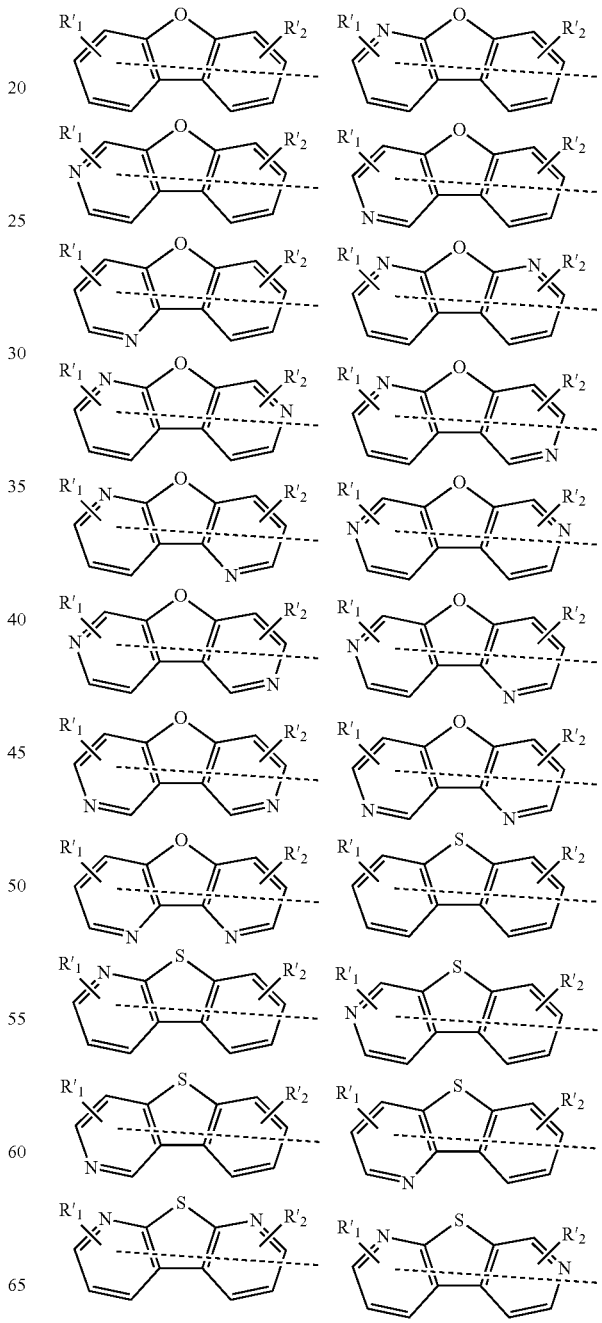

-continued

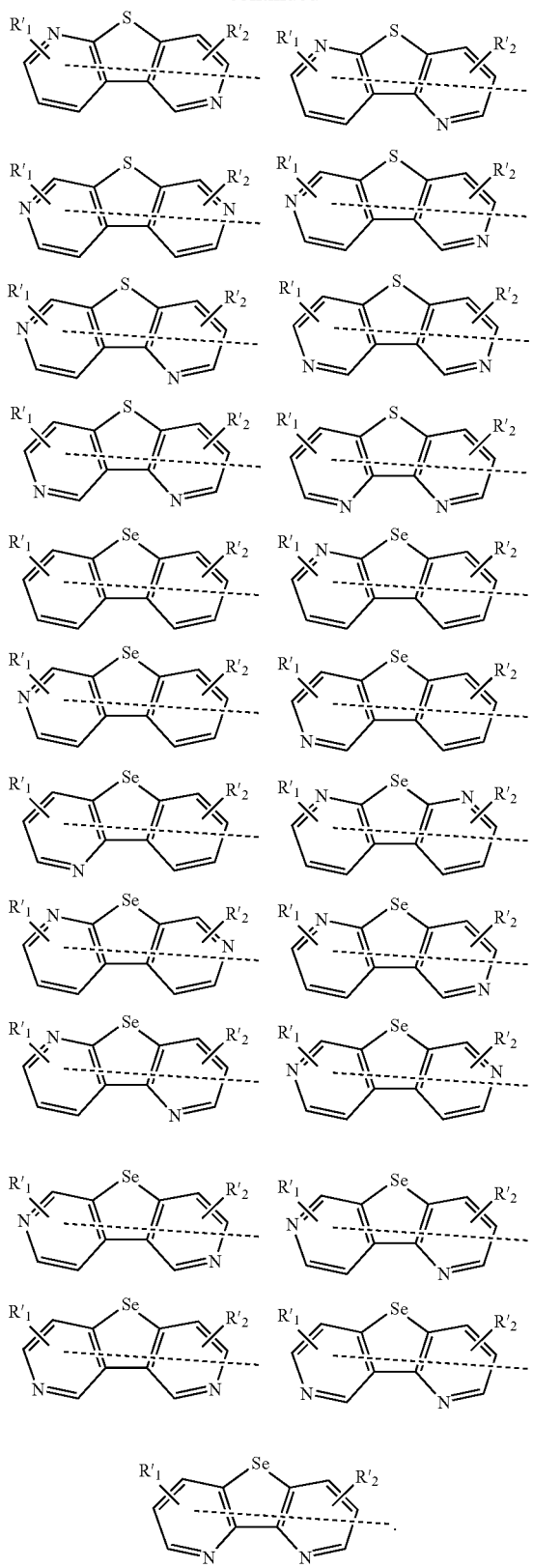

R'₁ and R'₂ are independently selected from the group consisting of hydrogen, alkyl, alkoxy, amino, alkenyl, alkynyl, aryl and heteroaryl.

In another aspect, the compound has the formula:

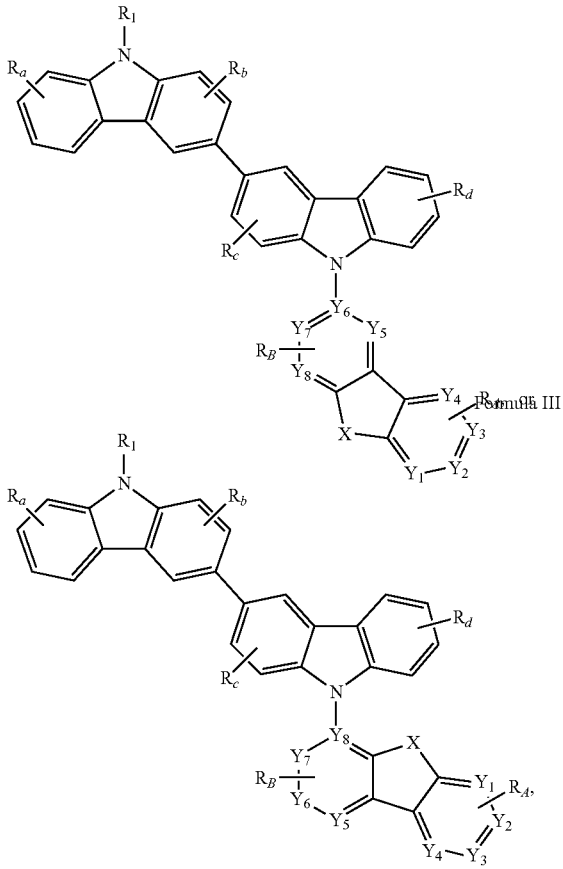

Formula II

Formula III $R_A$ and $R_B$ may represent mono, di, tri, or tetra substitutions. $R_A$ and $R_B$ are independently selected from the group consisting of hydrogen, alkyl, alkoxy, amino, alkenyl, alkynyl, aryl and heteroaryl. $Y_1, Y_2, Y_3, Y_4, Y_5, Y_6, Y_7,$ and $Y_8$ are independently selected from nitrogen and carbon.

Specific examples of compounds comprising bicarbazole are also provided. In particular, the compound is selected from the group consisting of:

Compound 1

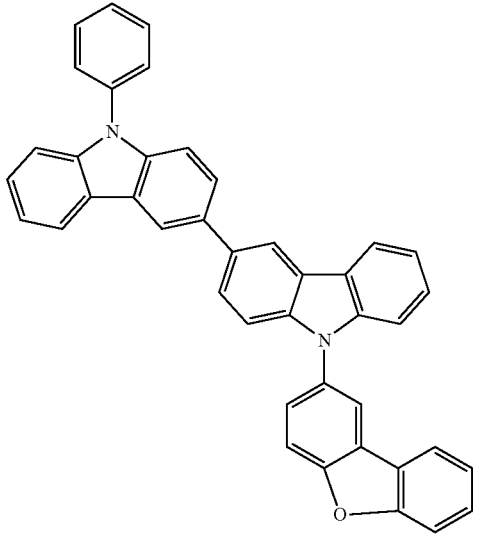

Compound 2
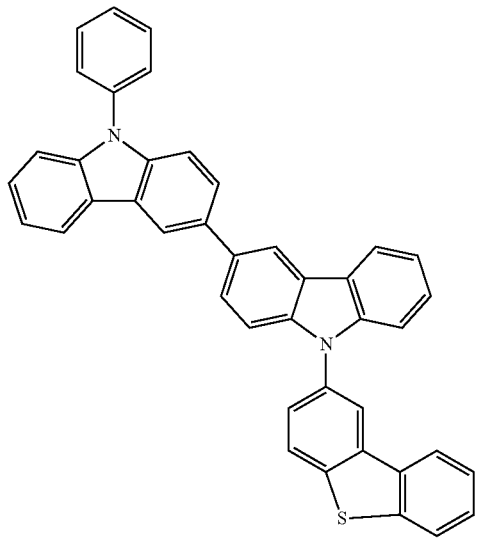
Compound 3
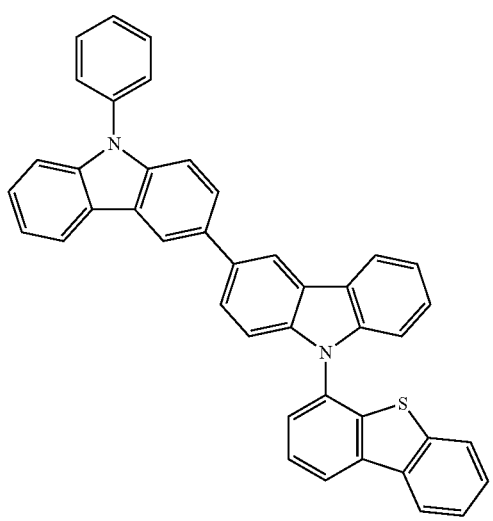
Compound 4
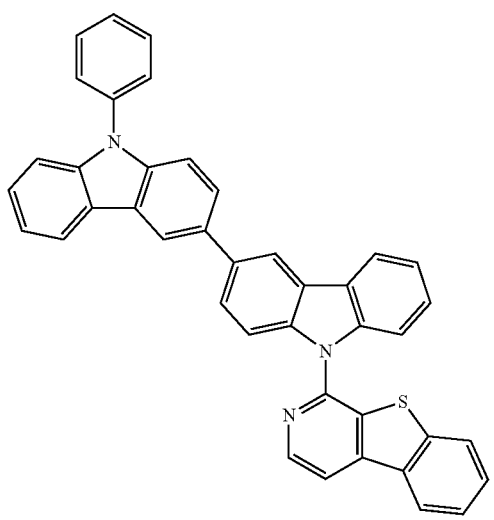
Compound 5
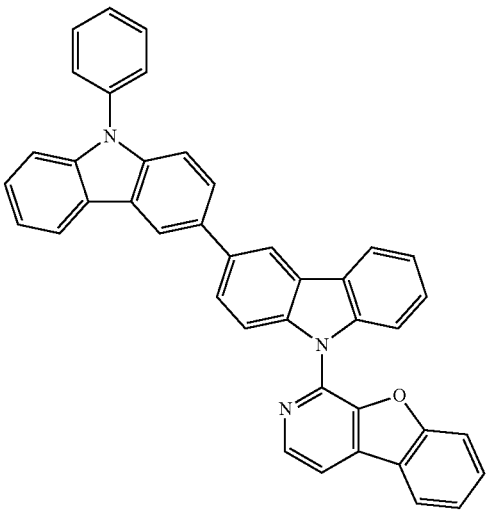
Compound 6
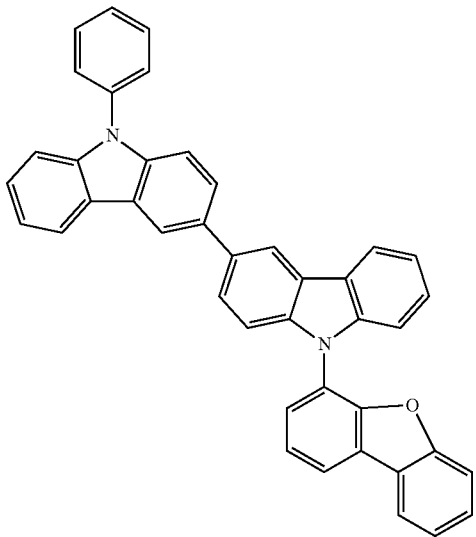

Compound 7
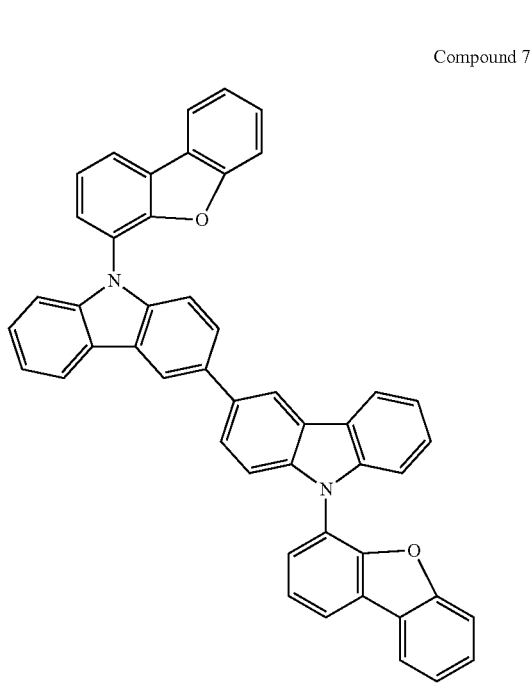
Compound 8
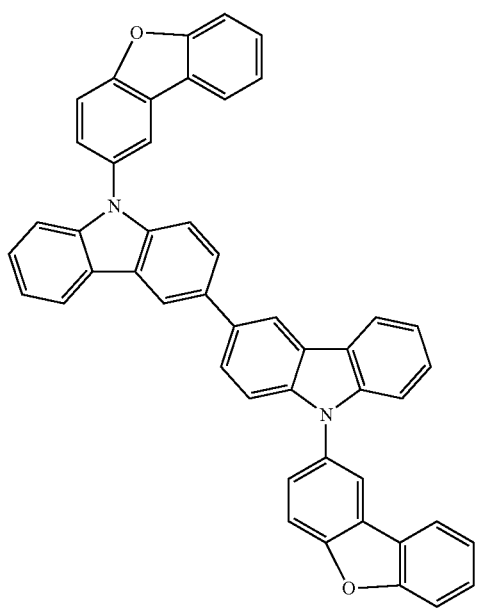
Compound 9
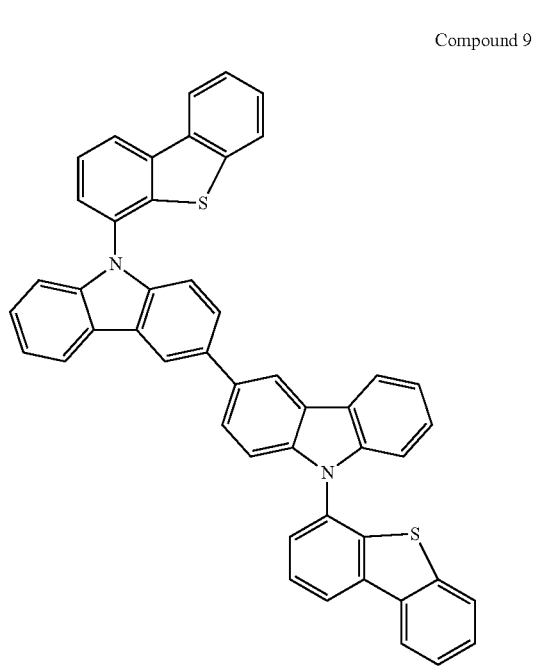
Compound 10
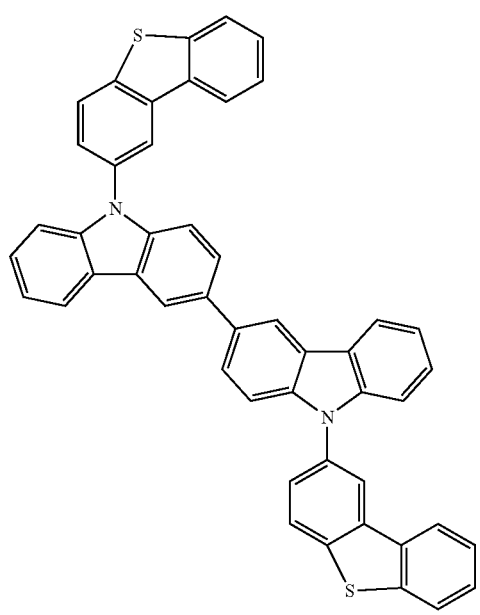

Compound 11
Compound 12
Compound 13
Compound 14
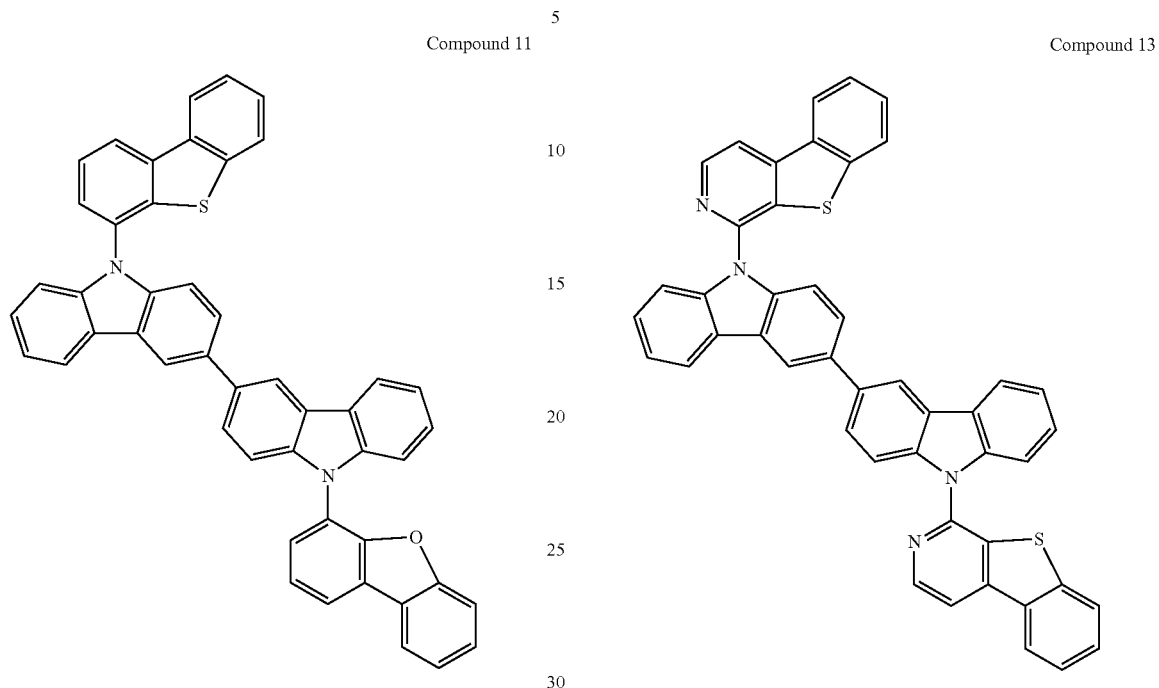

-continued

Compound 15

Compound 16

-continued

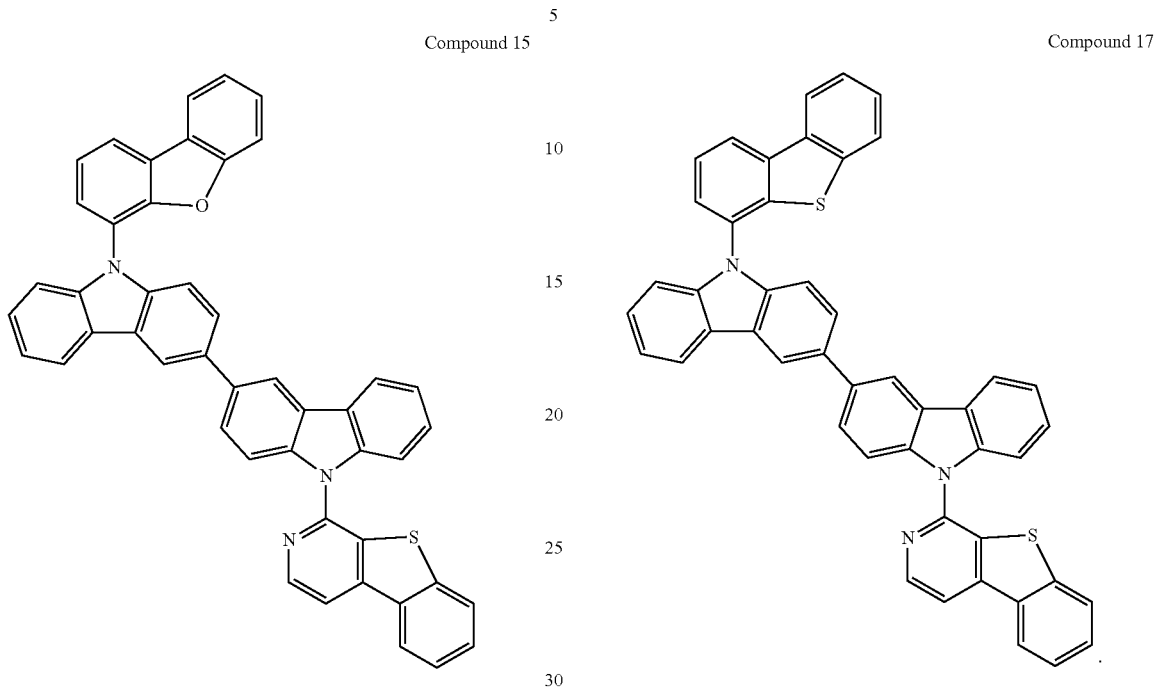

Compound 17

A first device comprising an organic light emitting device is also provided. The device further comprises an anode; a cathode; and an organic layer, disposed between the anode and the cathode. The organic layer comprises a compound comprising a bicarbazole, wherein the compound has Formula I, as described above.

$R_a$, $R_b$, $R_c$, and $R_d$ may represent mono, di, tri, or tetra substitutions. $R_a$, $R_b$, $R_c$, $R_d$, $R_1$, and $R_2$ are independently selected from the group consisting of hydrogen, alkyl, alkoxy, amino, alkenyl, alkynyl, aryl and heteroaryl. Preferably, $R_1$ and $R_2$ are independently selected from aryl and heteroaryl. At least one of $R_1$ and $R_2$ has the formula:

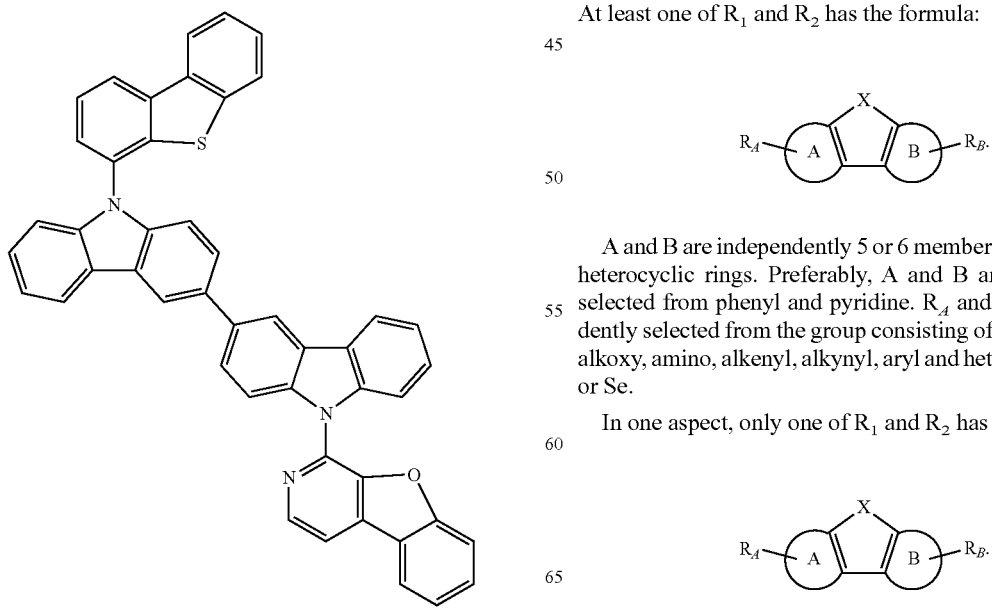

A and B are independently 5 or 6 membered carbocyclic or heterocyclic rings. Preferably, A and B are independently selected from phenyl and pyridine. $R_A$ and $R_B$ are independently selected from the group consisting of hydrogen, alkyl, alkoxy, amino, alkenyl, alkynyl, aryl and heteroaryl. X is S, O or Se.

In one aspect, only one of $R_1$ and $R_2$ has the formula:

In another aspect, both $R_1$ and $R_2$ have the formula:

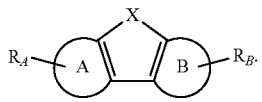

In one aspect, at least one of $R_1$ and $R_2$ has the formula:

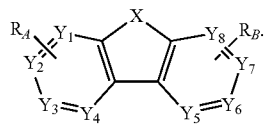

$R_A$ and $R_B$ may represent mono, di, tri, or tetra substitutions. $R_A$ and $R_B$ are independently selected from the group consisting of hydrogen, alkyl, alkoxy, amino, alkenyl, alkynyl, aryl and heteroaryl. $Y_1$, $Y_2$, $Y_3$, $Y_4$, $Y_5$, $Y_6$, $Y_7$, and $Y_8$ are independently selected from nitrogen and carbon.

In one aspect, $R_1$ and $R_2$ are independently selected from the group consisting of:

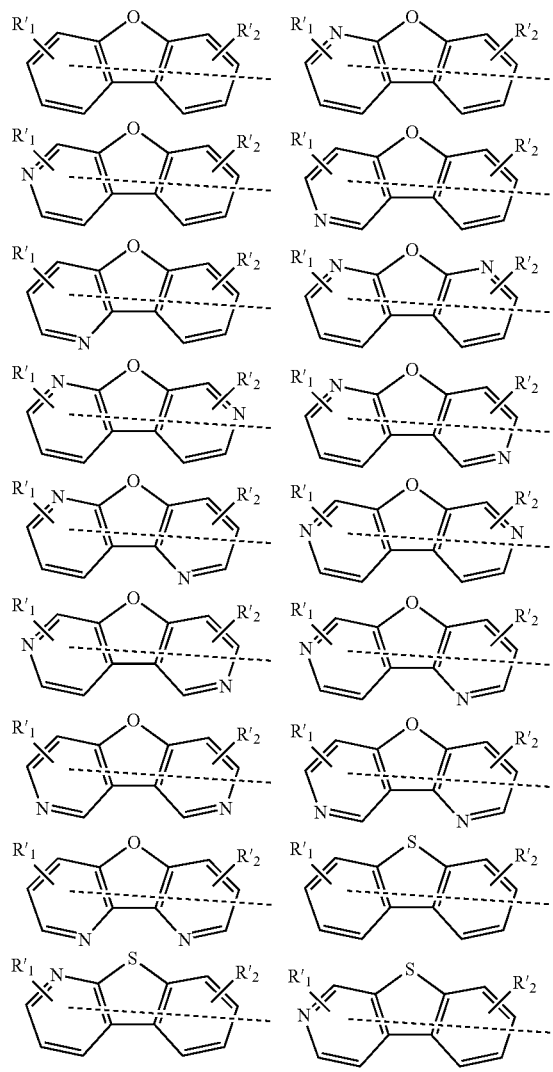

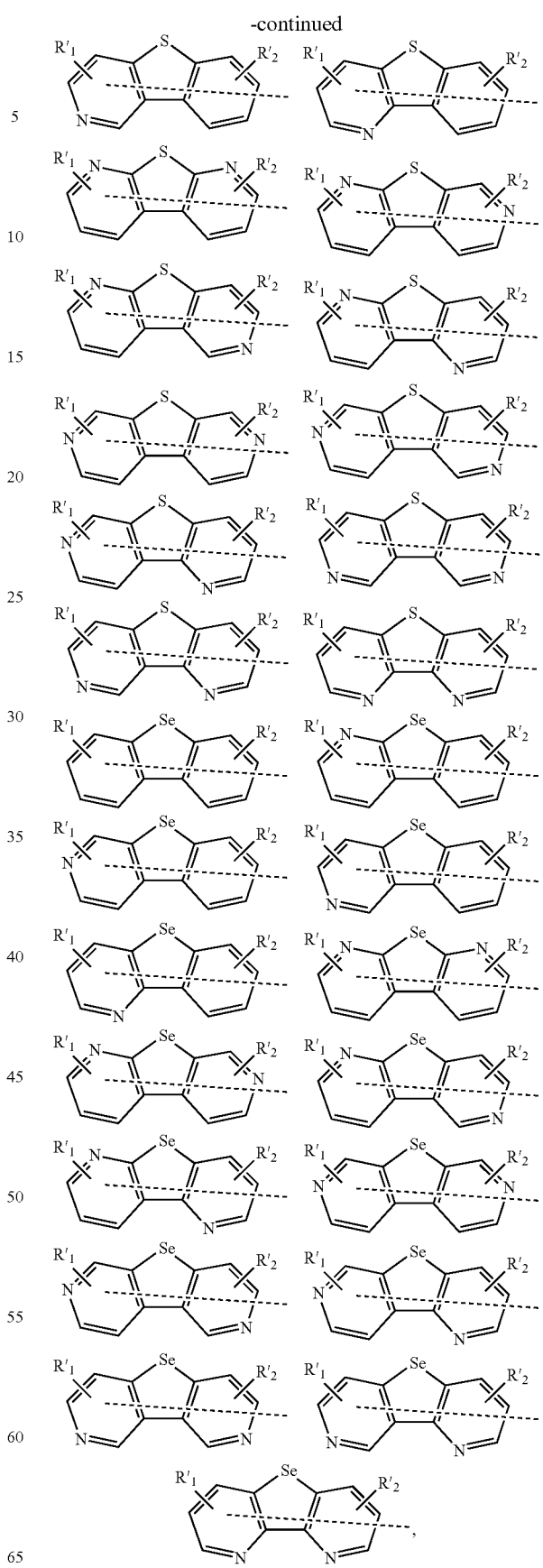

R′$_1$ and R′$_2$ are independently selected from the group consisting of hydrogen, alkyl, alkoxy, amino, alkenyl, alkynyl, aryl and heteroaryl.

In another aspect, the device comprises a compound having Formula II or Formula III.

R$_A$ and R$_B$ may represent mono, di, tri, or tetra substitutions. R$_A$ and R$_B$ are independently selected from the group consisting of hydrogen, alkyl, alkoxy, amino, alkenyl, alkynyl, aryl and heteroaryl. Y$_1$, Y$_2$, Y$_3$, Y$_4$, Y$_5$, Y$_6$, Y$_7$, and Y$_8$ are independently selected from nitrogen and carbon.

Specific examples of devices containing compounds comprising bicarbazole are also provided. In particular, the compound is selected from the group consisting of Compound 1-Compound 17.

In one aspect, the organic layer is a blocking layer and the compound having Formula I is a blocking material.

In another aspect, the organic layer is an emissive layer and the compound having Formula I is a host. In yet another aspect, the emissive layer further comprises a phosphorescent emissive dopant having the formula:

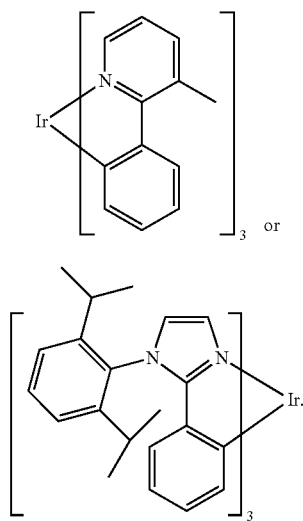

In one aspect, the first device is a consumer product. In another aspect, the first device is an organic light emitting device.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
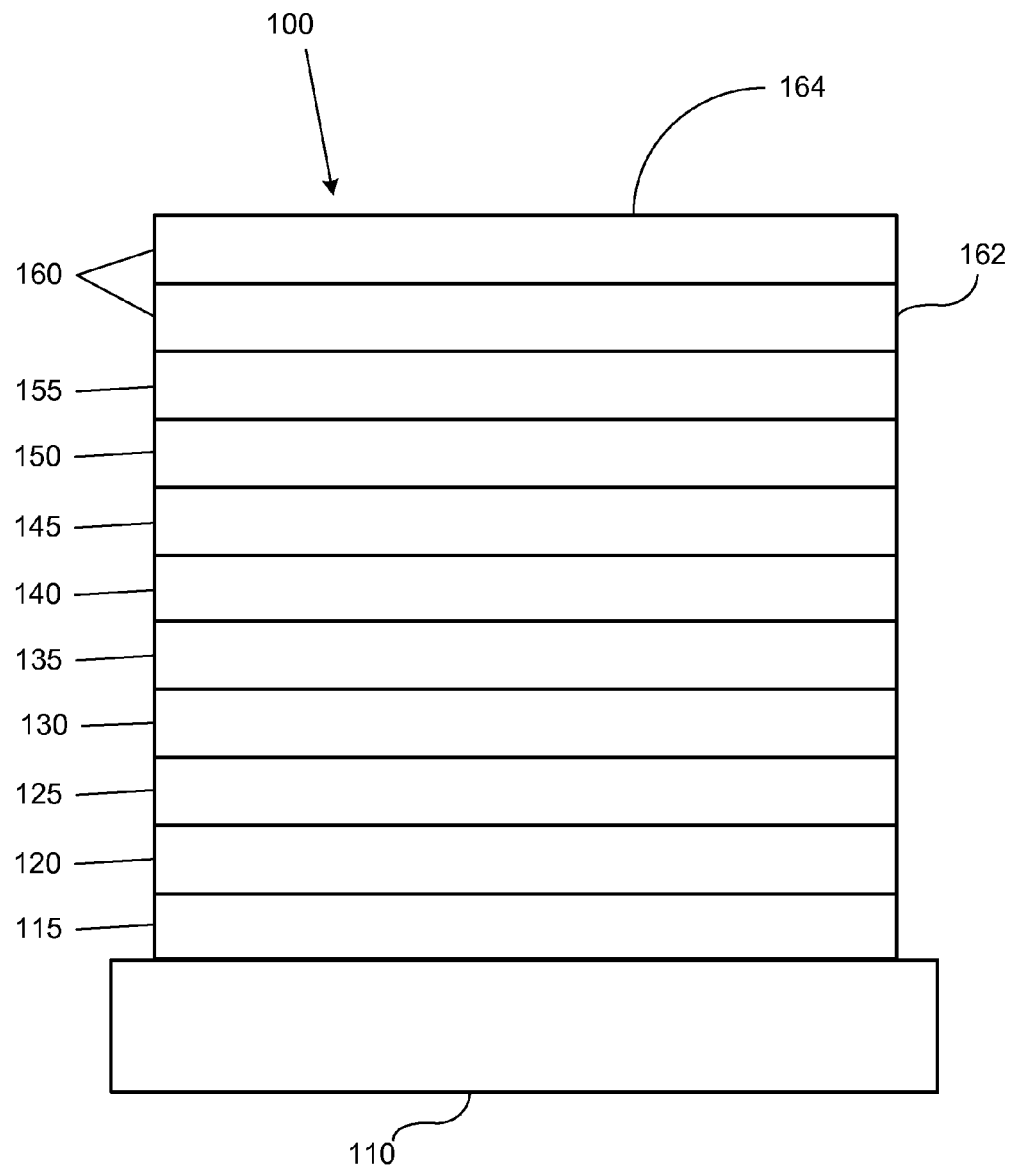
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
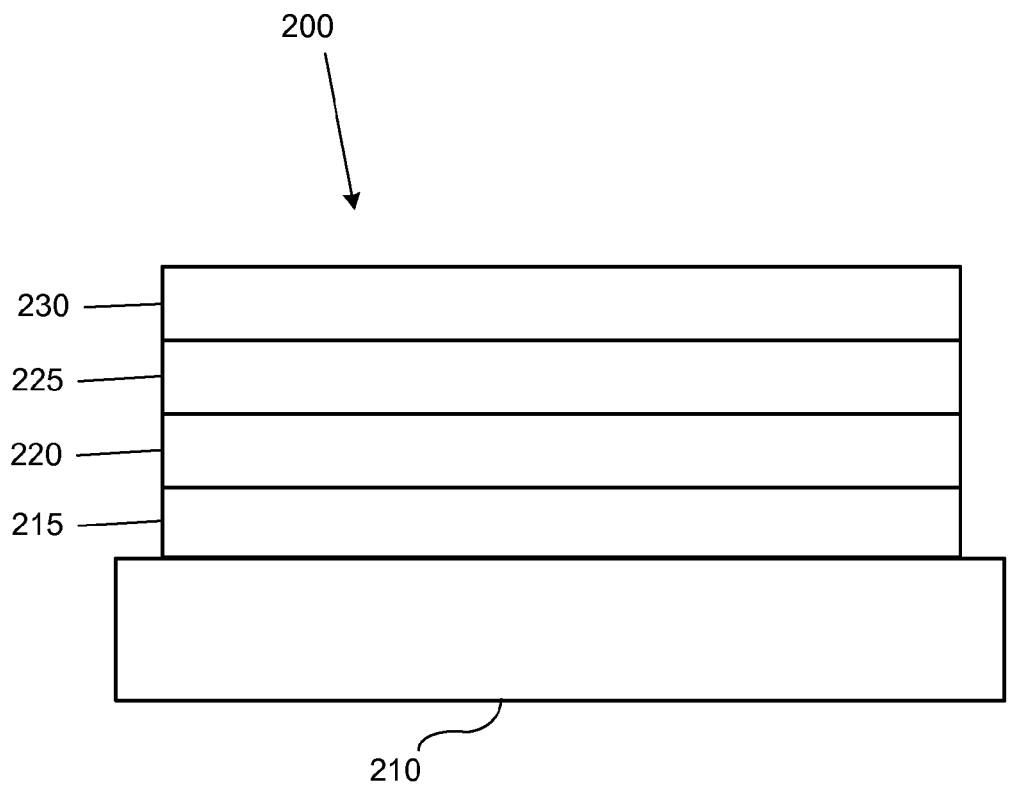
FIG. 2 shows an inverted organic light emitting device that docs not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
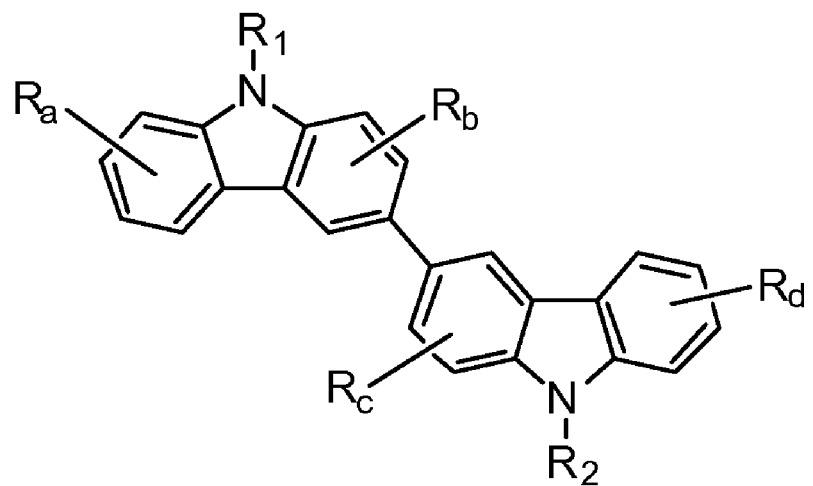
FIG. 3 shows bicarbazole compound.
Figure 3:
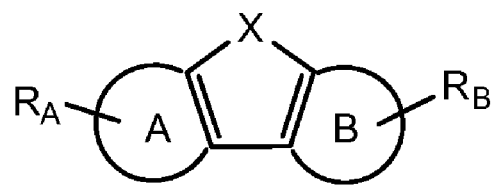

Novel bicarbazole containing compounds are provided (illustrated in FIG. 3). The compounds may be used as host materials or blocking materials for phosphorescent OLEDs. The compounds contain a 3,3'-bicarbazole core substituted at the 9$^{th}$ position by at least one of dibenzofuran, dibenzothiophene, dibenzoselenophene, azadibenzofuran, azadibenzothiophene, and azadibenzoselenophene.

Carbazole is a known building block for OLED materials. In particular, compounds containing 3,3'-bicarbazole have good hole transporting properties, but have poor stability toward electrons. For example, 3,3'-bicarbazole has a shallower HOMO than 9-arylcarbazole. Additionally, alkyl and aryl substituted 3,3'-bicarbazole compounds have been used as hole transporting layer materials and hosts for OLEDs; however, these compounds also have poor electron stability and, thus, may provide devices with limited lifetime. For example, a diaryl substituted 3,3'-bicarbazole, i.e., H1, has a HOMO around 5.6 eV, very good for hole transporting but poor for electron stability. Therefore, the 3,3'-bicarbazole compounds reported in the literature provide devices with limited lifetime.

In the present invention, 3,3'-bicarbazole compounds are substituted at the 9$^{th}$ position with at least one of dibenzofuran, dibenzothiophene, dibenzoselenophene, azadibenzofuran, azadibenzothiophene, and azadibenzoselenophene. These substituents tune the HOMO/LUMO levels as well as increase the stability of the compound toward electrons, which may provide OLEDs with improved stability. Azadibenzo-substituted bicarbazoles, in particular, may be more electron transporting than dibenzo-substituted bicarbazoles, and thus may provide devices with lower operating voltage. Additionally, the bicarbazole compound provided herein may be advantageously used as a blocking layer material as well as a host material. Therefore, the 3,3'-bicarbazole compounds substituted at the $9^{th}$ position with a dibenzo or azadibenzo group may provide devices having improved lifetime and improved efficiency.

Compounds comprising a bicarbazole are provided. The compounds have the formula:

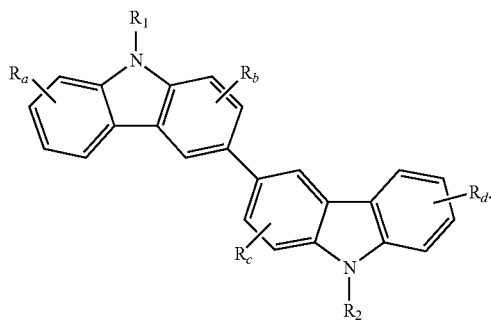

Formula I $R_a$, $R_b$, $R_c$, and $R_d$ may represent mono, di, tri, or tetra substitutions. $R_a$, $R_b$, $R_c$, $R_d$, $R_1$, and $R_2$ are independently selected from the group consisting of hydrogen, alkyl, alkoxy, amino, alkenyl, alkynyl, aryl and heteroaryl. Preferably, $R_1$ and $R_2$ are independently selected from aryl and heteroaryl. At least one of $R_1$ and $R_2$ has the formula:

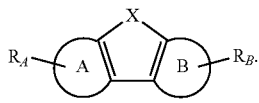

A and B are independently 5 or 6 membered carbocyclic or heterocyclic rings. Preferably, A and B are independently selected from phenyl and pyridine. $R_A$ and $R_B$ are independently selected from the group consisting of hydrogen, alkyl, alkoxy, amino, alkenyl, alkynyl, aryl and heteroaryl. X is S, O or Se.

In one aspect, only one of $R_1$ and $R_2$ has the formula:

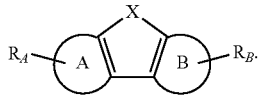

In another aspect, both $R_1$ and $R_2$ have the formula:

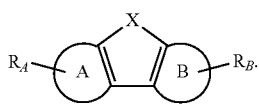

In one aspect, at least one of $R_1$ and $R_2$ has the formula:

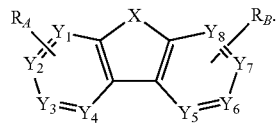

$R_A$ and $R_B$ may represent mono, di, tri, or tetra substitutions. $R_A$ and $R_B$ are independently selected from the group consisting of hydrogen, alkyl, alkoxy, amino, alkenyl, alkynyl, aryl and heteroaryl. $Y_1$, $Y_2$, $Y_3$, $Y_4$, $Y_5$, $Y_6$, $Y_7$, and $Y_8$ are independently selected from nitrogen and carbon.

In one aspect, $R_1$ and $R_2$ are independently selected from the group consisting of:

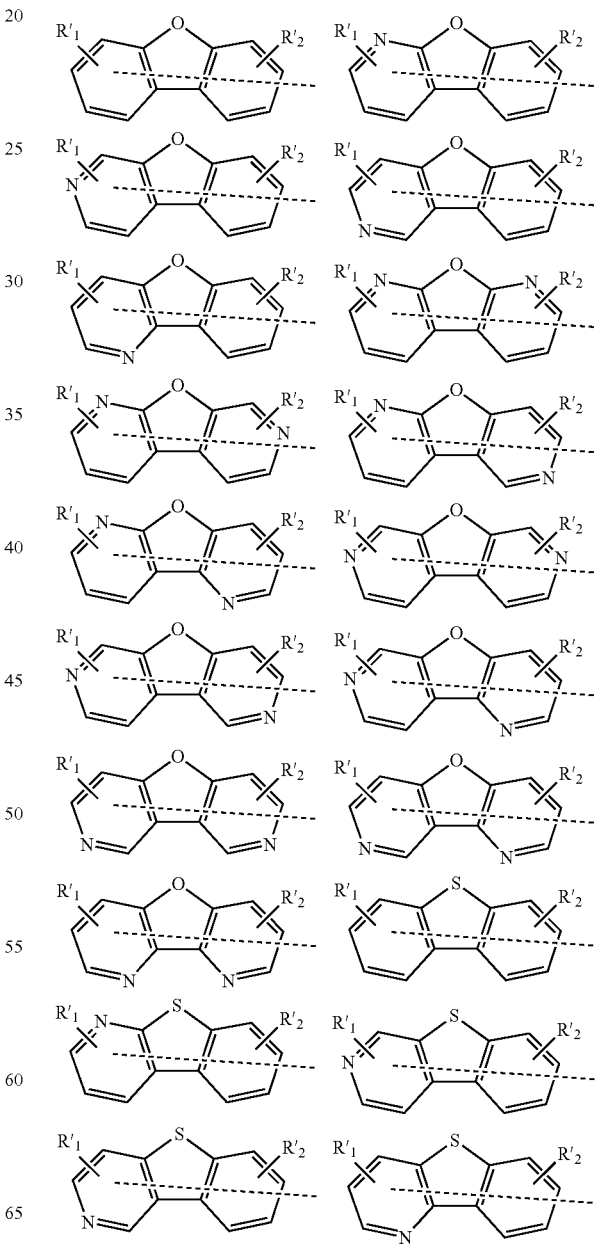

-continued

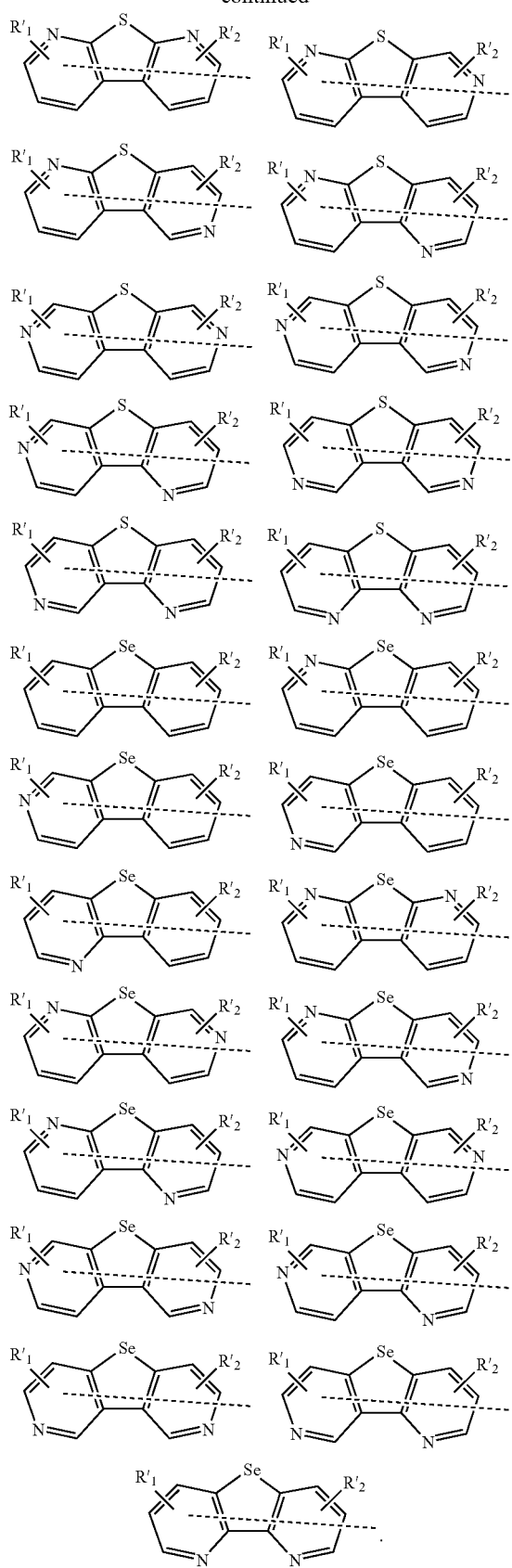

R'$_1$ and R'$_2$ are independently selected from the group consisting of hydrogen, alkyl, alkoxy, amino, alkenyl, alkynyl, aryl and heteroaryl.

In another aspect, the compound has the formula:

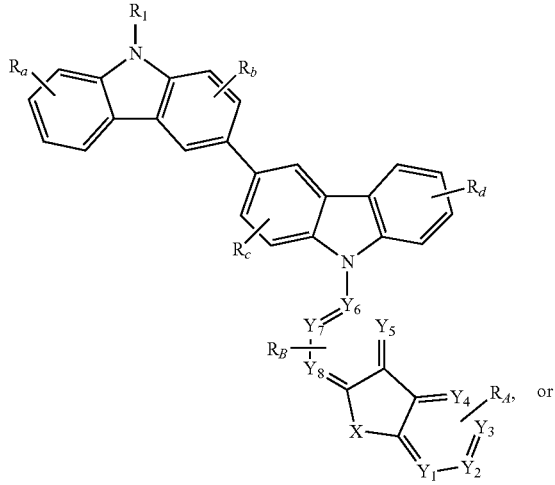

Formula II

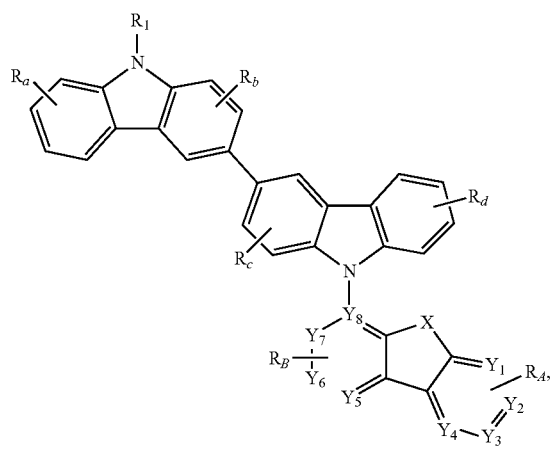

Formula III

R$_A$ and R$_B$ may represent mono, di, tri, or tetra substitutions. R$_A$ and R$_B$ are independently selected from the group consisting of hydrogen, alkyl, alkoxy, amino, alkenyl, alkynyl, aryl and heteroaryl. Y$_1$, Y$_2$, Y$_3$, Y$_4$, Y$_5$, Y$_6$, Y$_7$, and Y$_8$ are independently selected from nitrogen and carbon.

Specific examples of compounds comprising bicarbazole are also provided. In particular, the compound is selected from the group consisting of:

Compound 1
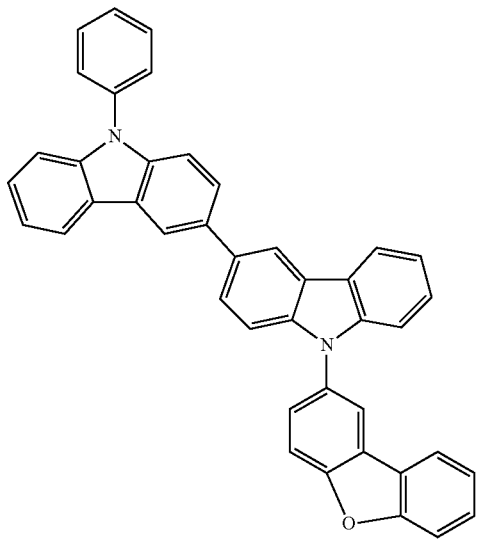
Compound 2
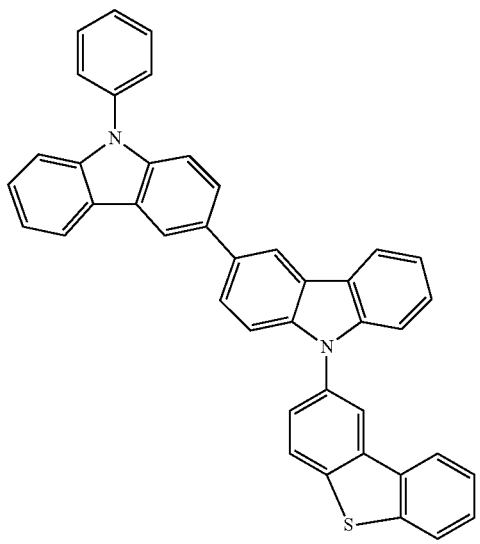
Compound 3
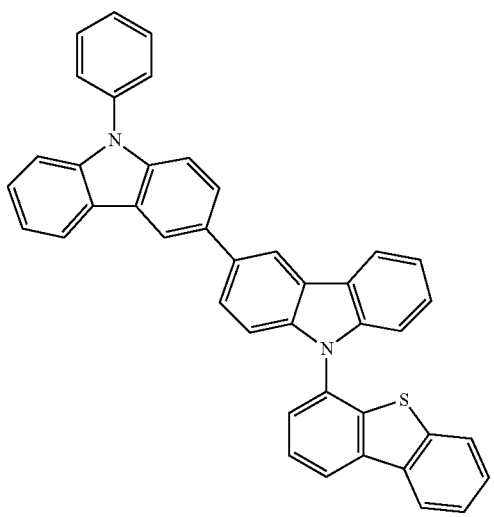
Compound 4
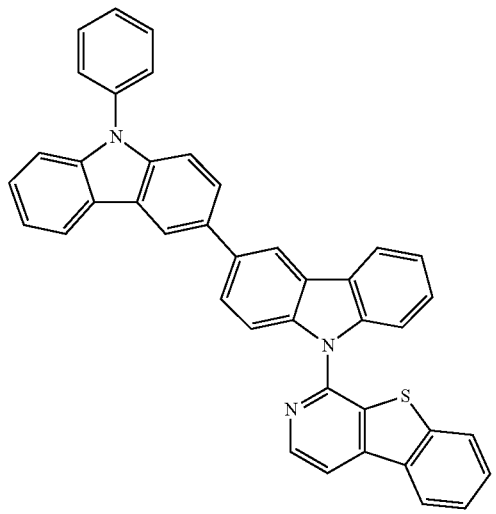
Compound 5
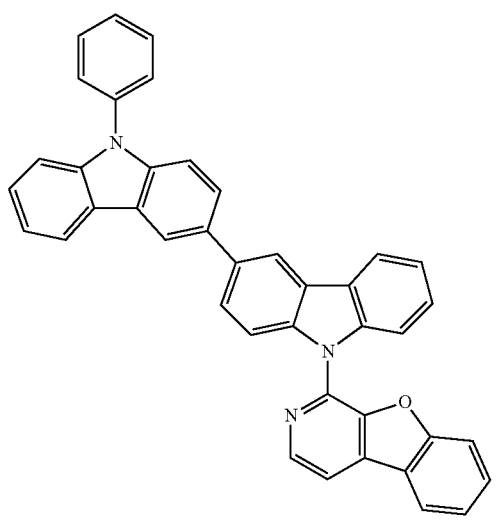
Compound 6
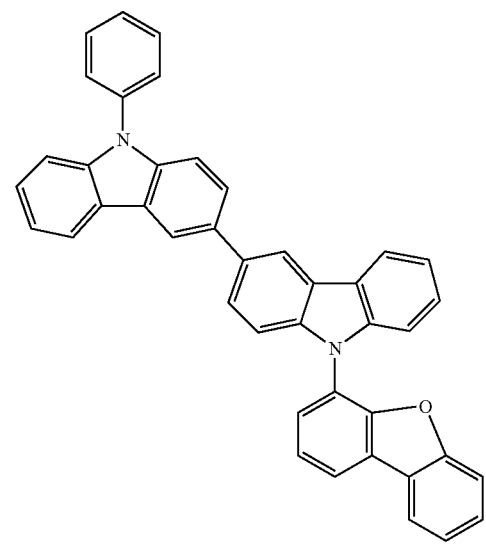

Compound 7
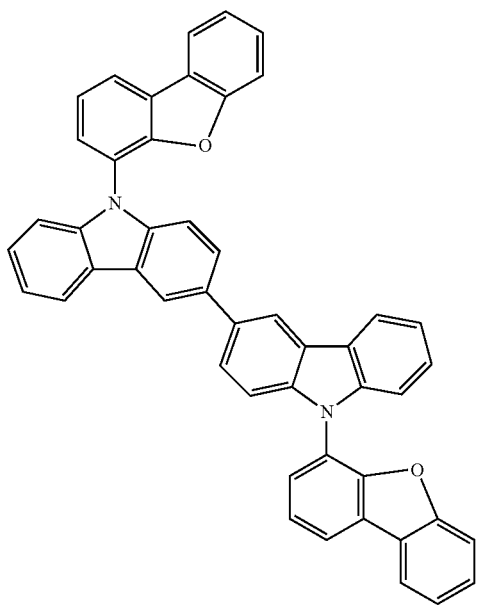
Compound 8
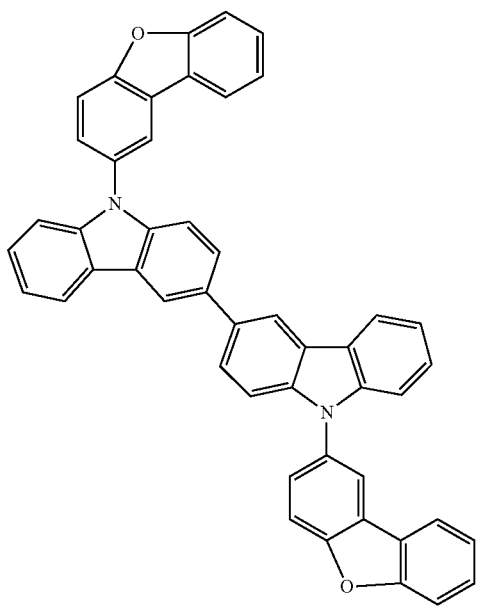
Compound 9
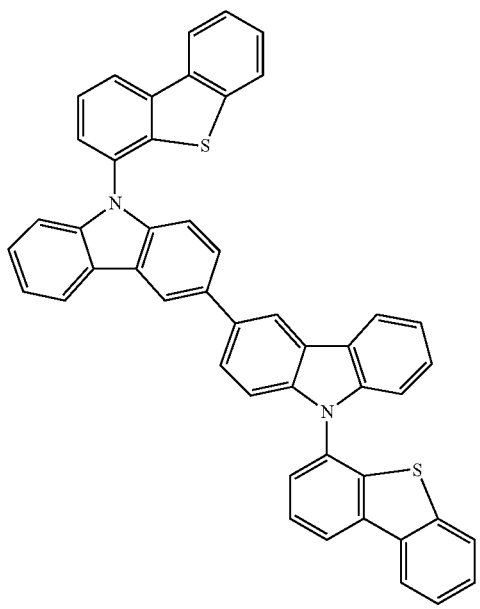
Compound 10
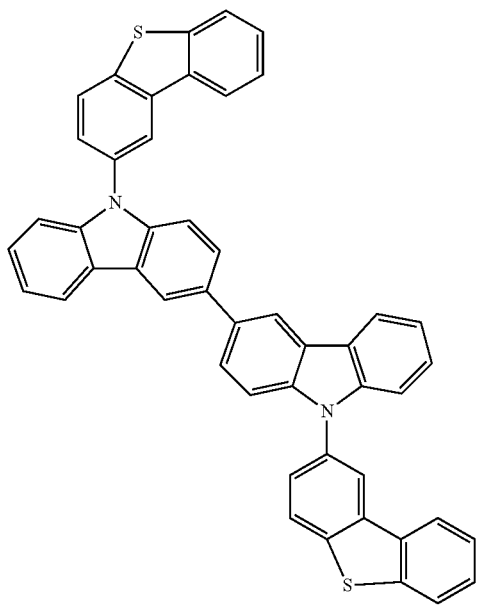

Compound 11
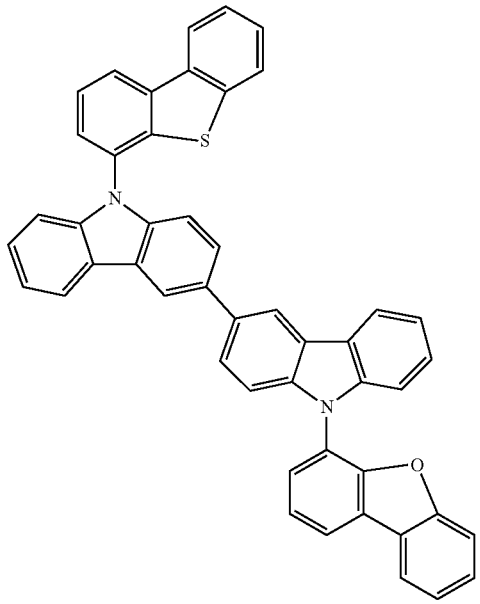
Compound 12
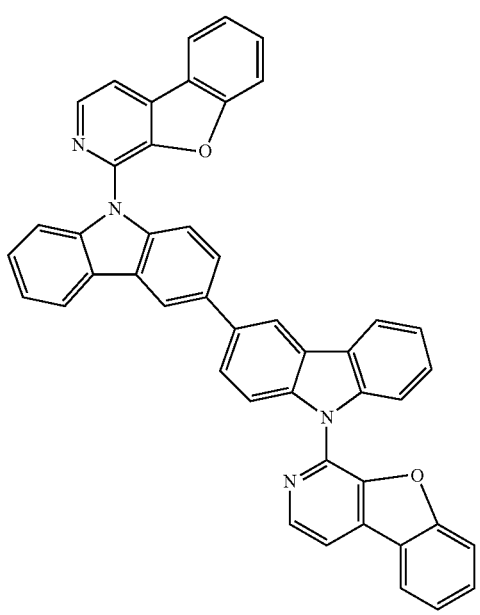
Compound 13
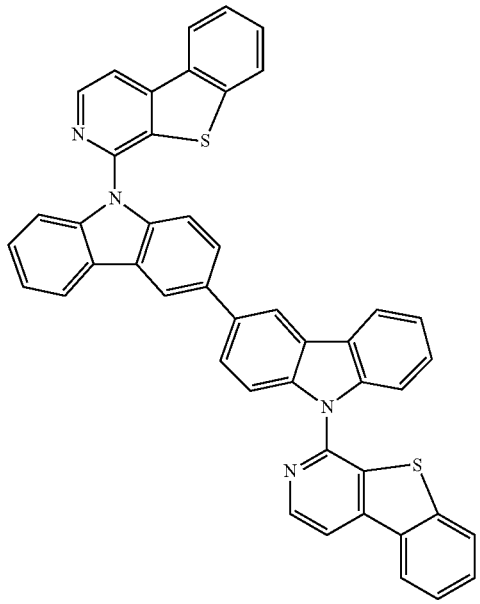
Compound 14
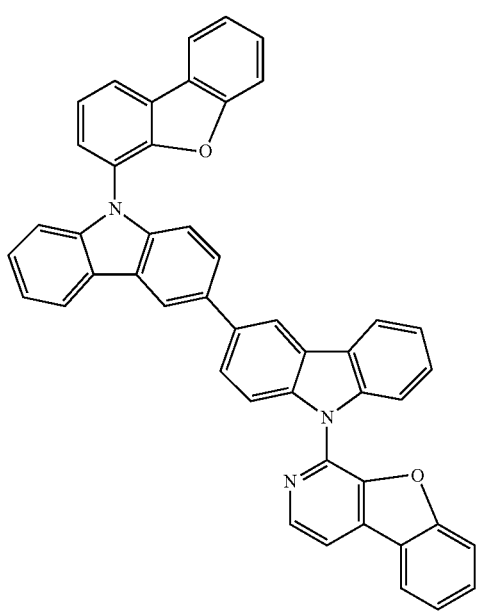

Compound 15

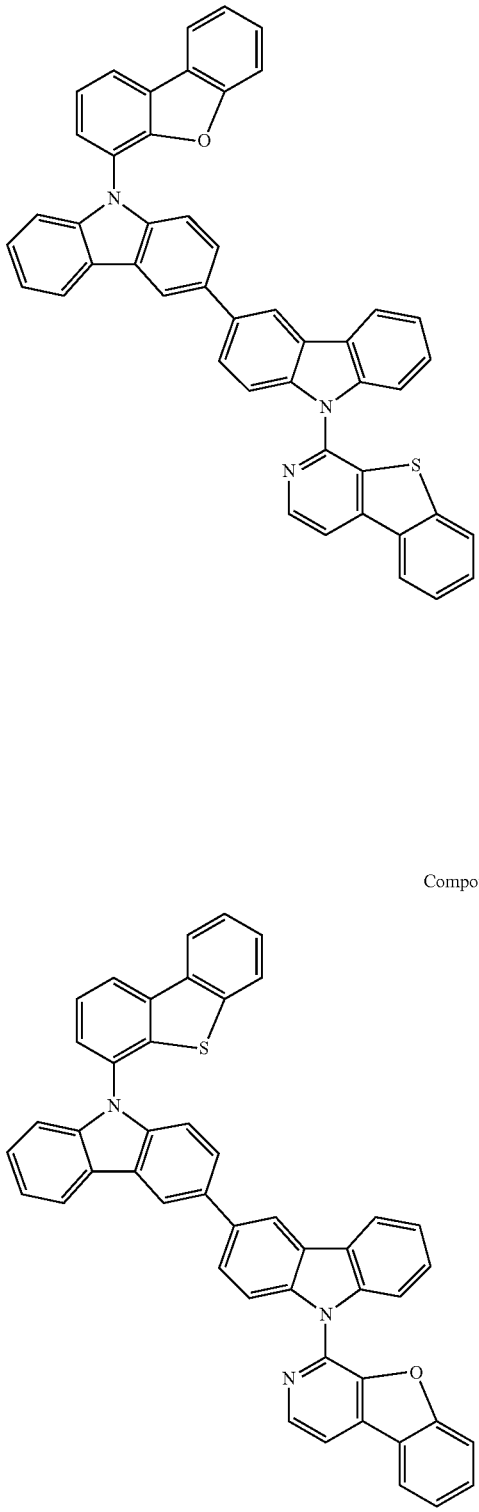

Compound 16

Compound 17

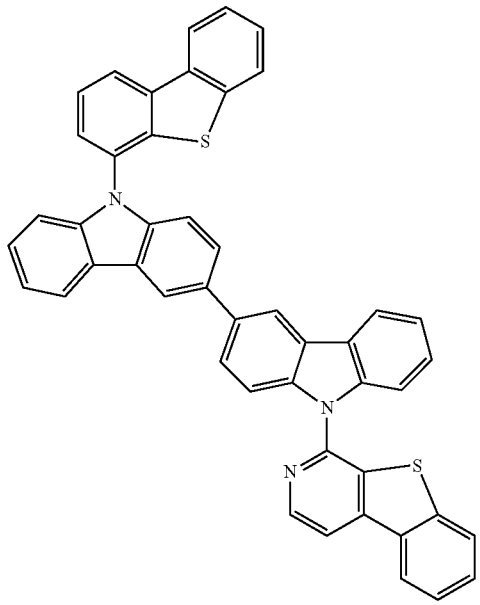

A first device comprising an organic light emitting device is also provided. The device further comprises an anode; a cathode; and an organic layer, disposed between the anode and the cathode. The organic layer comprises a compound comprising a bicarbazole, wherein the compound has the formula:

Formula I

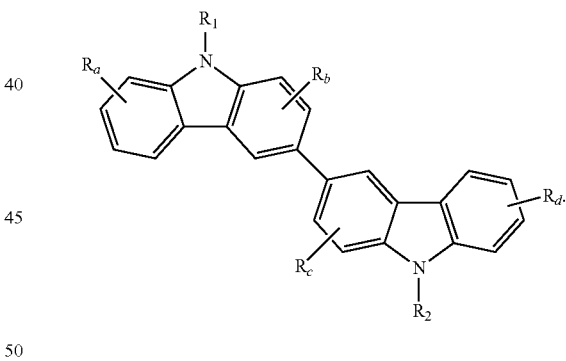

$R_a$, $R_b$, $R_c$, and $R_d$ may represent mono, di, tri, or tetra substitutions. $R_a$, $R_b$, $R_c$, $R_d$, $R_1$, and $R_2$ are independently selected from the group consisting of hydrogen, alkyl, alkoxy, amino, alkenyl, alkynyl, aryl and heteroaryl. Preferably, $R_1$ and $R_2$ are independently selected from aryl and heteroaryl. At least one of $R_1$ and $R_2$ has the formula:

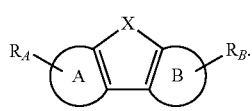

A and B are independently 5 or 6 membered carbocyclic or heterocyclic rings. Preferably, A and B are independently selected from phenyl and pyridine. $R_A$ and $R_B$ are independently selected from the group consisting of hydrogen, alkyl, alkoxy, amino, alkenyl, alkynyl, aryl and heteroaryl. X is S, O or Se.

In one aspect, only one of $R_1$ and $R_2$ has the formula:

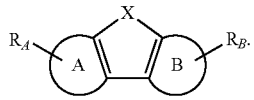

In another aspect, both $R_1$ and $R_2$ have the formula:

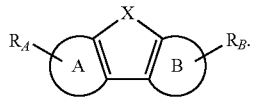

In one aspect, at least one of $R_1$ and $R_2$ has the formula:

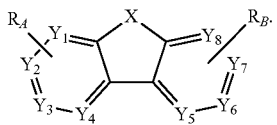

$R_A$ and $R_B$ may represent mono, di, tri, or tetra substitutions. $R_A$ and $R_B$ are independently selected from the group consisting of hydrogen, alkyl, alkoxy, amino, alkenyl, alkynyl, aryl and heteroaryl. $Y_1, Y_2, Y_3, Y_4, Y_5, Y_6, Y_7$, and $Y_8$ are independently selected from nitrogen and carbon.

In one aspect, $R_1$ and $R_2$ are independently selected from the group consisting of:

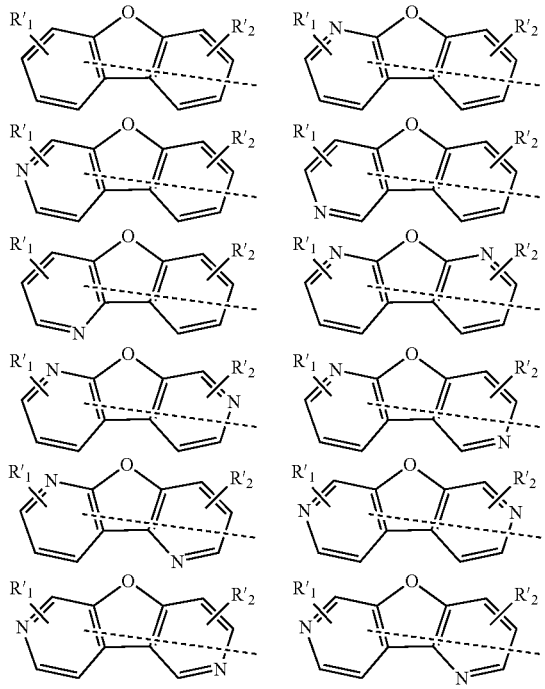

-continued

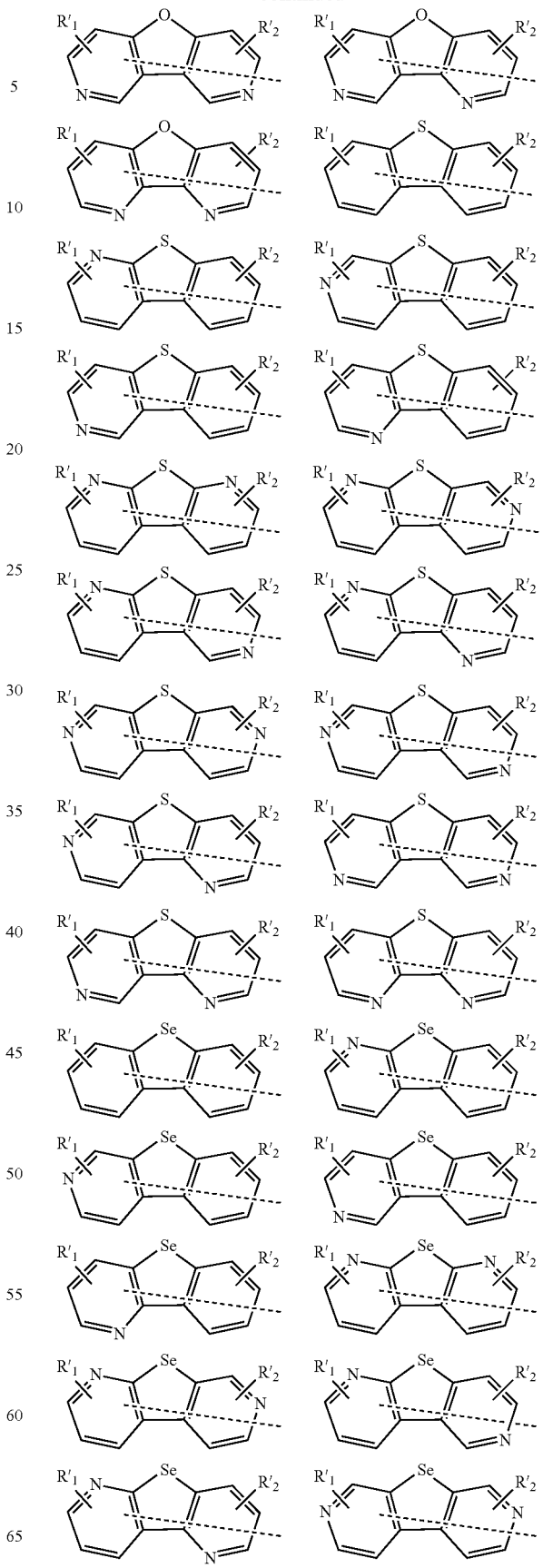

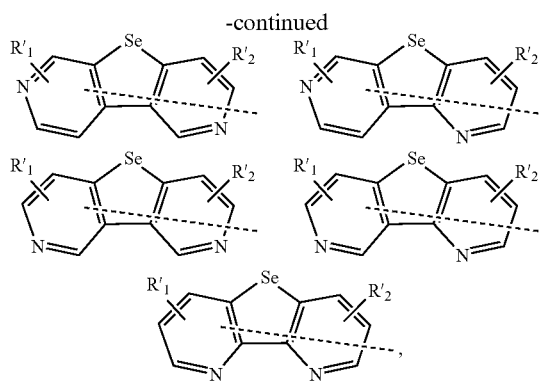

R'₁ and R'₂ are independently selected from the group consisting of hydrogen, alkyl, alkoxy, amino, alkenyl, alkynyl, aryl and heteroaryl.

In another aspect, the device comprises a compound having the formula:

Formula II

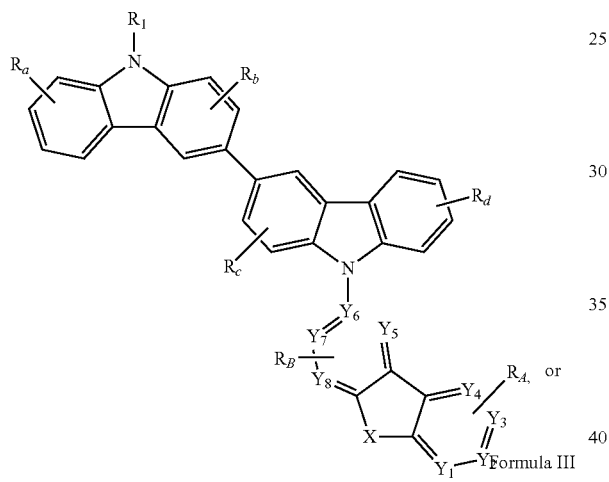

Formula III

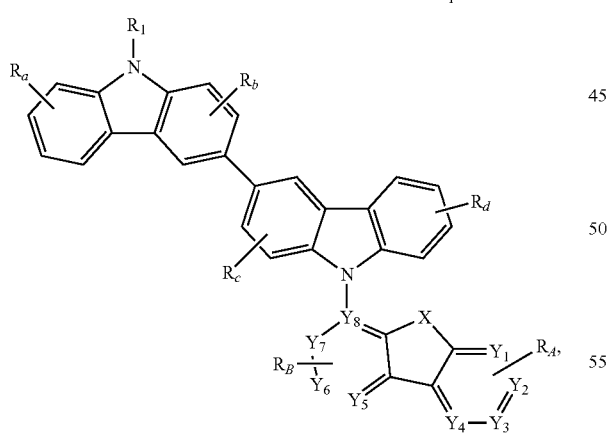

$R_A$ and $R_B$ may represent mono, di, tri, or tetra substitutions. $R_A$ and $R_B$ are independently selected from the group consisting of hydrogen, alkyl, alkoxy, amino, alkenyl, alkynyl, aryl and heteroaryl. $Y_1, Y_2, Y_3, Y_4, Y_5, Y_6, Y_7,$ and $Y_8$ are independently selected from nitrogen and carbon.

Specific examples of devices containing compounds comprising bicarbazole are also provided. In particular, the compound is selected from the group consisting of:

Compound 1

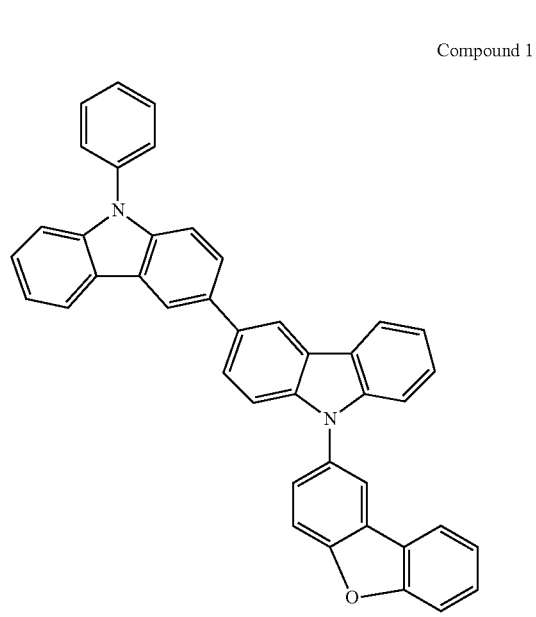

Compound 2

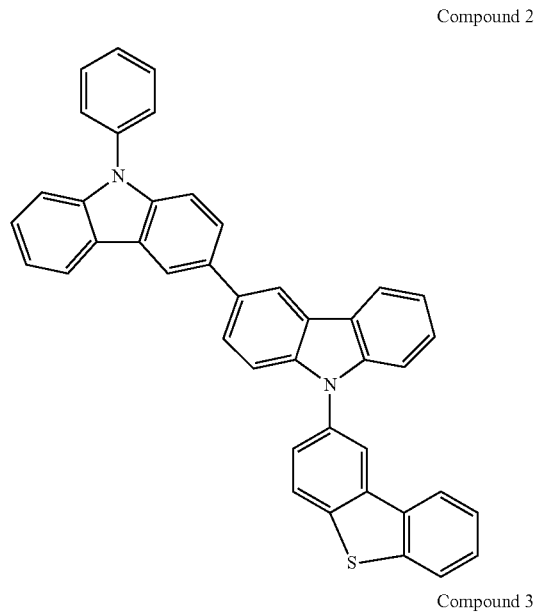

Compound 3

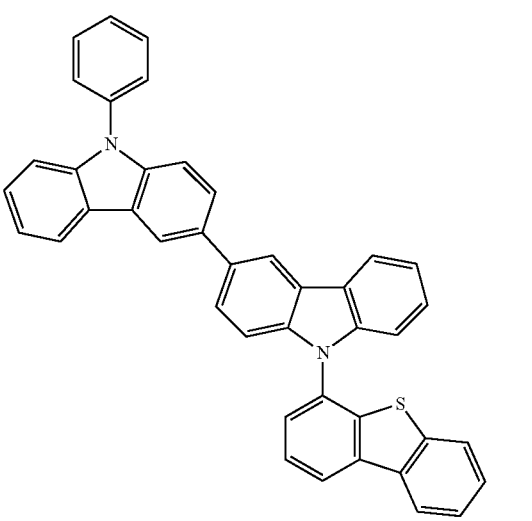

Compound 4
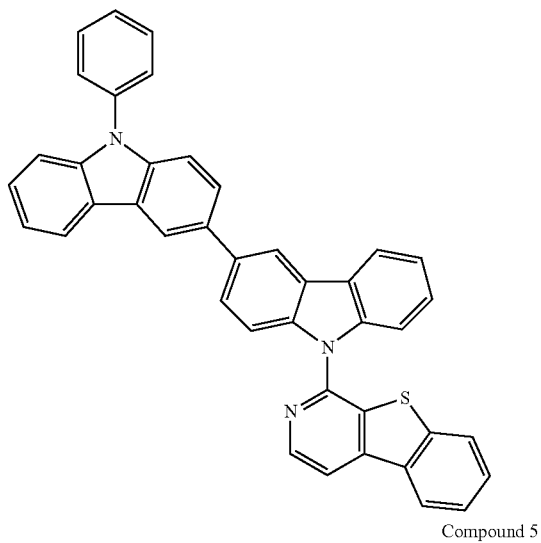
Compound 5
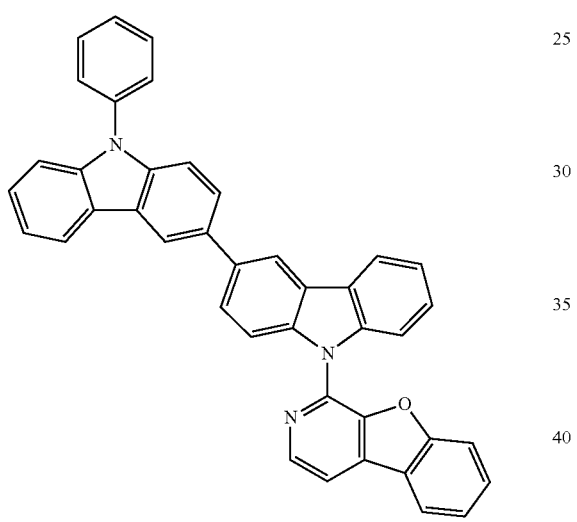
Compound 6
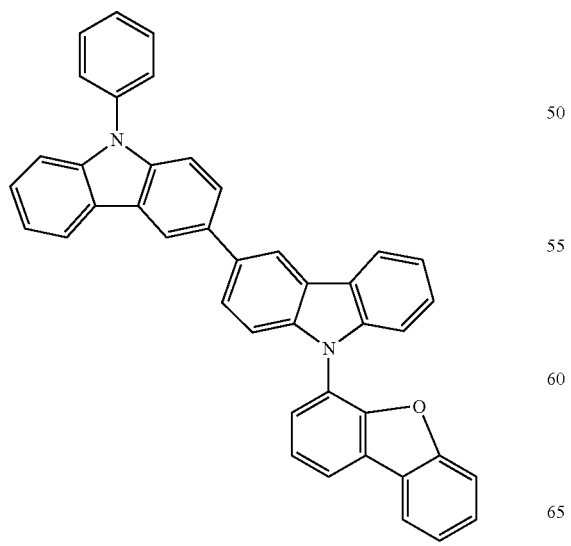
Compound 7
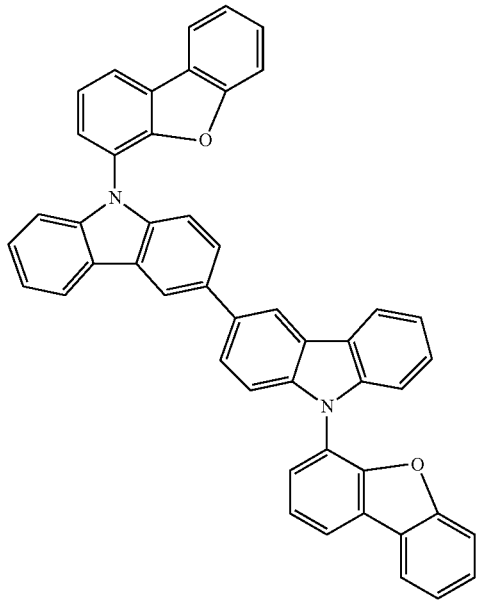
Compound 8
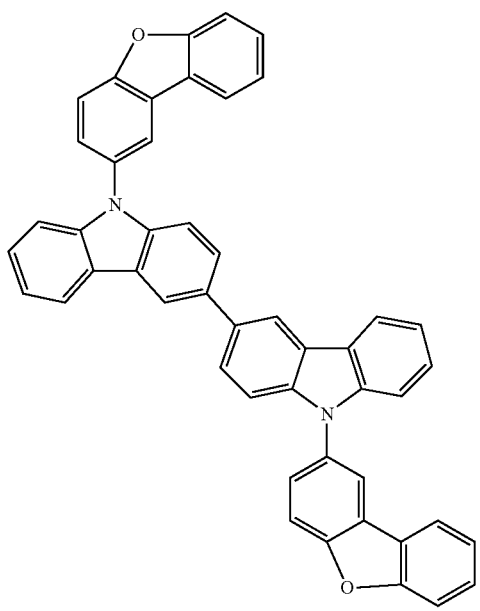

Compound 9
Compound 10
Compound 11
Compound 12
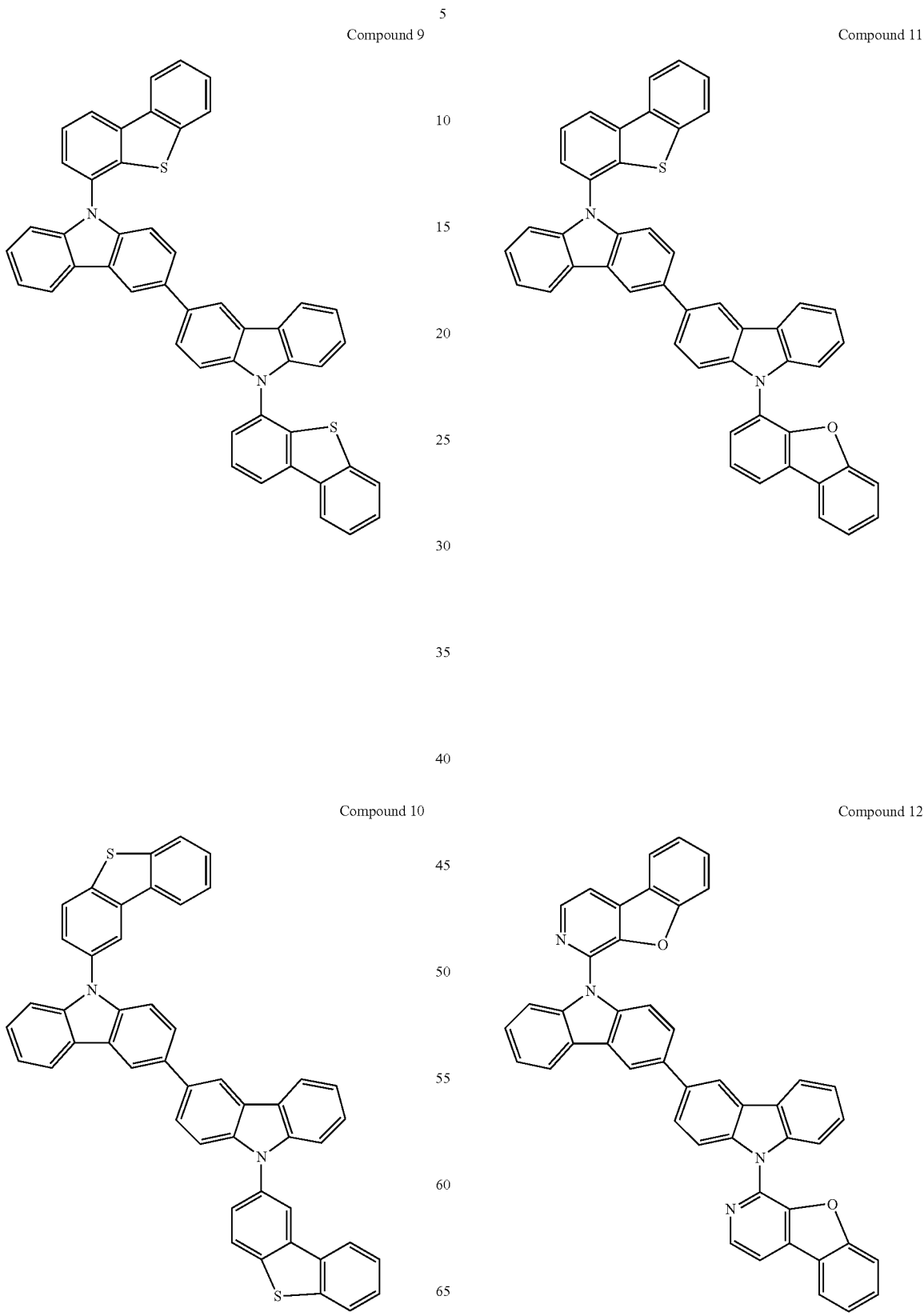

Compound 13
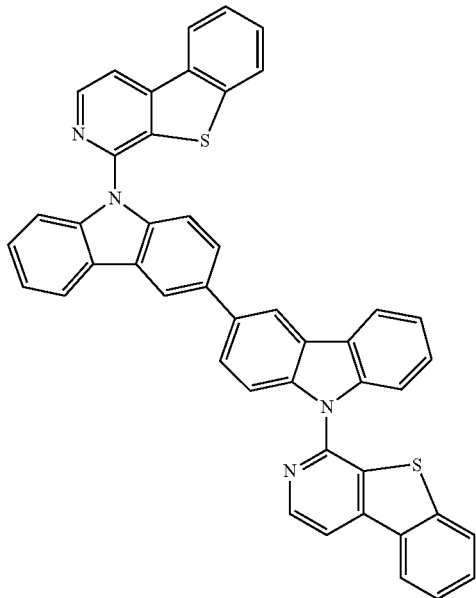
Compound 14
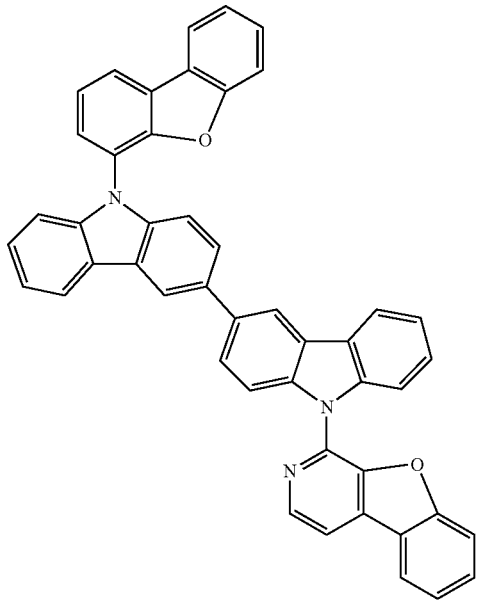
Compound 15
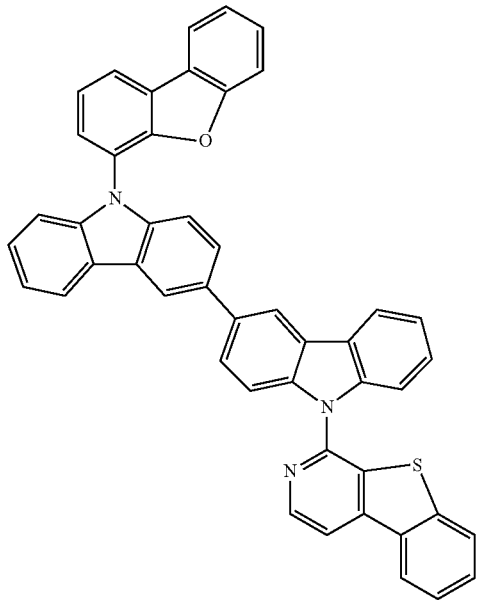
Compound 16
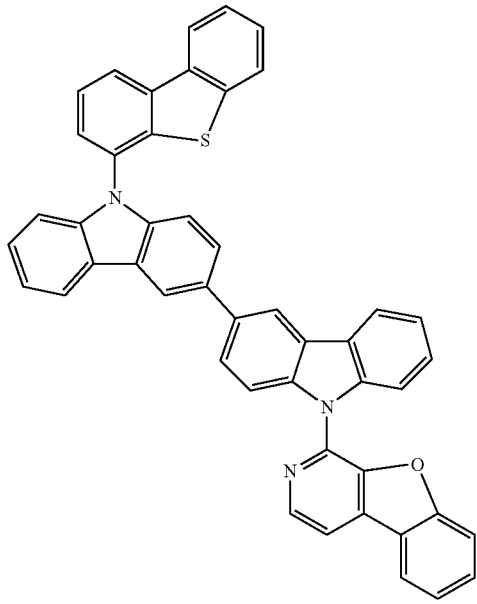

Compound 17

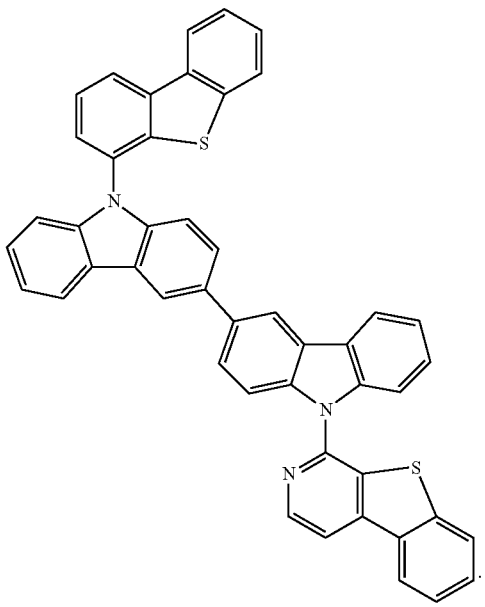

In one aspect, the organic layer is a blocking layer and the compound having Formula I is a blocking material.

In another aspect, the organic layer is an emissive layer and the compound having Formula I is a host. In yet another aspect, the emissive layer further comprises a phosphorescent emissive dopant having the formula:

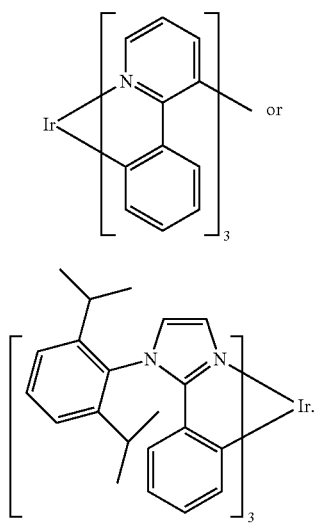

In one aspect, the first device is a consumer product. In another aspect, the first device is an organic light emitting device.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed below.

HIL/HTL:

A hole injecting/transporting material to be used in the present invention is not particularly limited, and any Compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

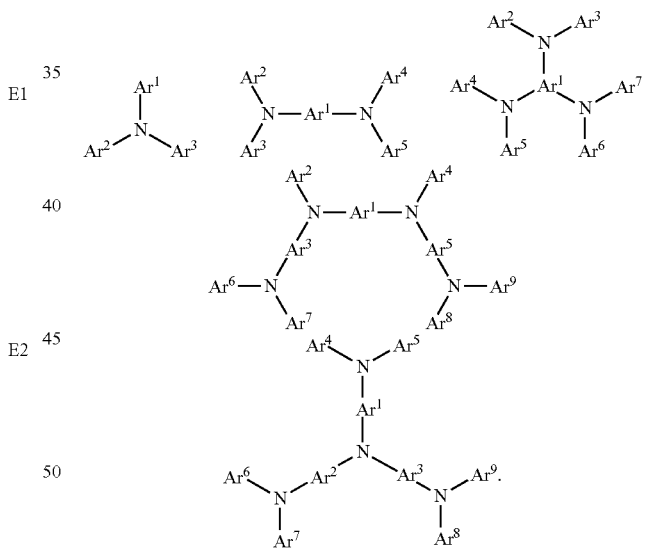

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, alkyl, alkoxy, amino, alkenyl, alkynyl, arylalkyl, heteroalkyl, aryl and heteroaryl.

In one aspect, $Ar^1$ to $Ar^9$ is independently selected from the group consisting of:

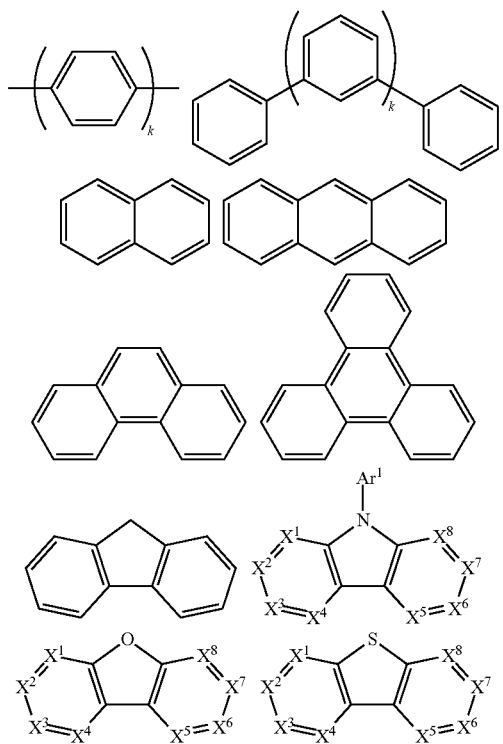

k is an integer from 1 to 20; $X^1$ to $X^8$ is CH or N; $Ar^1$ has the same group defined above.

Examples of metal complexes used in HIL or HTL include, but not limit to the following general formula:

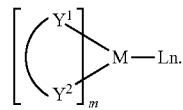

M is a metal, having an atomic weight greater than 40; $(Y^1—Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1—Y^2)$ is a 2-phenylpyridine derivative.
In another aspect, $(Y^1—Y^2)$ is a carbene ligand.
In another aspect, M is selected from Ir, Pt, Os, and Zn.
In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

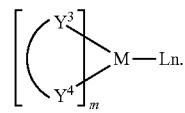

M is a metal; $(Y^3—Y^4)$ is a bindentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

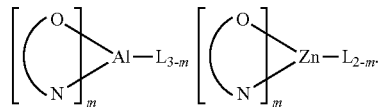

(O—N) is a bidentate ligand, having metal coordinated to atoms O and N.

In another aspect, M is selected from Ir and Pt.
In a further aspect, $(Y^3—Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, alkyl, alkoxy, amino, alkenyl, alkynyl, arylalkyl, heteroalkyl, aryl and heteroaryl.

In one aspect, host compound contains at least one of the following groups in the molecule:

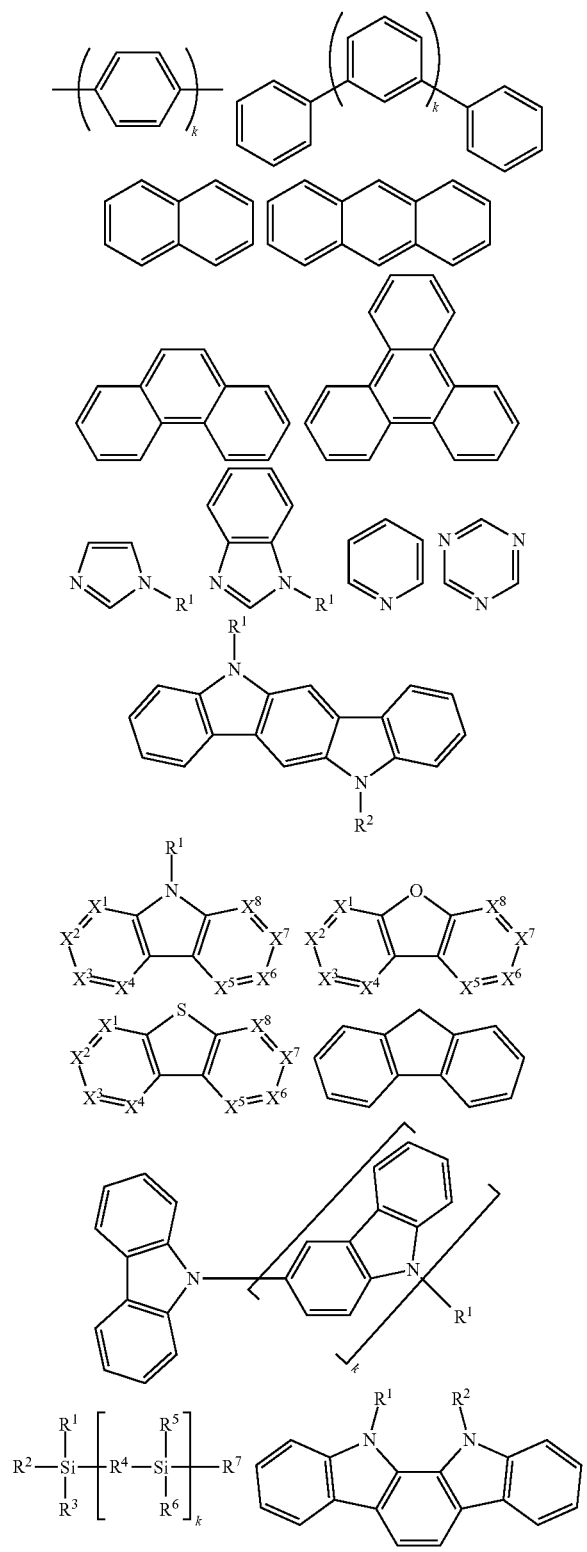

$R^1$ to $R^7$ is independently selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

k is an integer from 0 to 20.

$X^1$ to $X^8$ is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

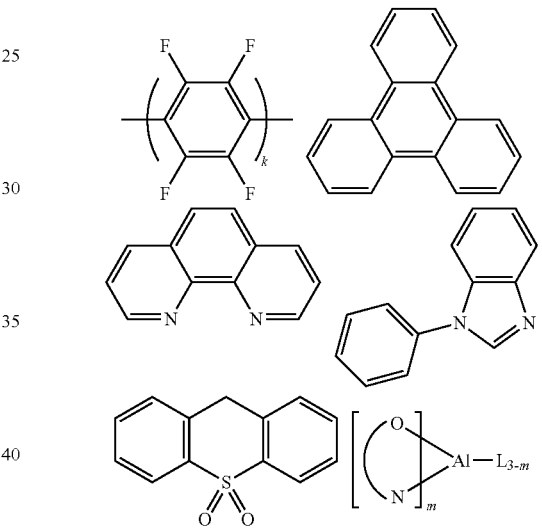

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

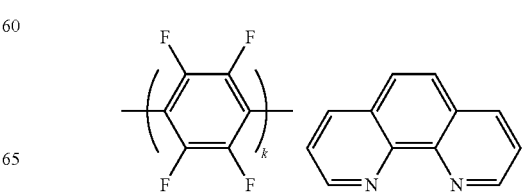

-continued

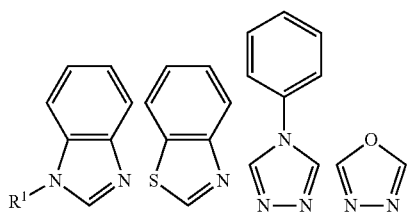

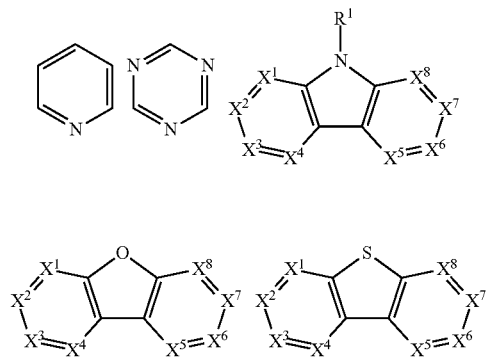

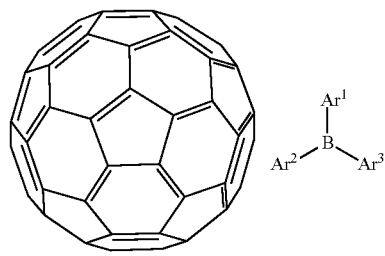

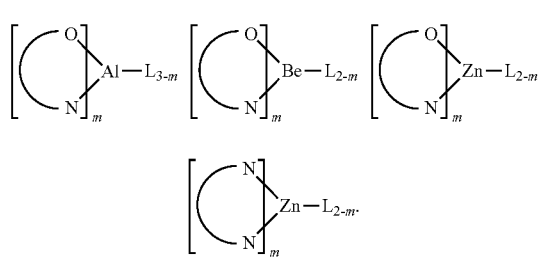

$R^1$ is selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from CH or N.

In another aspect, the metal complexes used in ETL contains, but not limit to the following general formula:

(O—N) or (N—N) is a bidentate ligand, having metal coordinated to atoms O, N or N, N; L is an ancillary ligand; m is an integer value from 1 to the maximum number of ligands that may be attached to the metal.

EXPERIMENTAL

Compound Examples

Example 1

Synthesis of Compound 1

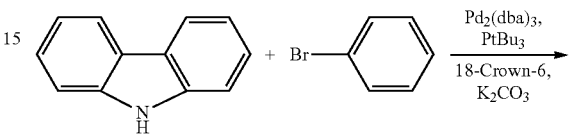

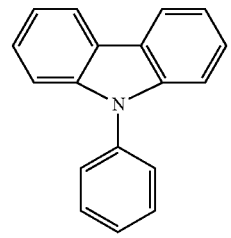

Synthesis of 9-phenylcarbazole. $Pd_2(dba)_3$ (1.095 g, 1.196 mmol) and tri-tert-butylphosphine (4.78 ml, 4.78 mmol, 1.0 M in toluene) were mixed in 400 mL of xylene. The mixture was stirred under $N_2$ for 20 min. 9H-carbazole (20 g, 120 mmol), bromobenzene (28.2 g, 179 mmol), 18-Crown-6 (3.16 g, 11.96 mmol), and potassium carbonate (24.80 g, 179 mmol) were then added in sequence, and the mixture was heated to reflux under $N_2$ for 18 h. The xylene solution was decanted. The solvent was evaporated and residue was purified by vacuum distillation. 22.3 g (97% yield) of product was obtained after purification.

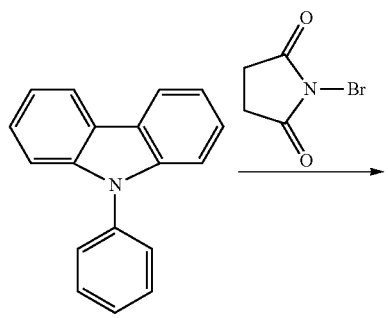

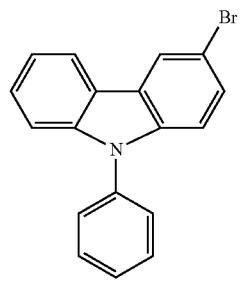

Synthesis of 3-bromo-9-phenylcarbazole. NBS (19.31 g, 109 mmol) in DMF was added to 9-phenyl-9H-carbazole (24 g, 99 mmol) in 200 mL at 0° C. dropwise. The reaction was monitored by HPLC. The reaction was quenched by adding 500 mL of water after 2 h. After stirring at room temperature for 24 h, the clear solution was decanted and solid residue was dissolved in dichloromethane and washed with water and LiCl solution. The solution was dried with MgSO₄ and the solvent was evaporated. The residue was used for the next step without further purification. The product contains starting material, monobromo, and dibromo. 31 g of product was obtained.

mL at 0° C. dropwise. The reaction was monitored by HPLC. After 2 h, HPLC indicated 76% of desired product and 6% of dibrominated compound. The reaction was quenched by adding 500 mL of ice water. The internal temperature was controlled to be lower than 10° C. The precipitate formed was collected by filtration. The solid was stirred in 400 mL of warm methanol. (~40° C.). The solid was collected by filtration. The solid was dissolved in 150 mL of DCM. 200 mL of methanol was added. The DCM was boiled off. The solvent level was down to 150 mL. The slurry was stirred at room temperature overnight. The solid was collected by filtration. 9 g (51% yield) of solid was collected.

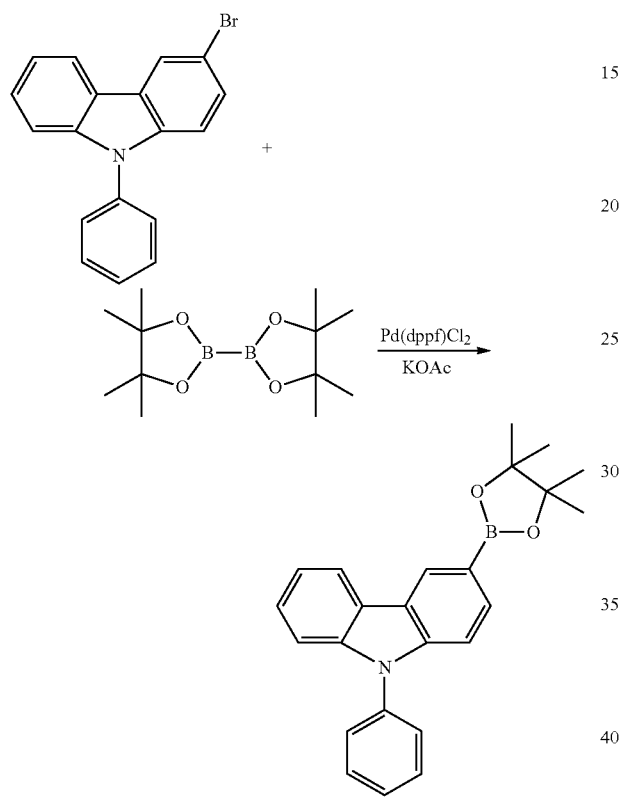

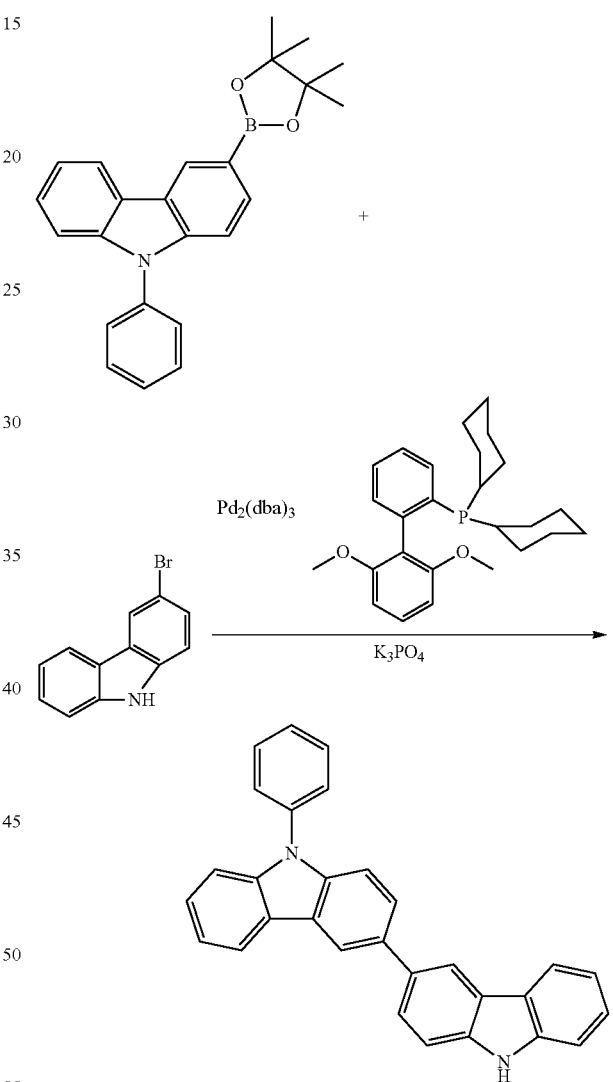

Synthesis of 9-phenyl-3-(4,4,5,5-tetramethyl-1,3,2-dioxaborolan-2-yl)-9H-carbazole. 3-bromo-9-phenyl-9H-carbazole (30 g, 93 mmol), 4,4,4',4',5,5,5',5'-octamethyl-2,2'-bi(1,3,2-dioxaborolane) (47.3 g, 186 mmol), and potassium acetate (22.85 g, 233 mmol) were added to 400 mL of dioxane. Nitrogen was bubbled to the solution for 20 min. Pd(dppf)Cl₂ (2.281 g, 2.79 mmol) was added and the reaction mixture was heated up to 80° C. for 6 h. The reaction was monitored by TLC. After cooled to room temperature, the reaction was filtered through a silica gel plug. The diboron was removed by vacuum distillation at 160° C. The residue was coated on celite and purified by column using 2% of ethyl acetate and hexanes as solvent. 16.5 g of product was obtained after purification.

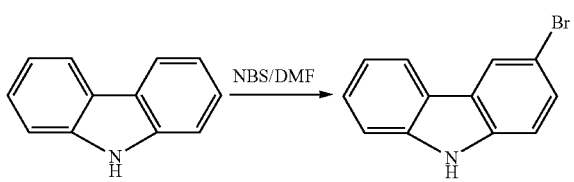

Synthesis of 3-bromocarbazole. NBS (12.77 g, 71.8 mmol) in DMF was added to 9H-carbazole (12 g, 71.8 mmol) in 200

Synthesis of 9-phenyl-9H,9'H-3,3'-bicarbazole. A mixture of 9-phenyl-3-(4,4,5,5-tetramethyl-1,3,2-dioxaborolan-2-yl)-9H-carbazole (12 g, 32.5 mmol), 3-bromo-9H-carbazole (6.66 g, 27.1 mmol), and potassium phosphate (34.5 g, 162 mmol) in 500 mL of toluene and 50 mL of H₂O was bubbled with N₂ for 20 min. Dicyclohexyl(2',6'-dimethoxybiphenyl-2-yl)phosphine (0.445 g, 1.083 mmol) and Pd2(dba)3 (0.248 g, 0.271 mmol) were then added, and the mixture was heated to reflux under N₂ for 5 h. TLC indicated the reaction was done. The reaction was extracted with dichloromethane and washed with brine and dried with magnesium sulfate. The solution was heated up to boil. Hexane was added. The dichloromethane was boiled off and hexanes volume reached about 1200 mL. Precipitate formed during boiling off dichloromethane. The solution was cooled to room temperature and stirred overnight. The precipitate was filtered and dissolved in THF and ran a short silica gel plug. After dried under vacuum at 60° C., 9.6 g (87%) of product was obtained.

Celite and purified by column chromatography 3.7 g of product was obtained after column.

Example 2

Synthesis of Compound 2

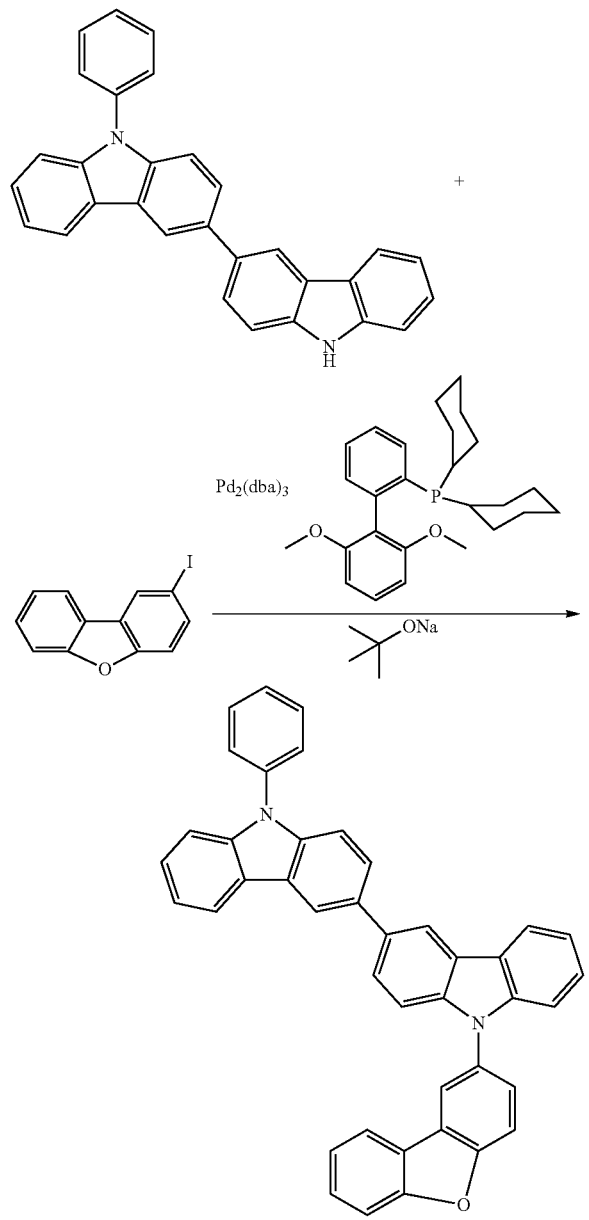

Compound 1

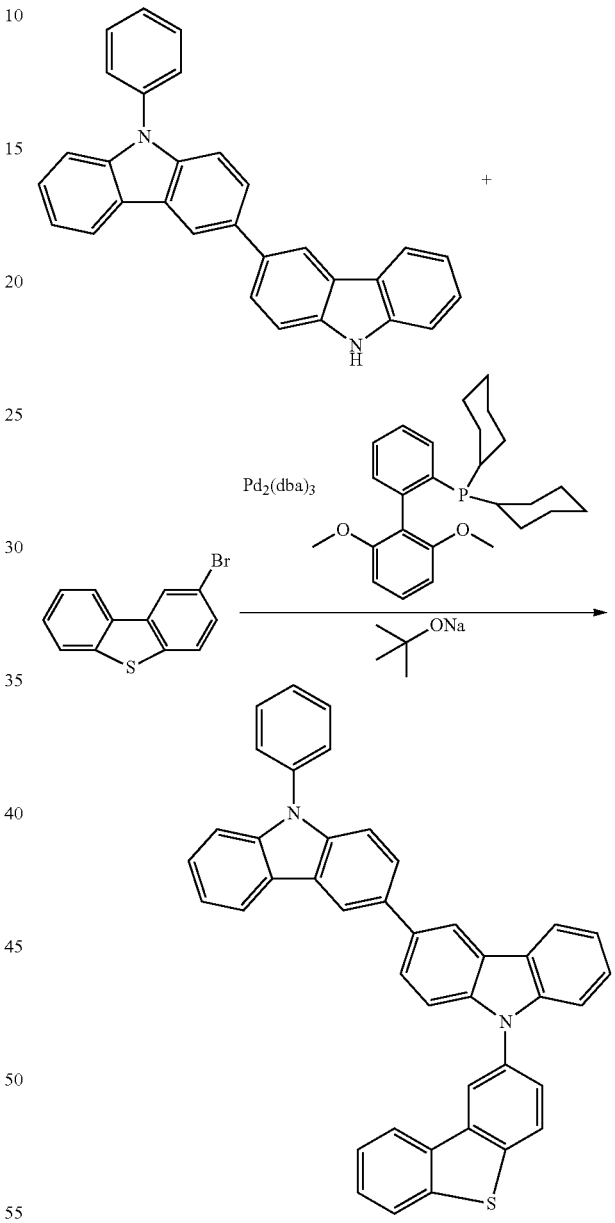

Compound 2

Synthesis of Compound 1. A mixture of 2-iododibenzo[b,d]furan (2.59 g, 8.81 mmol), 9-phenyl-9H,9'H-3,3'-bicarbazole (3 g. 7.34 mmol), and sodium t-butoxide (1.764 g, 18.36 mmol) in 200 mL of xylene was bubbled with $N_2$ for 20 min. Dicyclohexyl(2',6'-dimethoxybiphenyl-2-yl)phosphine (0.121 g, 0.294 mmol) and $Pd_2(dba)_3$ (0.067 g, 0.073 mmol) were then added, and the mixture was heated to reflux under $N_2$ for 24 h. The mixture was cooled and filtered through Celite. After solvent evaporation, the residue was coated on Synthesis of Compound 2. A mixture of 2-bromodibenzo [b,d]thiophene (3.22 g, 12.24 mmol), 9-phenyl-9H-9'H-3,3'-bicarbazole (2.5 g, 6.12 mmol), and sodium t-butoxide (1.764 g, 18.36 mmol) in 100 mL of xylene was bubbled with $N_2$ for 20 min. $Pd_2(dba)_3$ (0.056 g, 0.061 mmol) and dicyclohexyl (2',6'-dimethoxybiphenyl-2-yl)phosphine (0.100 g, 0.245 mmol) were then added, and mixture was then bubbled with nitrogen for another 20 min. The reaction mixture was refluxed under $N_2$ for 24 h. The mixture was cooled and filtered through Celite. After solvent evaporation, the residue was coated on Celite and purified by column chromatography using up to 50% dichloromethane in hexane as solvent. 9-(dibenzo[b,d]thiophen-2-yl)-9'-phenyl-9H,9'H-3,3'-bicarbazole (2.1 g, 3.55 mmol, 58.1% yield) was obtained.

Example 3

Synthesis of Compound 3

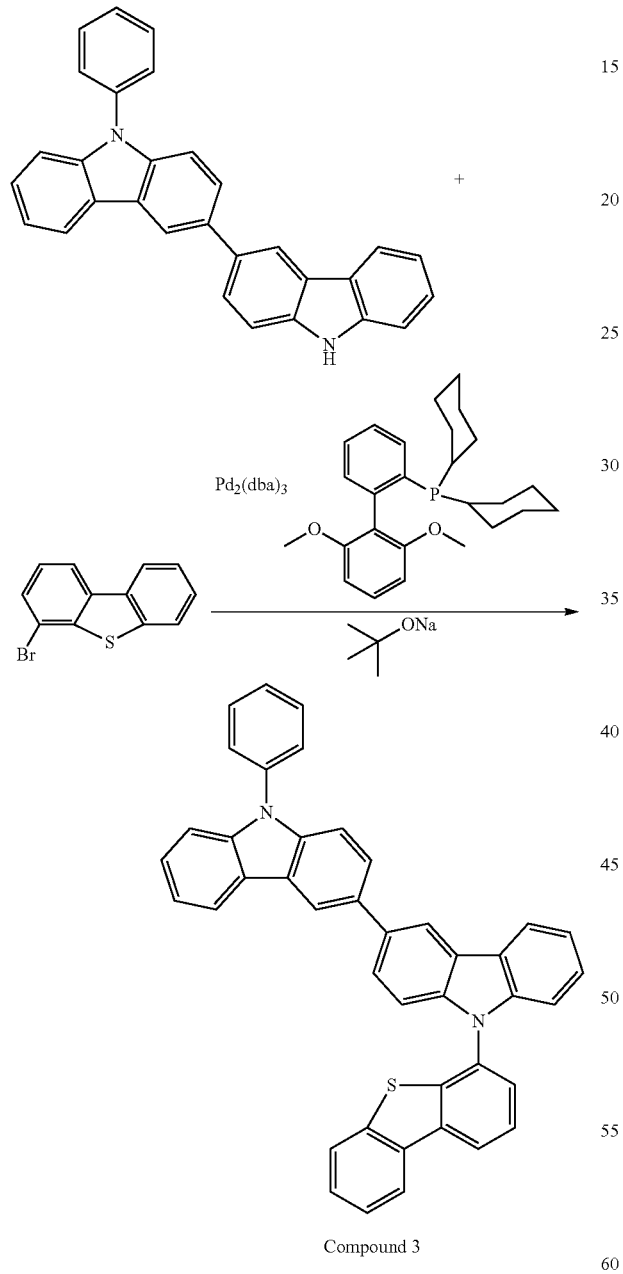

Compound 3

Synthesis of Compound 3. A mixture of 4-bromodibenzo[b,d]thiophene (2.061 g, 7.83 mmol), 9-phenyl-9H,9'H-3,3'-bicarbazole (2 g, 4.90 mmol), and sodium t-butoxide (1.412 g, 14.69 mmol) in 200 mL of xylene was bubbled with $N_2$ for 20 min. $Pd_2(dba)_3$ (0.045 g, 0.049 mmol) and dicyclohexyl (2',6'-dimethoxybiphenyl-2-yl)phosphine (0.080 g, 0.196 mmol) were added and bubbled with nitrogen for another 20 min, then the mixture was heated to reflux under $N_2$ for 24 h. The mixture was cooled and filtered through Celite. After solvent evaporation, the residue was coated on Celite and purified by column chromatography using 2:3 dichloromethane and hexanes as solvent. 9-(dibenzo[b,d]thiophen-4-yl)-9'-phenyl-9H,9'H-3,3'-bicarbazole (2.2 g. 3.72 mmol, 76% yield) was obtained. The product was further purified by recrystallization with dichloromethane and hexane.

Example 4

Synthesis of Compound 4

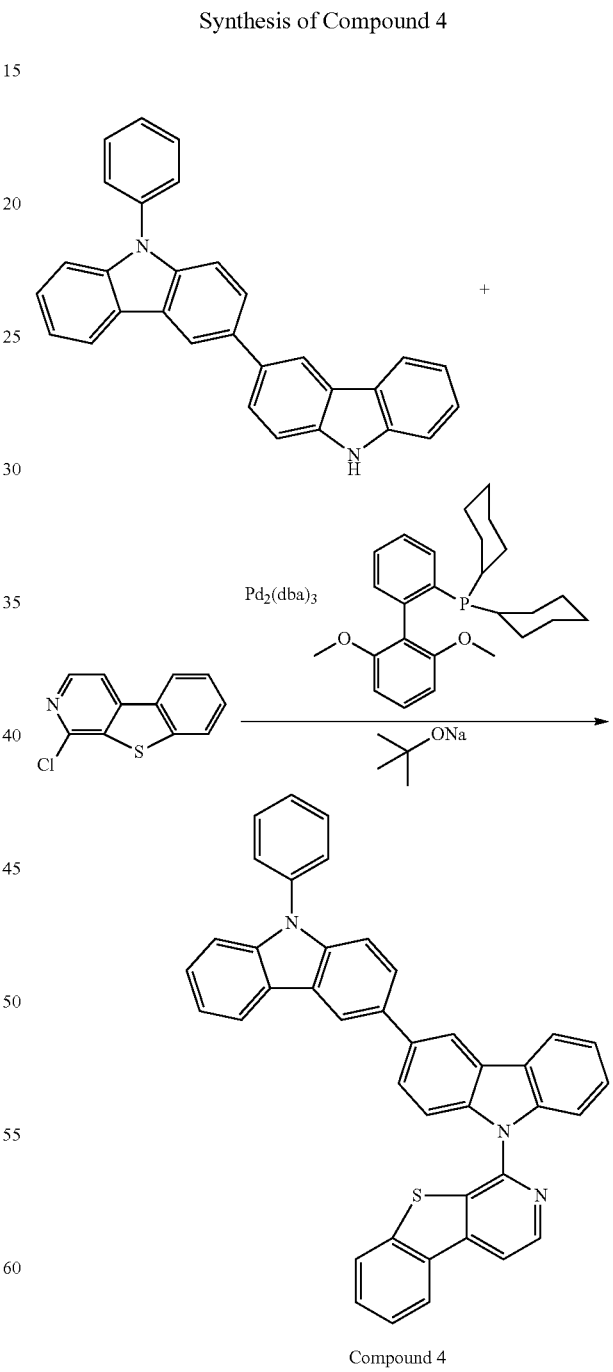

Compound 4

Synthesis of Compound 4. A mixture of 4-chloro-3-azadibenzothiophene (2.58 g, 11.75 mmol), 9-phenyl-9H,9'H-3, 3'-bicarbazole (4 g, 9.79 mmol), and sodium t-butoxide (2.353 g, 24.48 mmol) in 200 mL of xylene was bubbled with N₂ for 20 min. Dicyclohexyl(2',6'-dimethoxybiphenyl-2-yl)phosphine (0.161 g, 0.392 mmol) and Pd₂(dba)₃ (0.090 g, 0.098 mmol) were then added, and the mixture was heated to reflux under N₂ for 14 h. The mixture was cooled and filtered through Celite plug. After solvent evaporation, the residue was coated on Celite and purified by column chromatography with 1:1 dichloromethane and hexanes to 2:1 dichloromethane and hexanes. 3.8 g product was obtained after column.

Example 5

Synthesis of Compound 5

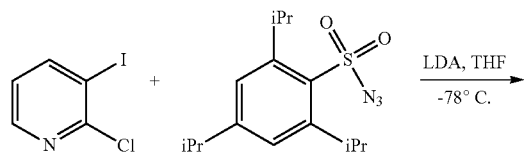

Synthesis of 3-azido-2-chloro-4-iodopyridine. 2-chloro-3-iodopyridine (8 g, 33 mmol) was added to 300 mL THF under inert environment and the reaction mixture was cooled to −78° C. Lithium diisopropylamide (2M solution in THF, 17 ml, 33 mmol) was added dropwise to the reaction mixture and after complete addition, THF solution stirred at −78° C. for 1 h. A solution of 2,4,6-triisopropylbenzenesulfonyl azide (15.5 g, 50 mmol) in 50 mL THF was then slowly added to the reaction mixture and was stirred for another 1 h at −78° C. Reaction flask was then slowly warmed up to room temperature. Reaction mixture was quenched with 10 mL saturated NH₄Cl solution. Most of the organic solvent was evaporated under vacuum. Crude product was partitioned between brine and ethyl acetate. Organic layer was isolated, dried over anhd. Na₂SO₄ and later purified by silica gel column chromatography using 2-10% ethylacetate/hexanes as eluent. 3-azido-2-chloro-4-iodopyridine (25 mmol, 7 g, 75% yield) was isolated as a light yellow color crystalline solid.

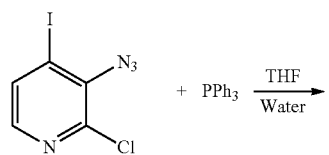

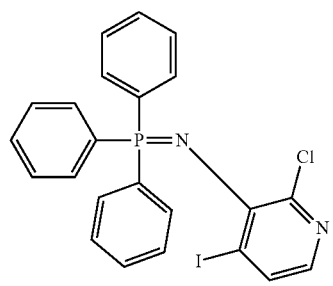

Synthesis of 2-chloro-4-iodo-N-(triphenylphosphoranylidene)pyridin-3-amine. 3-azido-2-chloro-4-iodopyridine (7 g, 25 mmol) and triphenylphosphine (8.5 g, 32 mmol) was stirred in 100 mL 1:1 mixture of THF and water until azide starting material disappears in TLC. After that most of the THF was removed under vacuum. Crude product was partitioned between brine and ethylacetate. Organic layer was isolated, dried over anhd. Na₂SO₄ and purified by silica gel column chromatography using 5-40% ethyl acetate and hexanes as eluent. 2-chloro-4-iodo-N-(triphenylphosphoranylidene)pyridin-3-amine (12 g, 23 mmol, 93% yield) was isolated as crystalline white solid.

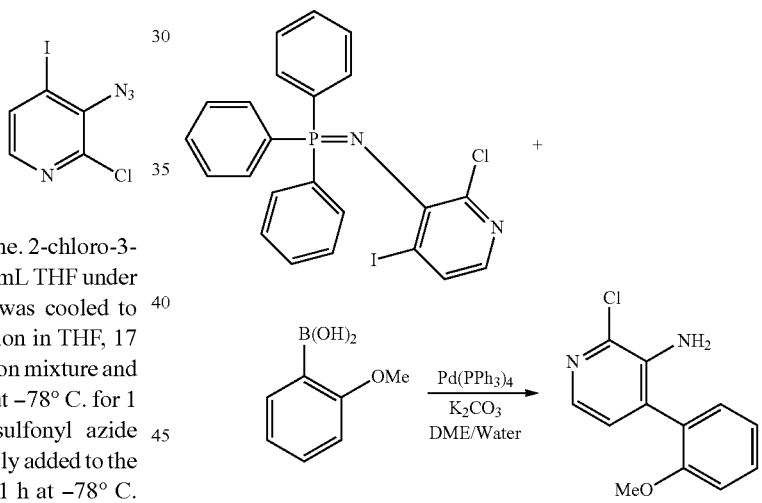

Synthesis of 2-chloro-4-(2-methoxyphenyl)pyridin-3-amine. 2-chloro-4-iodo-N-(triphenylphosphoranylidene)pyridin-3-amine (12 g, 23 mmol), (2-methoxyphenyl)boronic acid (4.25 g, 28 mmol), 2M potassium carbonate solution (46.6 ml, 93 mmol) were poured in 120 mL DME and degassed with bubbling nitrogen for 15 min. To the stirred solution was added tetrakisphosphine palladium(0) (1.35 g, 1.12 mmol) and reaction mixture was degassed for another 10 min. Reaction mixture was then refluxed for 48 h. Cooled reaction mixture was partitioned between ethyl acetate and brine. Organic layer was isolated, dried over anhd. Na₂SO₄ and purified by silica gel column chromatography using 5-30% ethyl acetate/hexanes as eluent. 2-chloro-4-(2-methoxyphenyl)pyridin-3-amine (4.3 g, 18 mmol, 78% yield) was isolated as liquid oil which turns into white crystals upon standing at room temperature.

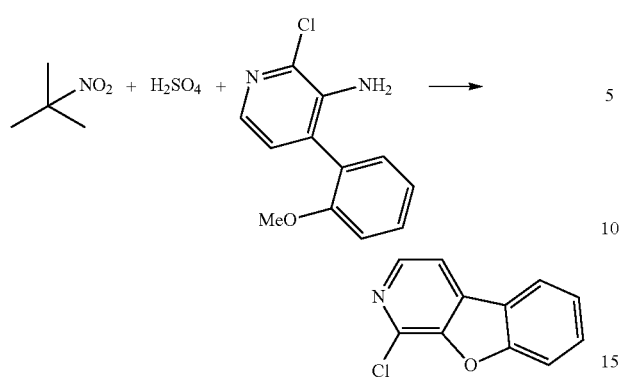

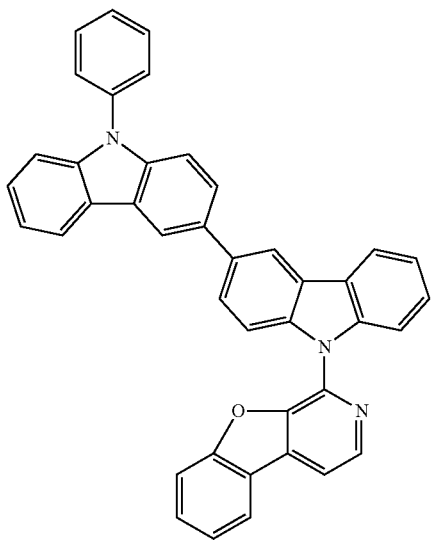

Compound 5

Synthesis of 1-chlorobenzofuro[2,3-c]pyridine. 2-chloro-4-(2-methoxyphenyl)pyridin-3-amine (4.3 g, 18 mmol) was dissolved in 91 mL glacial acetic acid and conc. sulfuric acid (0.503 ml, 18.11 mmol). 2-methyl-2-nitropropane (6.22 g, 54.3 mmol) was added dropwise to the reaction mixture at room temperature. Reaction mixture was stirred at 45° C. until the starting material disappears in GC. After complete reaction, most of the acetic acid was distilled out under vacuum and the crude was diluted with DCM. Organic residue was partitioned between DCM and $Na_2CO_3$ solution. Organic layer was isolated, washed with brine, dried over anhd. $Na_2SO_4$ and solvents were evaporated under vacuum. Crude product was purified by silica gel column chromatography using 10-30% ethyl acetate/hexanes as eluent. 1.5 g 1-chlorobenzofuro[2,3-c]pyridine was isolated as white solid in 41% yield.

Synthesis of Compound 5. A mixture of 1-chlorobenzofuro[2,3-c]pyridine (1.45 g, 7.12 mmol), 9-phenyl-9H,9'H-3,3'-bicarbazole (3.49 g, 8.55 mmol), and sodium 2-methylpropan-2-olate (1.711 g, 17.80 mmol) in 150 mL of xylene was bubbled with $N_2$ for 20 min. Dicyclohexyl(2',6'-dimethoxy-[1,1'-biphenyl]-2-yl)phosphine (0.117 g, 0.285 mmol) and $Pd_2(dba)_3$ (0.065 g, 0.071 mmol) were then added, and the mixture was heated to reflux under $N_2$ for 14 h. The mixture was cooled and filtered through Celite plug. After solvent evaporation, the residue was coated on Celite and purified by column chromatography with 1:1 dichloromethane and hexanes to 3:2 dichloromethane and hexanes. 4 g (98% yield) of product was obtained.

Example 6

Synthesis of Compound 9

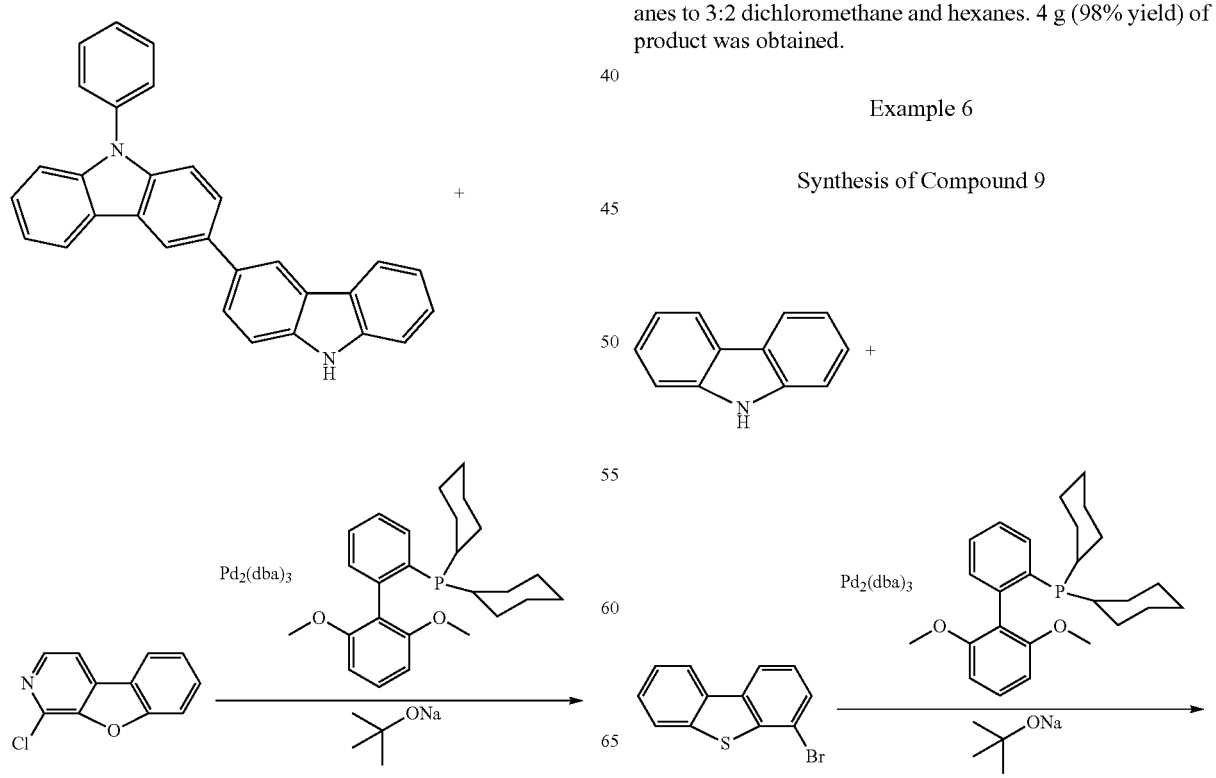

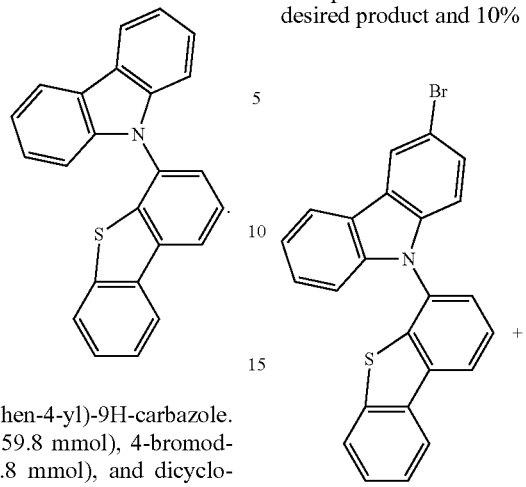

Synthesis of 9-(dibenzo[b,d]thiophen-4-yl)-9H-carbazole. A mixture of 9H-carbazole (10 g, 59.8 mmol), 4-bromodibenzo[b,d]thiophene (18.89 g, 71.8 mmol), and dicyclohexyl(2',6'-dimethoxy-[1,1'-biphenyl]-2-yl)phosphine (0.982 g, 2.392 mmol) in 200 mL of Xylene was bubbled with N₂ for 20 min. Pd₂dba₃ (0.548 g, 0.598 mmol) and sodium 2-methylpropan-2-olate (8.62 g, 90 mmol) were then added, and the mixture was heated to reflux under N₂ for 24 h. TLC indicated the reaction did not go to completion. 0.3 g of Pd₂(dba)₃ and 0.6 g of dicyclohexyl(2',6'-dimethoxy-[1,1'-biphenyl]-2-yl)phosphine was added. The reaction was continued to reflux. The reaction was monitored by GC. After another 24 h, there was still carbazole starting material remaining. Again, 0.3 g of Pd₂(dba)₃ and 0.6 g of dicyclohexyl(2',6'-dimethoxy-[1,1'-biphenyl]-2-yl)phosphine were added. The reaction was refluxed again for 24 h. The reaction was stopped and worked up for purification. Column was used for purification. (1:3 dichloromethane:hexanes) 10 g (47.8% yield) of product was obtained.

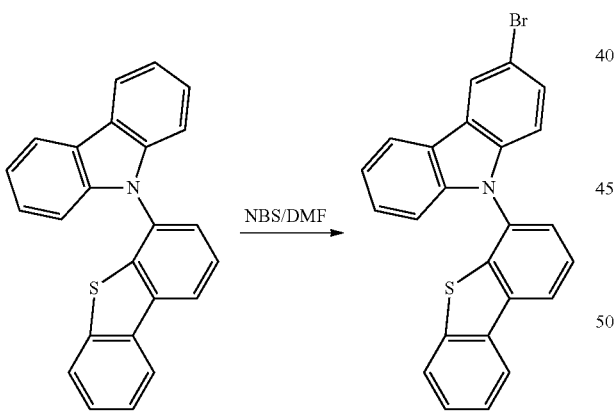

Synthesis of 3-bromo-9-(dibenzo[b,d]thiophen-4-yl)-9H-carbazole. 9-(dibenzo[b,d]thiophen-4-yl)-9H-carbazole (6 g, 17.17 mmol) was dissolved in 100 mL of DMF. The solution was cooled to 0° C. To the solution was added NBS (3.36 g, 18.89 mmol) in 20 mL of DMF dropwise. After stirring at this temperature for 1 h, HPLC indicated there was very little reaction. The reaction was warmed to room temperature and monitored by HPLC. After 24 h, 500 mL of water was added to the reaction and stirred at room temperature for 2 h. The white precipitate was filtered and washed with water. The solid was dissolved in DCM and washed with water and dried over MgSO₄. The residue was used directly for the next step.

The product contains 10% of starting material, 80% of desired product and 10% of dibrominated product.

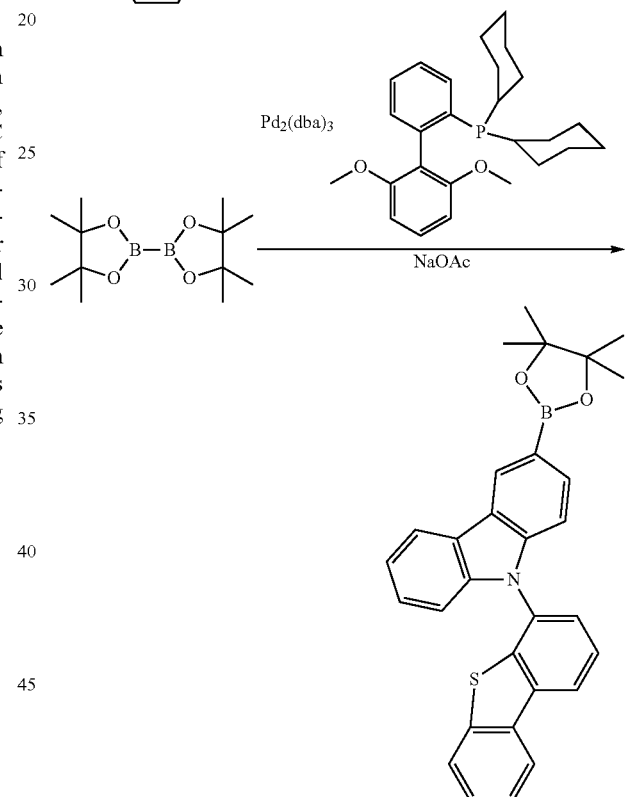

Synthesis of 9-(dibenzo[b,d]thiophen-4-yl)-3-(4,4,5,5-tetramethyl-1,3,2-dioxaborolan-2-yl)-9H-carbazole. 3-bromo-9-(dibenzo[b,d]thiophen-4-yl)-9H-carbazole (5 g, 11.67 mmol), 4,4,4',4',5,5,5',5'-octamethyl-2,2'-bi(1,3,2-dioxaborolane) (4.45 g, 17.51 mmol), potassium acetate (2.86 g, 29.2 mmol), and dicyclohexyl(2',6'-dimethoxy-[1,1'-biphenyl]-2-yl)phosphine (0.192 g, 0.467 mmol) were mixed in 150 ml of dioxane. Nitrogen was bubbled through the solution for 20 min. Pd₂dba₃ (0.107 g, 0.117 mmol) was added and the reaction mixture was heated up to 100° C. for 4 h. TLC indicated the reaction was done. The reaction was cooled to room temperature and filtered through Celite. After solvent evaporation, the residue was coated on Celite and purified by column using 10% ethyl acetate in hexanes as solvent. 9-(dibenzo[b,d]thiophen-4-yl)-3-(4,4,5,5-tetramethyl-1,3,2-dioxaborolan-2-yl)-9H-carbazole (4 g, 8.41 mmol, 72.1% yield) was obtained.

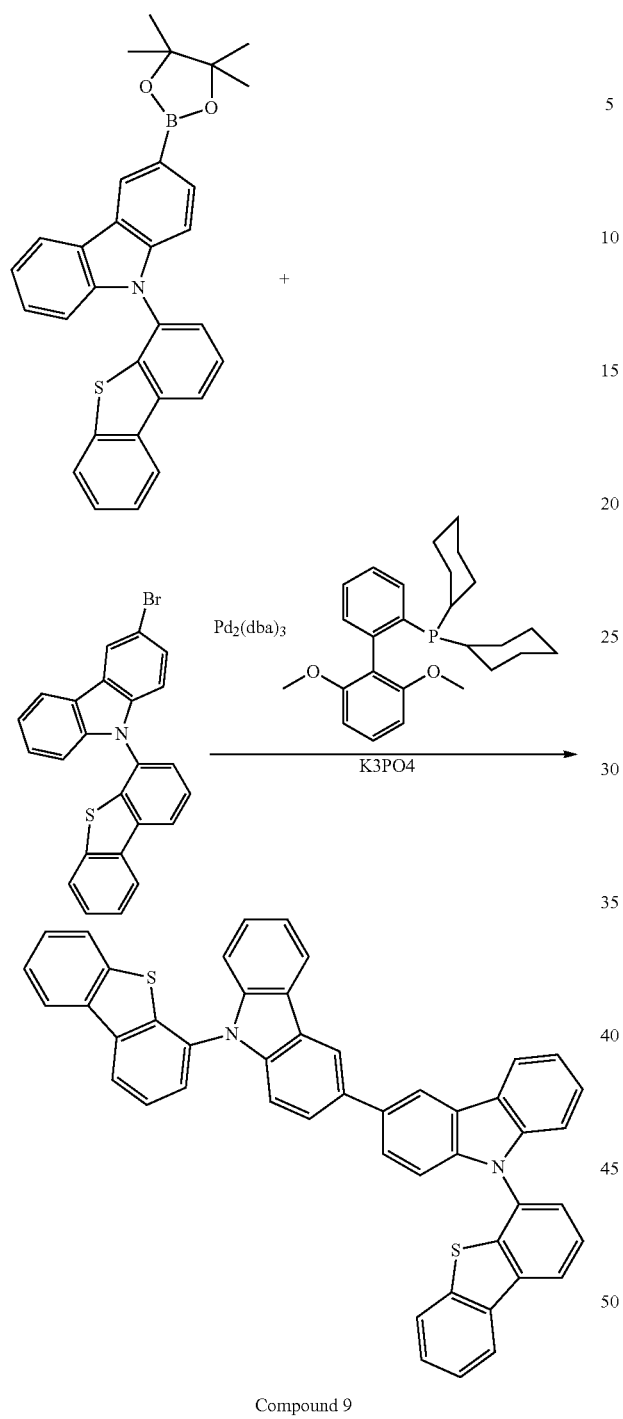

Compound 9

Synthesis of Compound 9. A mixture of 9-(dibenzo[b,d]thiophen-4-yl)-3-(4,4,5,5-tetramethyl-1,3,2-dioxaborolan-2-yl)-9H-carbazole (2.5 g, 5.26 mmol), 3-bromo-9-(dibenzo[b,d]thiophen-4-yl)-9H-carbazole (1.877 g, 4.38 mmol), and potassium phosphate (2.325 g, 10.96 mmol) in 100 mL of toluene and 10 mL of $H_2O$ was bubbled with $N_2$ for 20 min. $Pd_2(dba)_3$ (0.040 g, 0.044 mmol) and dicyclohexyl(2',6'-dimethoxy-[1,1'-biphenyl]-2-yl)phosphine (0.072 g, 0.175 mmol) were then added, and the mixture was heated to reflux under $N_2$ for 24 h. 1 g of phenylboronic acid was added and refluxed for another 4 h. The mixture was cooled and toluene layer was separated. The organic extracts were dried over $MgSO_4$, filtered and evaporated to a residue. The residue was purified by column. 2.4 g (79% yield) of product was obtained after purification.

Device Examples

All device examples were fabricated by high vacuum (<$10^{-7}$ Torr) thermal evaporation. The anode electrode is 800 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package.

The organic stack of the Devices consisted of sequentially, from the ITO surface, 100 Å of Compound B as the hole injection layer (HIL), 300 Å of 4,4'-bis[N-(1-naphthyl)-N-phenylamino]biphenyl (α-NPD) as the hole transporting later (HTL), 300 Å of host doped with 15% or 9% of Compound C as the emissive layer (EML), 50 Å of BL, and 400 Å of $Alq_3$ (tris-8-hydroxyquinoline aluminum) as the ETL.

Comparative Device Examples were fabricated similarly to Device Examples, except H1 or H2 was used as host.

As used herein, the following compounds have the following structures:

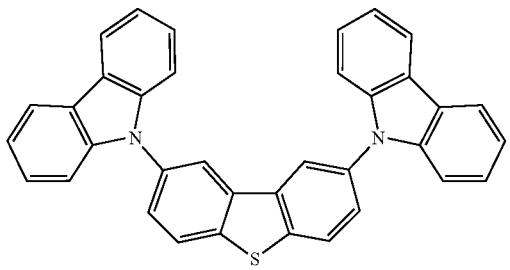

H2

Particular materials for use in an OLED are provided. In particular, the materials may be used as a host or a blocking layer. Device structures are provided in Table 1 and the corresponding measured device data is provided in Table 2. Devices having an emissive layer comprising Compounds 1-5 show improved efficiency and lifetime. In addition, devices having a blocking layer comprising Compound 5 also show improved lifetime and efficiency.

TABLE 1

| Example | HIL | HTL | EML (doping %) | BL | ETL |
|---|---|---|---|---|---|
| Example 1 | E1 | NPD | Compound 1 E2 9% | Compound 1 | Alq |
| Example 2 | E1 | NPD | Compound 1 E2 9% | H2 | Alq |
| Example 3 | E1 | NPD | Compound 1 E2 15% | Compound 1 | Alq |

TABLE 1-continued

| Example | HIL | HTL | EML (doping %) | BL | ETL |
|---|---|---|---|---|---|
| Example 4 | E1 | NPD | Compound 1 E2 15% | H2 | Alq |
| Example 5 | E1 | NPD | Compound 2 E2 9% | Compound 2 | Alq |
| Example 6 | E1 | NPD | Compound 2 E2 9% | H2 | Alq |
| Example 7 | E1 | NPD | Compound 2 E2 15% | Compound 2 | Alq |
| Example 8 | E1 | NPD | Compound 2 E2 15% | H2 | Alq |
| Example 9 | E1 | NPD | Compound 3 E2 9% | Compound 3 | Alq |
| Example 10 | E1 | NPD | Compound 3 E2 9% | H2 | Alq |
| Example 11 | E1 | NPD | Compound 3 E2 9% | Compound 4 | Alq |
| Example 12 | E1 | NPD | Compound 3 E2 15% | Compound 3 | Alq |
| Example 13 | E1 | NPD | Compound 3 E2 15% | H2 | Alq |
| Example 14 | E1 | NPD | Compound 3 E2 15% | Compound 4 | Alq |
| Example 15 | E1 | NPD | Compound 4 E2 9% | Compound 4 | Alq |
| Example 16 | E1 | NPD | Compound 4 E2 9% | H2 | Alq |
| Example 17 | E1 | NPD | Compound 4 E2 15% | Compound 4 | Alq |
| Example 18 | E1 | NPD | Compound 4 E2 15% | H2 | Alq |
| Example 19 | E1 | NPD | H2 | E2 15% | Compound 4 | Alq |
| Example 20 | E1 | NPD | Compound 5 E2 9% | Compound 5 | Alq |
| Example 21 | E1 | NPD | Compound 5 E2 9% | H2 | Alq |
| Example 22 | E1 | NPD | Compound 5 E2 15% | Compound 5 | Alq |
| Example 23 | E1 | NPD | Compound 5 E2 15% | H2 | Alq |
| Comparative Example 1 | E1 | NPD | H1 E2 9% | H1 | Alq |
| Comparative Example 2 | E1 | NPD | H1 E2 9% | H2 | Alq |
| Comparative Example 3 | E1 | NPD | H1 E2 15% | H1 | Alq |
| Comparative Example 4 | E1 | NPD | H1 E2 15% | H2 | Alq |
| Comparative Example 5 | E1 | NPD | H2 E2 15% | H2 | Alq |

TABLE 2

| | 1931 CIE | | | FWHM | At 1000 nits | | | | At 2000 nits |
|---|---|---|---|---|---|---|---|---|---|
| Example | x | y | $\lambda_{max}$ | (nm) | Voltage (V) | LE (Cd/A) | EQE (%) | PE (lm/W) | $LT_{80\%}$ (h) |
| Example 1 | 0.186 | 0.408 | 474 | 60 | 8.9 | 27.3 | 11.6 | 9.6 | 122 |
| Example 2 | 0.185 | 0.405 | 474 | 60 | 6.8 | 33.1 | 14.1 | 15.3 | 185 |
| Example 3 | 0.186 | 0.409 | 474 | 60 | 8.1 | 22.1 | 9.3 | 8.5 | 60 |
| Example 4 | 0.182 | 0.400 | 474 | 58 | 6.1 | 43.2 | 18.6 | 22.4 | 115 |
| Example 5 | 0.186 | 0.415 | 474 | 62 | 8.8 | 26.7 | 11.2 | 9.5 | 68 |
| Example 6 | 0.185 | 0.411 | 474 | 62 | 7 | 32.3 | 13.6 | 14.6 | 123 |
| Example 7 | 0.187 | 0.413 | 474 | 62 | 8.1 | 21.2 | 8.9 | 8.2 | 29 |
| Example 8 | 0.183 | 0.405 | 474 | 60 | 6.2 | 42.3 | 18 | 21.6 | 90 |
| Example 9 | 0.186 | 0.410 | 474 | 60 | 8.8 | 27 | 11.4 | 9.6 | 244 |
| Example 10 | 0.185 | 0.406 | 474 | 60 | 7.4 | 31.2 | 13.3 | 13.2 | 350 |
| Example 11 | 0.185 | 0.407 | 474 | 60 | 7.1 | 32.2 | 13.7 | 14.3 | 282 |
| Example 12 | 0.185 | 0.409 | 474 | 60 | 7.7 | 28.3 | 12 | 11.5 | 270 |
| Example 13 | 0.182 | 0.403 | 474 | 60 | 6.4 | 42.7 | 18.3 | 21.0 | 310 |
| Example 14 | 0.182 | 0.403 | 474 | 60 | 6.2 | 44.9 | 19.3 | 22.7 | 305 |
| Example 15 | 0.207 | 0.441 | 474 | 76 | 7 | 19.4 | 7.7 | 8.7 | 60 |
| Example 16 | 0.206 | 0.439 | 474 | 74 | 7.5 | 19.9 | 7.9 | 8.3 | 55 |
| Example 17 | 0.212 | 0.448 | 474 | 78 | 6.1 | 26.3 | 10.3 | 13.5 | 92 |
| Example 18 | 0.211 | 0.446 | 474 | 76 | 6.5 | 27 | 10.6 | 13.0 | 64 |
| Example 19 | 0.180 | 0.394 | 474 | 58 | 5.6 | 45.4 | 19.8 | 25.5 | 230 |
| Example 20 | 0.196 | 0.430 | 474 | 66 | 7.1 | 23.3 | 9.4 | 10.3 | 30 |
| Example 21 | 0.194 | 0.425 | 474 | 64 | 7.2 | 23.8 | 9.7 | 10.3 | 28 |
| Example 22 | 0.196 | 0.432 | 474 | 66 | 6.2 | 29.6 | 12 | 14.9 | 28 |
| Example 23 | 0.195 | 0.427 | 474 | 64 | 6.4 | 30.6 | 12.5 | 15.0 | 24 |
| Comparative Example 1 | 0.210 | 0.434 | 474 | 76.0 | 12.2 | 5.2 | 2.1 | 1.3 | 0.5 |
| Comparative Example 2 | 0.182 | 0.394 | 474 | 58.0 | 8.7 | 27.2 | 11.9 | 9.8 | 10 |
| Comparative Example 3 | 0.223 | 0.451 | 506 | 86.0 | 11.6 | 3.6 | 1.4 | 1.0 | 0.2 |
| Comparative Example 4 | 0.184 | 0.395 | 474 | 58.0 | 8.3 | 24.6 | 10.7 | 9.3 | 6 |
| Comparative Example 5 | 0.178 | 0.389 | 474 | 56 | 5.9 | 45.9 | 20.2 | 24.6 | 204 |

Comparative Examples 1-4 used H1 as host and/or blocking layer. When H1 was used as a host and a blocking layer, the efficiencies were 2.1% for 9% doping and 1.4% for 15% doping. Device lifetimes ($LT_{80}$) from 2000 cd/m$^2$ were 0.5 h and 0.2 h, respectively. Small improvements were made using H2 as BL. However, the lifetime of the devices was still no more than 10 h from an initial brightness of 2000 cd/m$^2$.

As can be seen from Device Examples 1-23, inventive compounds gave much better device efficiencies and lifetimes when used as a host. For example, Device Example 10 showed a lifetime of 350 h when Compound 3 was used as the host.

In addition, inventive compounds with azadibenzothiophene or azadibenzofuran can also be used as blocking layer. Comparative Example 5 used H2 as a host and a blocking layer. At 5.9 V, the device reached 1000 cd/m$^2$ with an efficiency of 20.5%. The lifetime was 204 h. As shown in Device Example 19, which used Compound 4 as the blocking layer, the device reached 1000 cd/m$^2$ at 5.6 V with an efficiency of 19.8%. The lifetime was 230 h. Device Example 19 showed lower operating voltage than the corresponding Comparative Example 5 and maintained comparable device efficiency. Additionally, Device Example 19 demonstrated improved operational lifetime, compared to the Comparative Example 5, by providing a lifetime of 204 h compared to 230 h.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound comprising a bicarbazole, wherein the compound has the formula:

Formula I

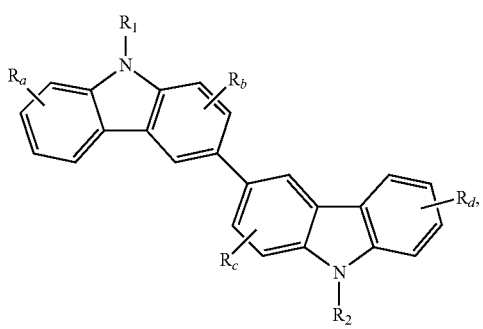

wherein $R_a$, $R_b$, $R_c$, and $R_d$ may represent mono, di, tri, or tetra substitutions;

wherein $R_a$, $R_b$, $R_c$, $R_d$, $R_1$, and $R_2$ are independently selected from the group consisting of hydrogen, alkyl, alkoxy, amino, alkenyl, alkynyl, aryl and heteroaryl;

wherein at least one of $R_1$ and $R_2$ has the formula:

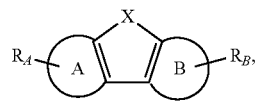

wherein A and B are independently 5 or 6 membered carbocyclic or heterocyclic rings;

wherein $R_A$ and $R_B$ are independently selected from the group consisting of hydrogen, alkyl, alkoxy, amino, alkenyl, alkynyl, aryl and heteroaryl; and wherein X is S, O or Se.

2. The compound of claim 1, wherein $R_1$ and $R_2$ are independently selected from aryl and heteroaryl.

3. The compound of claim 1, wherein only one of $R_1$ and $R_2$ has the formula:

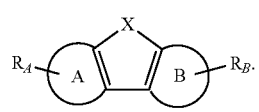

4. The compound of claim 1, wherein both $R_1$ and $R_2$ have the formula:

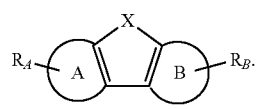

5. The compound of claim 1, wherein at least one of $R_1$ and $R_2$ has the formula:

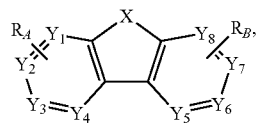

wherein $R_A$ and $R_B$ may represent mono, di, tri, or tetra substitutions;

wherein $R_A$ and $R_B$ are independently selected from the group consisting of hydrogen, alkyl, alkoxy, amino, alkenyl, alkynyl, aryl and heteroaryl; and wherein $Y_1$, $Y_2$, $Y_3$, $Y_4$, $Y_5$, $Y_6$, $Y_7$, and $Y_8$ are independently selected from nitrogen and carbon.

6. The compound of claim 1, wherein A and B are independently selected from phenyl and pyridine.

7. The compound of claim 1, wherein $R_1$ and $R_2$ are independently selected from the group consisting of:

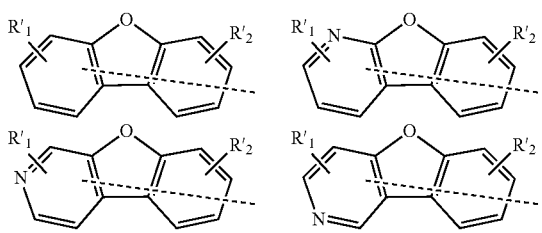

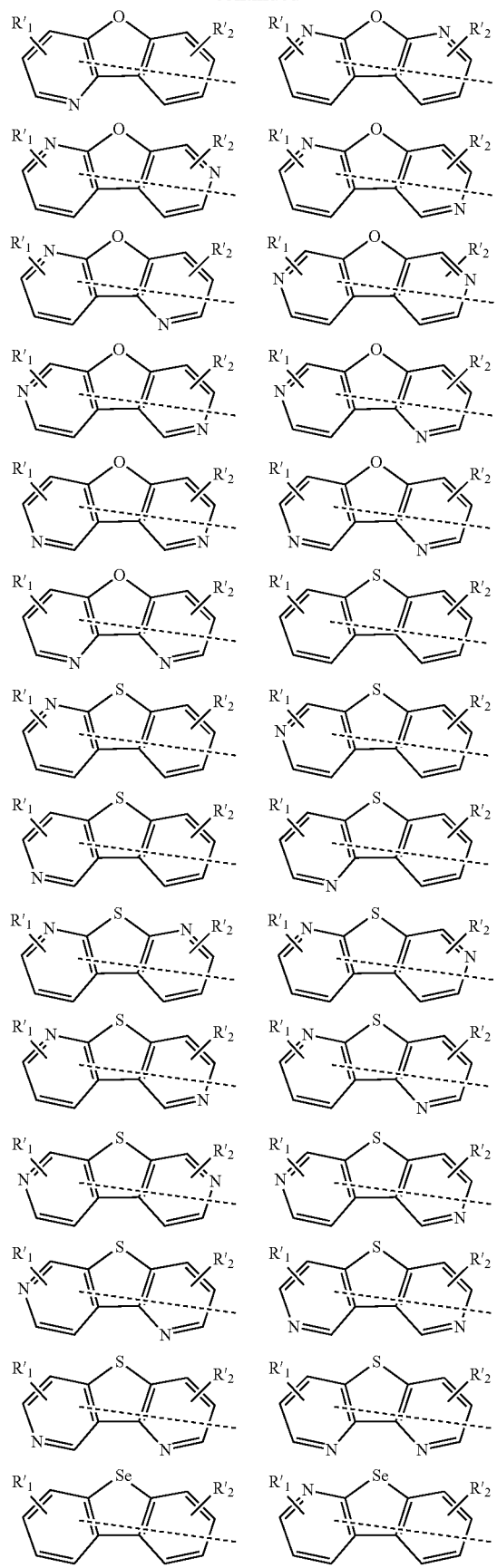
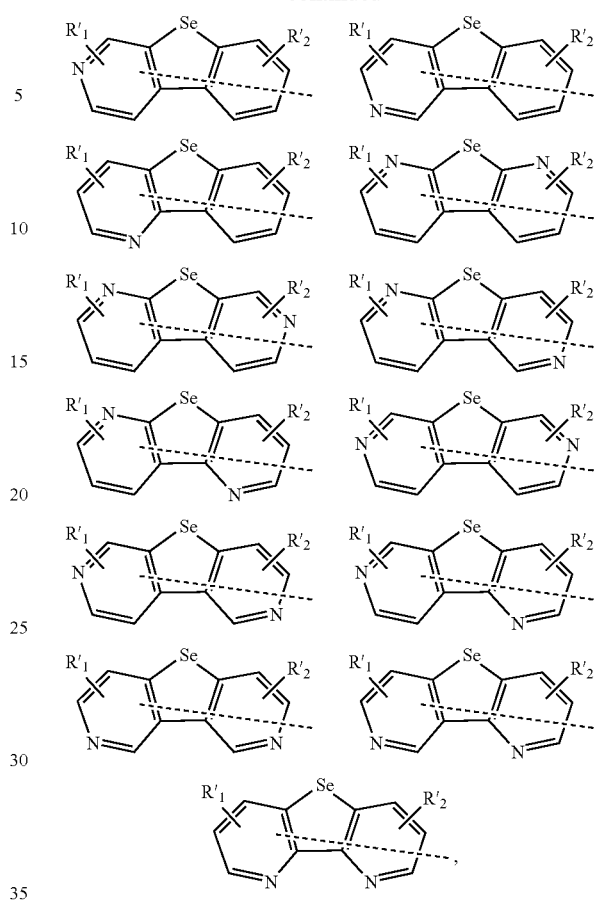
wherein R'₁ and R'₂ are independently selected from the group consisting of hydrogen, alkyl, alkoxy, amino, alkenyl, alkynyl, aryl and heteroaryl.
8. The compound of claim 1, wherein the compound has the formula:
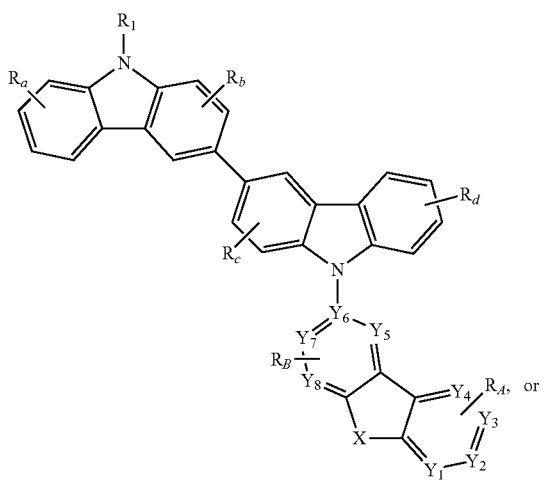
Formula II -continued

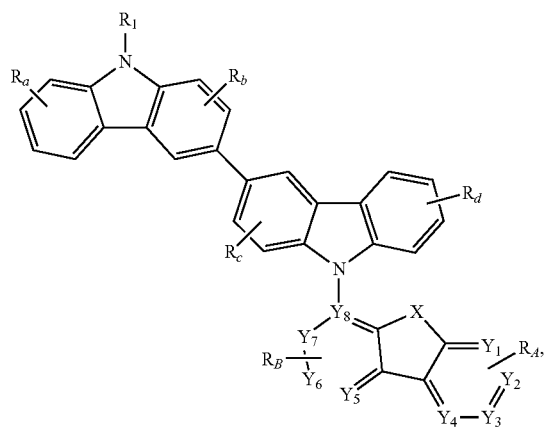

Formula III wherein $R_A$ and $R_B$ may represent mono, di, tri, or tetra substitutions;

wherein $R_A$ and $R_B$ are independently selected from the group consisting of hydrogen, alkyl, alkoxy, amino, alkenyl, alkynyl, aryl and heteroaryl; and wherein $Y_1$, $Y_2$, $Y_3$, $Y_4$, $Y_5$, $Y_6$, $Y_7$, and $Y_8$ are independently selected from nitrogen and carbon.

9. The compound of claim 1, wherein the compound is selected from the group consisting of:

Compound 1

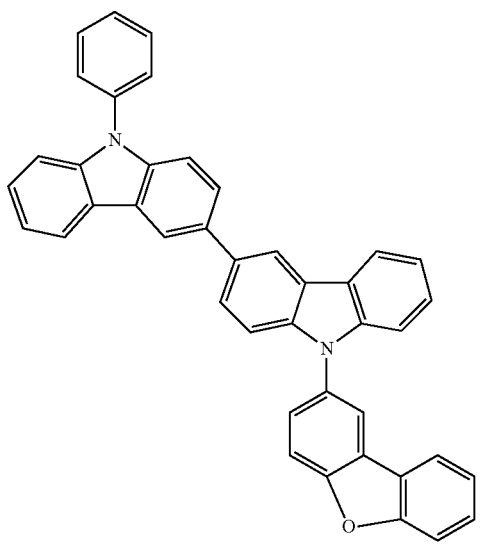

-continued

Compound 2

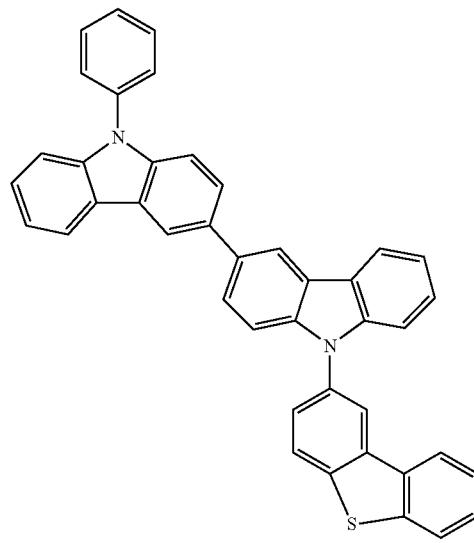

Compound 3

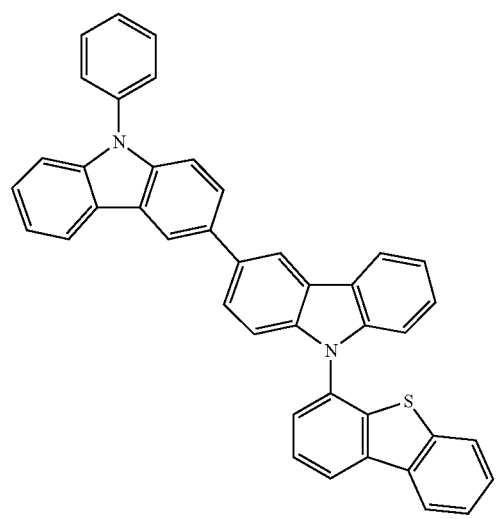

Compound 4

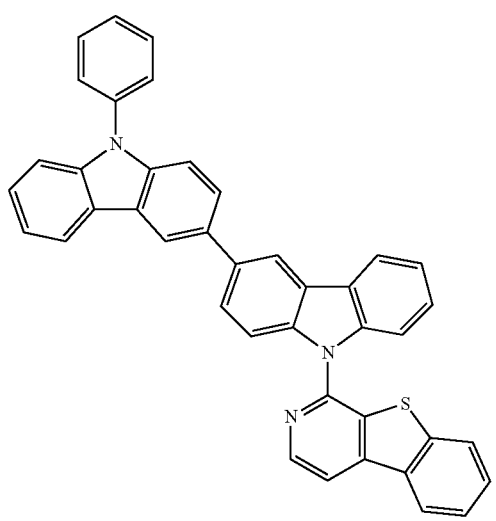

Compound 5
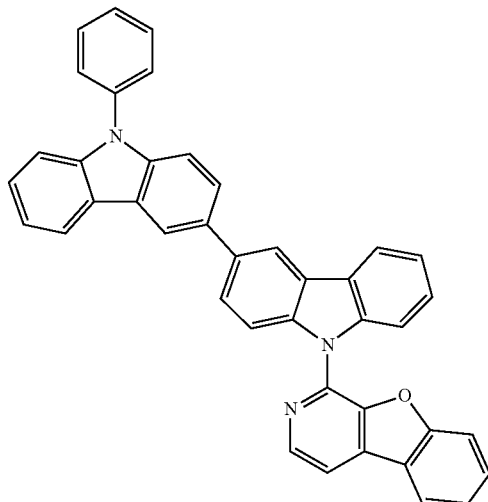
Compound 6
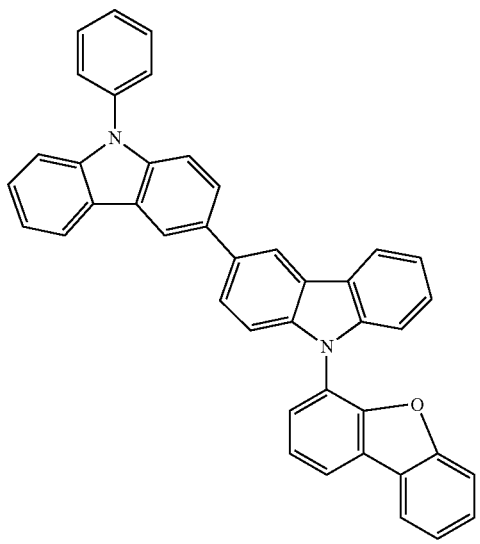
Compound 7
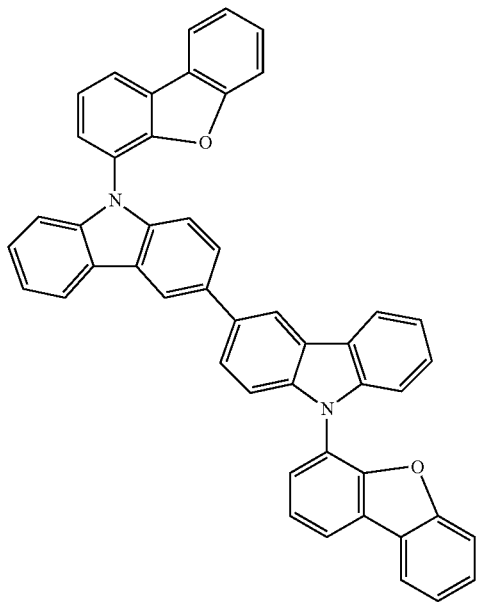
Compound 8
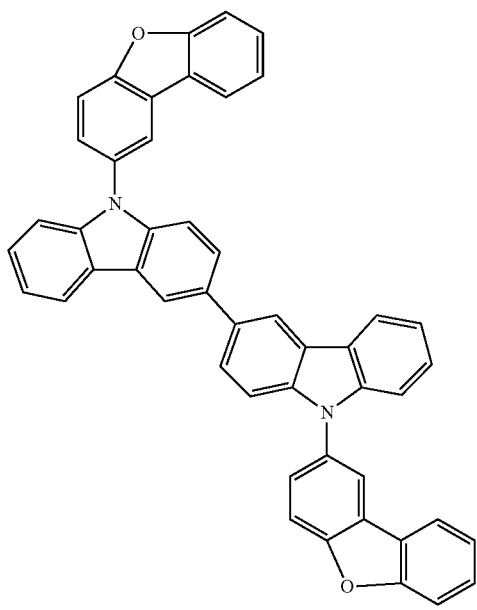

Compound 9
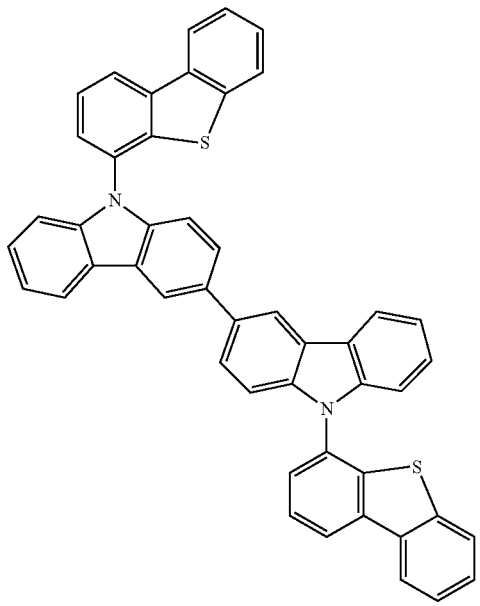
Compound 10
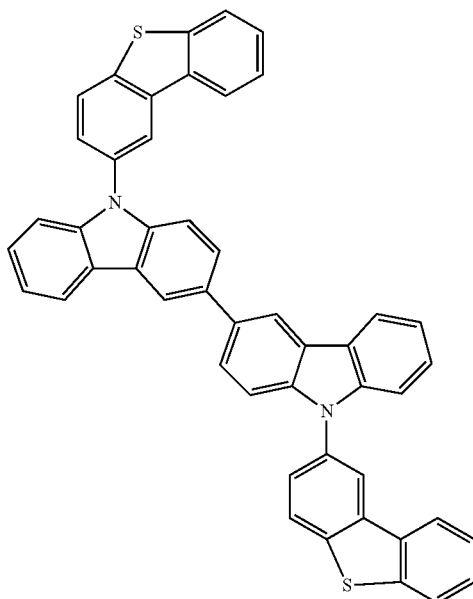
Compound 11
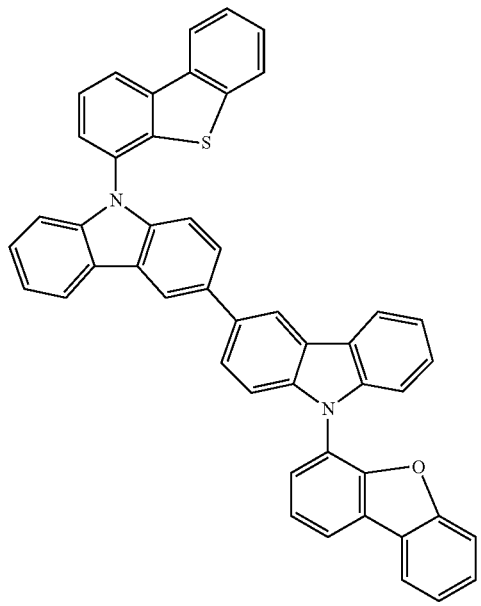
Compound 12
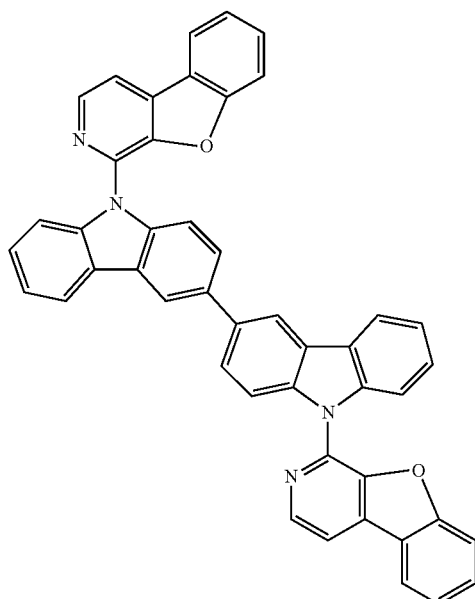

Compound 13
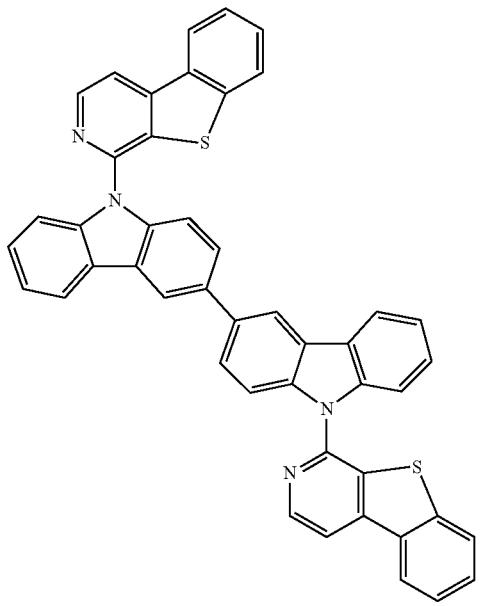
Compound 14
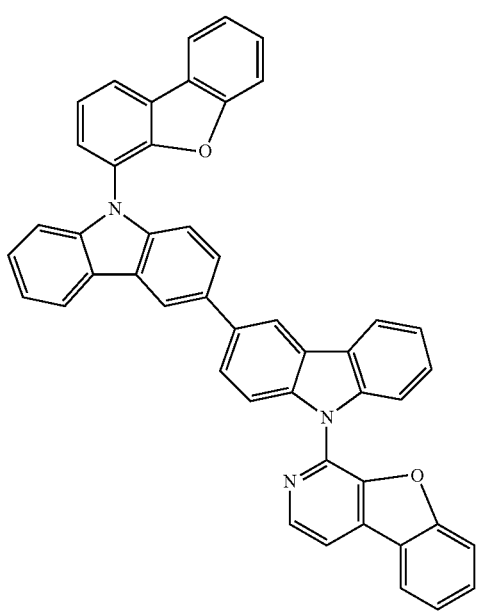
Compound 15
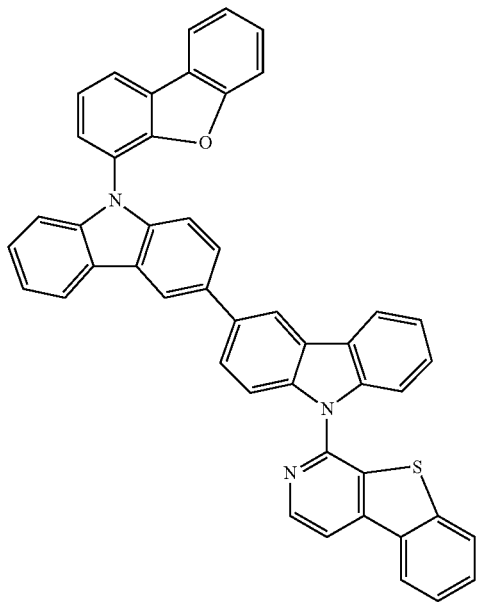
Compound 16
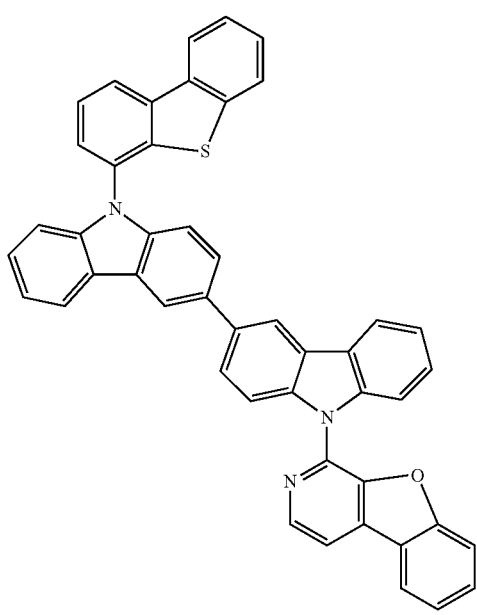

Compound 17

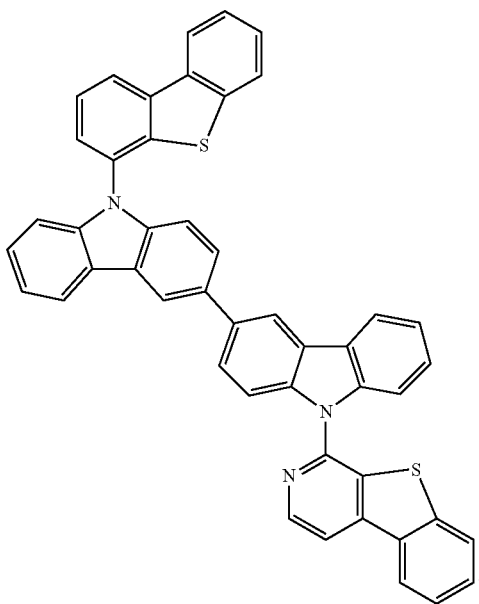

10. A first device comprising an organic light emitting device further comprising:
an anode;
a cathode; and
an organic layer, disposed between the anode and the cathode, wherein the organic layer comprises a compound comprising a bicarbazole, wherein the compound has the formula:

Formula I

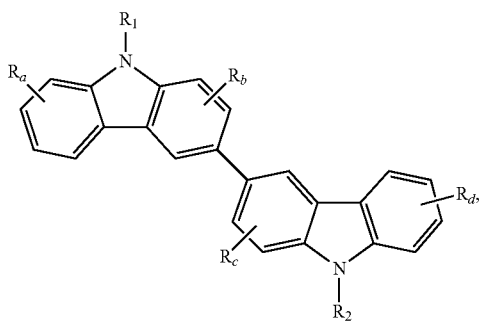

wherein $R_a$, $R_b$, $R_c$, and $R_d$ may represent mono, di, tri, or tetra substitutions;
wherein $R_a$, $R_b$, $R_c$, $R_d$, $R_1$, and $R_2$ are independently selected from the group consisting of hydrogen, alkyl, alkoxy, amino, alkenyl, alkynyl, aryl and heteroaryl;
wherein at least one of $R_1$ and $R_2$ has the formula:

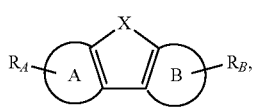

wherein A and B are independently 5 or 6 membered carbocyclic or heterocyclic rings;

wherein $R_A$ and $R_B$ are independently selected from the group consisting of hydrogen, alkyl, alkoxy, amino, alkenyl, alkynyl, aryl and heteroaryl; and
wherein X is S, O or Se.

11. The device of claim 10, wherein $R_1$ and $R_2$ are independently selected from aryl and heteroaryl.

12. The first device of claim 10, wherein only one of $R_1$ and $R_2$ has the formula:

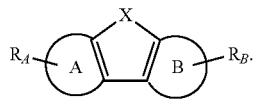

13. The device of claim 10, wherein both $R_1$ and $R_2$ have the formula:

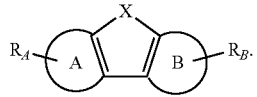

14. The first device of claim 10, wherein at least one of $R_1$ and $R_2$ has the formula:

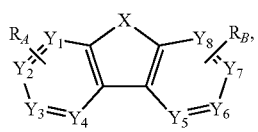

wherein $R_A$ and $R_B$ may represent mono, di, tri, or tetra substitutions;
wherein $R_A$ and $R_B$ are independently selected from the group consisting of hydrogen, alkyl, alkoxy, amino, alkenyl, alkynyl, aryl and heteroaryl; and
wherein $Y_1$, $Y_2$, $Y_3$, $Y_4$, $Y_5$, $Y_6$, $Y_7$, and $Y_8$ are independently selected from nitrogen and carbon.

15. The first device of claim 10, wherein A and B are independently selected from phenyl and pyridine.

16. The first device of claim 10, wherein $R_1$ and $R_2$ are independently selected from the group consisting of:

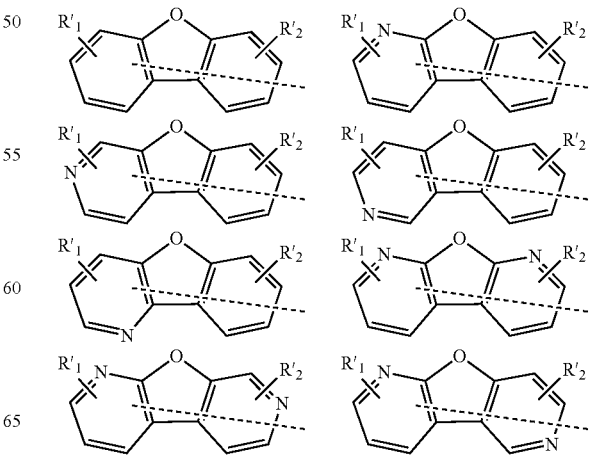

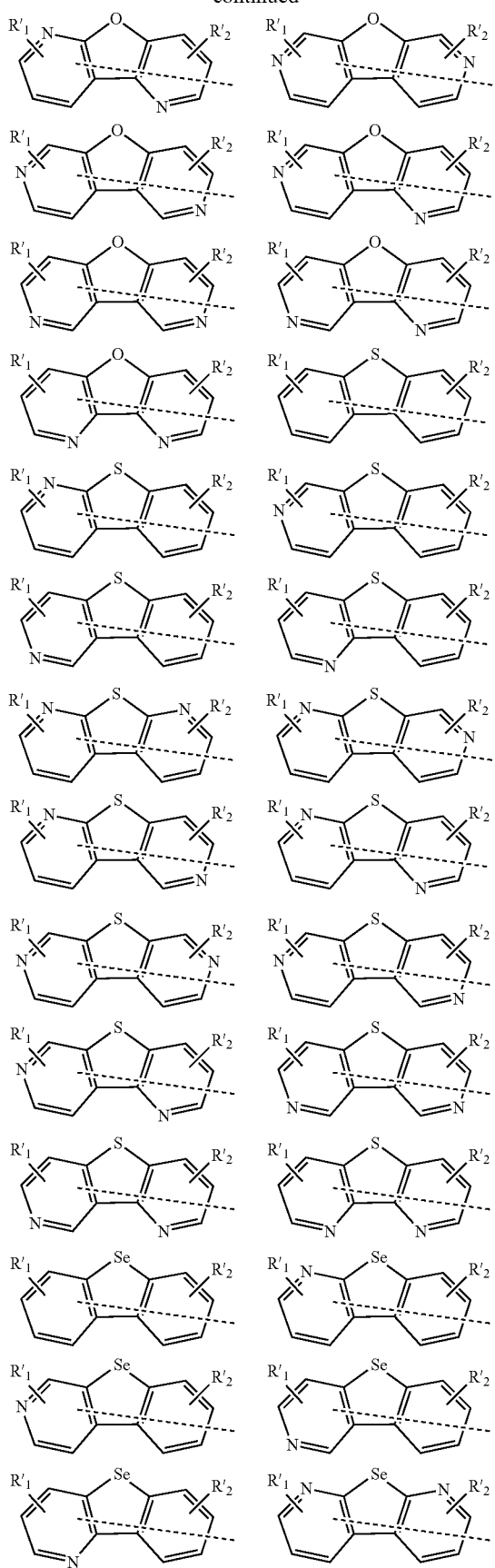
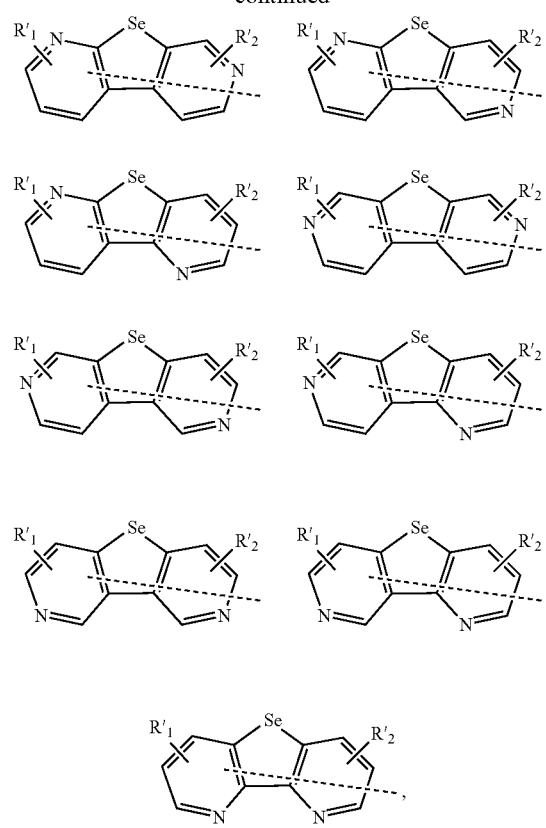
wherein R'₁ and R'₂ are independently selected from the group consisting of hydrogen, alkyl, alkoxy, amino, alkenyl, alkynyl, aryl and heteroaryl.
17. The first device of claim 10, wherein the compound has the formula:
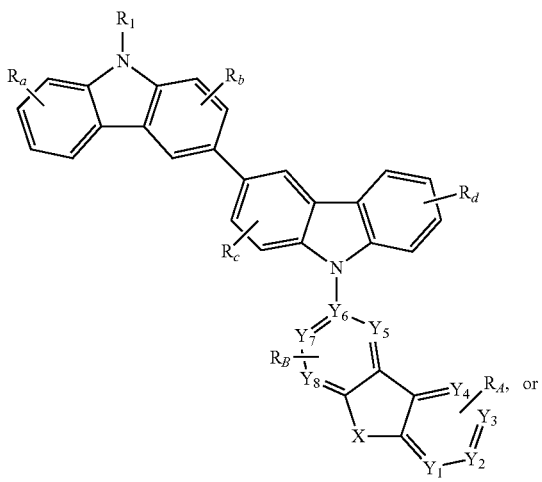
Formula II Formula III

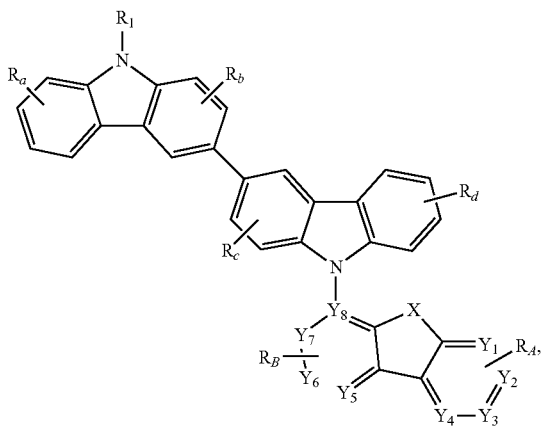

wherein $R_A$ and $R_B$ may represent mono, di, tri, or tetra substitutions;

wherein $R_A$ and $R_B$ are independently selected from the group consisting of hydrogen, alkyl, alkoxy, amino, alkenyl, alkynyl, aryl and heteroaryl; and wherein $Y_1$, $Y_2$, $Y_3$, $Y_4$, $Y_5$, $Y_6$, $Y_7$, and $Y_8$ are independently selected from nitrogen and carbon.

18. The first device of claim 10, wherein the compound is selected from the group consisting of:

Compound 1

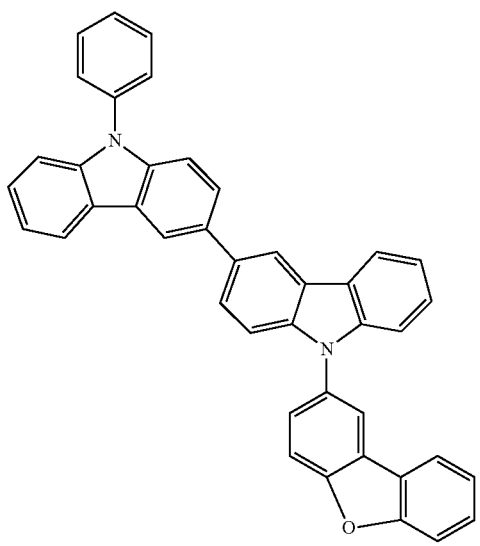

Compound 2

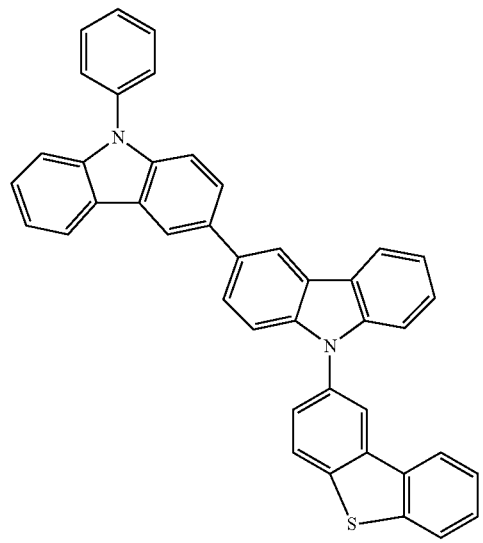

Compound 3

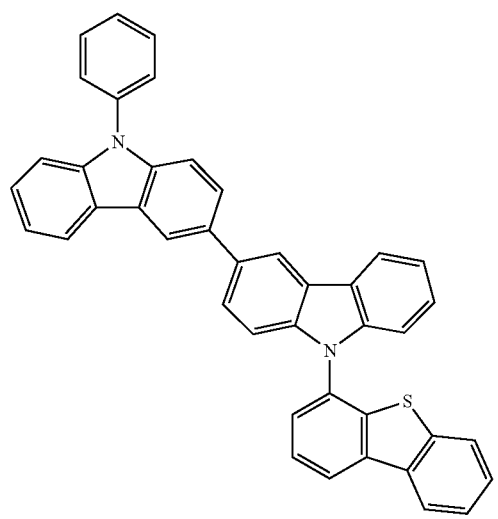

Compound 4

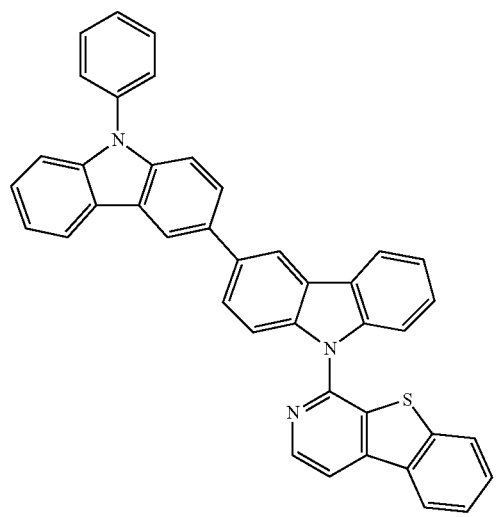

Compound 5
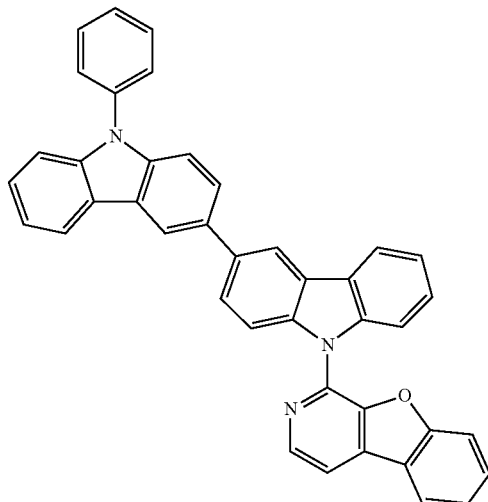
Compound 6
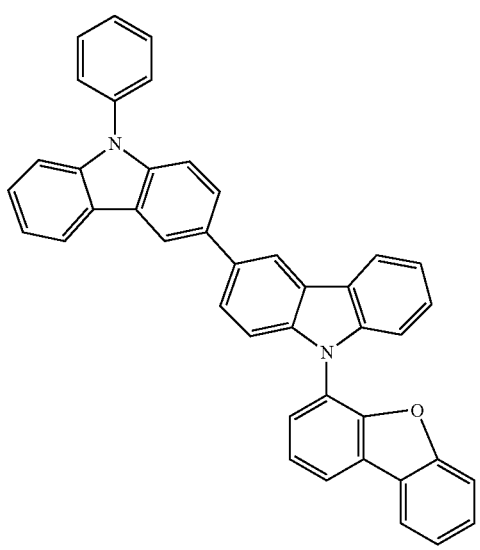
Compound 7
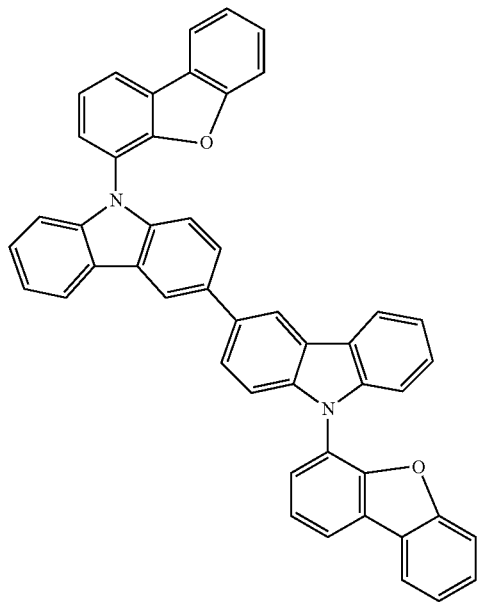
Compound 8
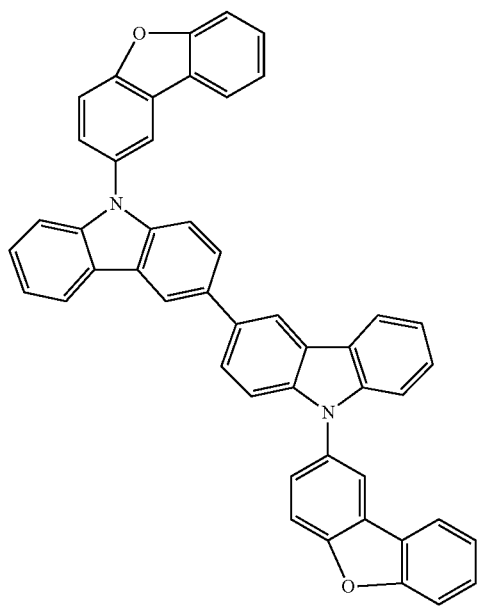

Compound 9
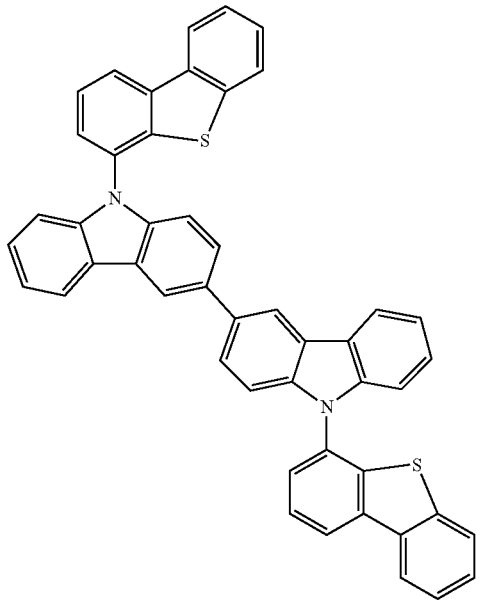
Compound 10
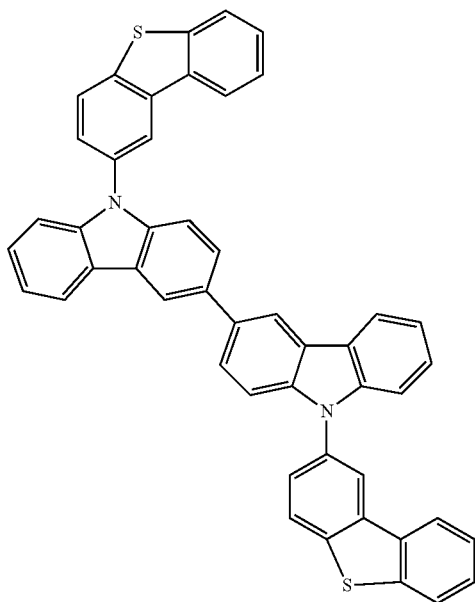
Compound 11
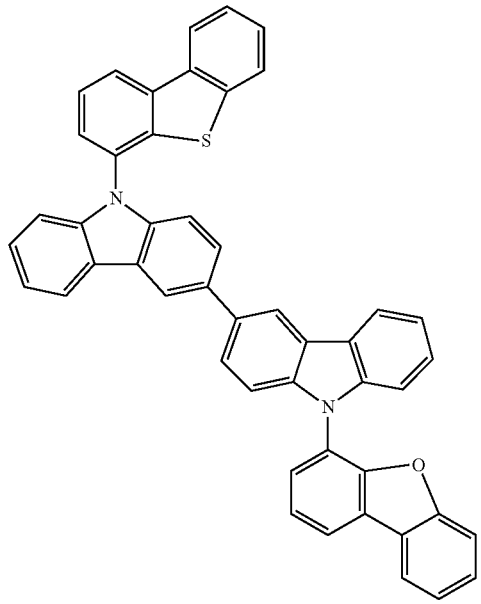
Compound 12
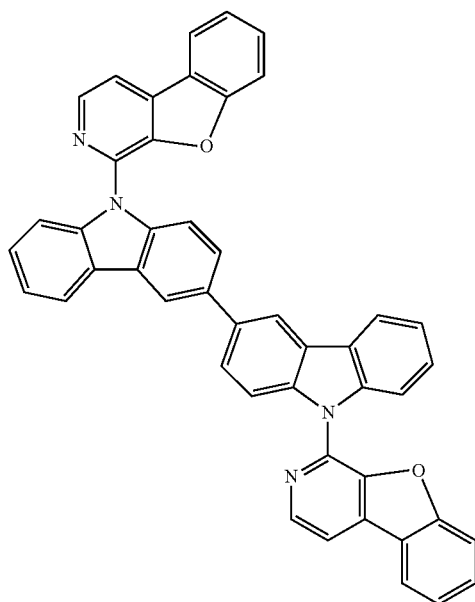

Compound 13
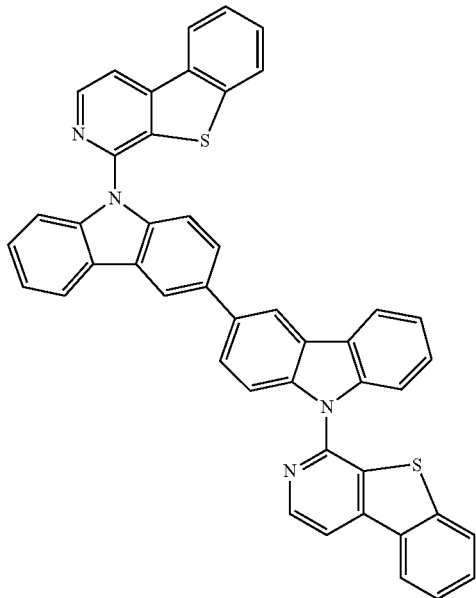
Compound 14
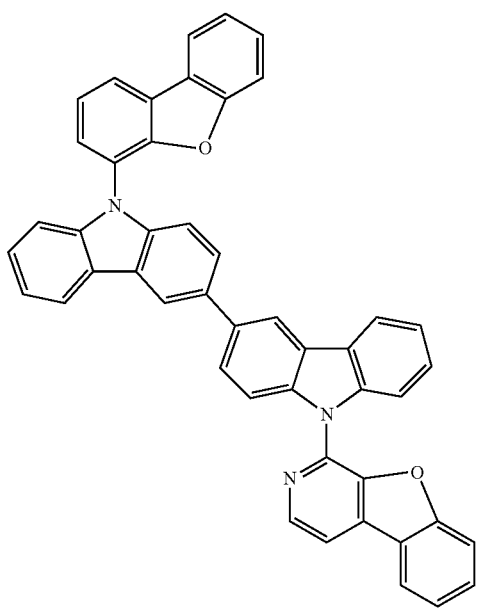
Compound 15
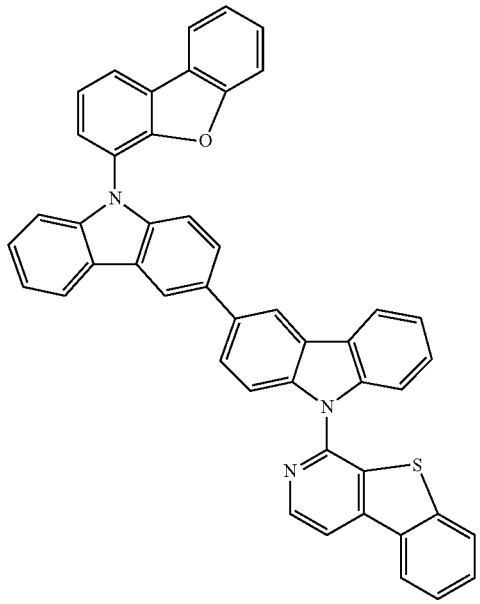
Compound 16
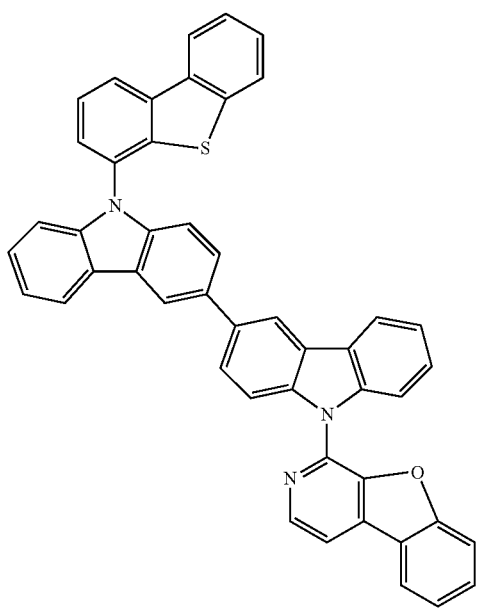

Compound 17

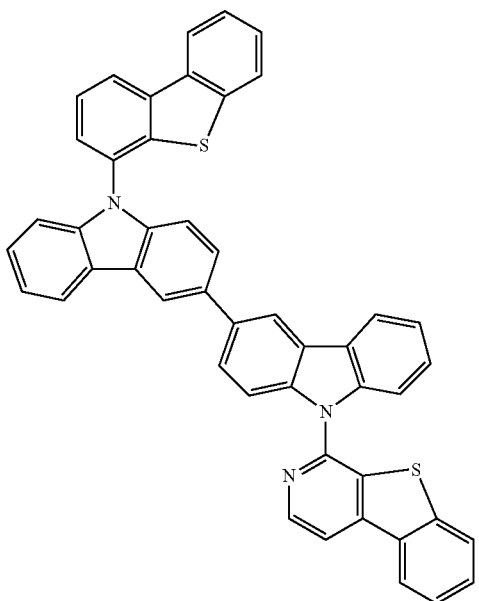

19. The first device of claim 10, wherein the organic layer is a blocking layer and the compound having Formula I is a blocking material.

20. The first device of claim 10, wherein the organic layer is an emissive layer and the compound having Formula I is a host.

21. The device of claim 20, wherein the emissive layer further comprises a phosphorescent emissive dopant having the formula:

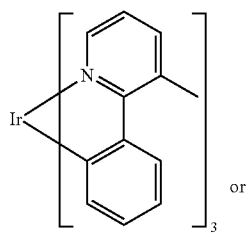
E1 or

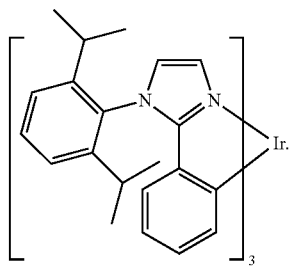
E2

22. The first device of claim 10, wherein the first device is a consumer product.

23. The first device of claim 10, wherein the first device is an organic light emitting device.

* * * * *